US010815520B2

(12) United States Patent
Zhang

(10) Patent No.: US 10,815,520 B2
(45) Date of Patent: Oct. 27, 2020

(54) NANOVESICLES, METHODS, AND SYSTEMS FOR DIAGNOSIS AND PROGNOSIS OF CANCER

(71) Applicant: University of Louisville Research Foundation, Inc., Louisville, KY (US)

(72) Inventor: Huang-Ge Zhang, Louisville, KY (US)

(73) Assignee: University of Louisville Research Foundation, Inc., Louisville, KY (US)

(*) Notice: Subject to any disclaimer, the term of this patent is extended or adjusted under 35 U.S.C. 154(b) by 154 days.

(21) Appl. No.: 15/948,218

(22) Filed: Apr. 9, 2018

(65) Prior Publication Data
US 2018/0291433 A1    Oct. 11, 2018

Related U.S. Application Data

(60) Provisional application No. 62/482,754, filed on Apr. 7, 2017.

(51) Int. Cl.
*C12Q 1/6813* (2018.01)
*G01N 33/68* (2006.01)
(Continued)

(52) U.S. Cl.
CPC ......... *C12Q 1/6813* (2013.01); *C12Q 1/6886* (2013.01); *G01N 33/4833* (2013.01);
(Continued)

(58) Field of Classification Search
None
See application file for complete search history.

(56) References Cited

U.S. PATENT DOCUMENTS

2004/0028692 A1   2/2004   Zitvogel et al.
2004/0138189 A1   7/2004   Sebti et al.
(Continued)

FOREIGN PATENT DOCUMENTS

WO   WO 2004/019916   3/2004
WO   WO 2008/092153   7/2008
(Continued)

OTHER PUBLICATIONS

Shin, S. et al. Separation of extracellular nanovesicles and apoptotic bodies from cancer cell culture broth using tunable microfluidic systems, Scientific Reports, vol. 7, 9907 (Year: 2017).*
(Continued)

*Primary Examiner* — Xiaoyun R Xu
(74) *Attorney, Agent, or Firm* — Jenkins, Wilson, Taylor & Hunt, P.A.

(57) ABSTRACT

Methods for diagnosis or prognosis of a cancer in a subject include isolating one or more nanovesicles from a biological sample obtained from the subject, determining the amount in the biological sample of the one or more nanovesicles, and comparing the amount of the one or more nanovesicles to a control level to thereby diagnose the cancer. The one or more nanovesicles are obtained by depleting the biological sample of exosomes prior to the isolation of the nanovesicles. Methods for identifying a tumor metastasis in a subject are also provided and include fractionating a biological sample from a subject to obtain a fraction including one or more exosomes and one or more nanovesicles having a diameter of about 8-12 nm, and then isolating the one or more nanovesicles to diagnose the tumor metastasis.

17 Claims, 27 Drawing Sheets

(51) Int. Cl.
    *G01N 33/483*  (2006.01)
    *C12Q 1/6886*  (2018.01)
    *G01N 33/574*  (2006.01)
(52) U.S. Cl.
    CPC ....... *G01N 33/57484* (2013.01); *G01N 33/68* (2013.01); *G01N 33/6848* (2013.01); *G01N 33/6893* (2013.01); *G01N 2800/50* (2013.01); *G01N 2800/52* (2013.01)

(56) References Cited

U.S. PATENT DOCUMENTS

| | | |
|---|---|---|
| 2010/0209415 A1 | 8/2010 | Smith et al. |
| 2012/0183575 A1 | 7/2012 | Gabrielsson |
| 2012/0315324 A1 | 12/2012 | Zhang |
| 2013/0115241 A1 | 5/2013 | Gho |
| 2013/0129790 A1 | 5/2013 | Alexis et al. |
| 2014/0308212 A1 | 10/2014 | Zhang |
| 2017/0035700 A1 | 2/2017 | Zhang |
| 2018/0140654 A1 | 5/2018 | Zhang |
| 2018/0362974 A1 | 12/2018 | Zhang |

FOREIGN PATENT DOCUMENTS

| | | |
|---|---|---|
| WO | WO 2009/065561 | 5/2009 |
| WO | WO 2010/096597 | 8/2010 |
| WO | WO 2011/097480 | 8/2011 |
| WO | WO 2013/048734 | 4/2013 |
| WO | WO 2013/070324 | 5/2013 |
| WO | WO 2014/028487 | 2/2014 |
| WO | WO 2015/058148 | 4/2015 |

OTHER PUBLICATIONS

Admyre et al. Exosomes with immune modulatory features are present in human breast milk. Journal of immunology. 2007; 179(3):1969-1978.
Akers et al. MiR-21 in the extracellular vesicles (EVs) of cerebrospinal fluid (CSF): a platform for glioblastoma biomarker development. PloS one. 2013; 8(10):e78115.
Antonyak & Cerione, Microvesicles as mediators of intercellular communication in cancer. Methods in molecular biology. 2014; 1165:147-173.
Asea et al. Heat shock protein-containing exosomes in mid-trimester amniotic fluids. Journal of reproductive immunology. 2008; 79(1):12-17.
Caby et al. Exosomal-like vesicles are present in human blood plasma. International immunology. 2005; 17(7):879-887.
Clancy et al. Regulated delivery of molecular cargo to invasive tumour-derived microvesicles. Nature communications. 2015; 6:6919.
Colombo et al. Biogenesis, secretion, and intercellular interactions of exosomes and other extracellular vesicles. Annual review of cell and developmental biology. 2014; 30:255-289.
D'Souza-Schorey & Clancy. Tumor-derived microvesicles: shedding light on novel microenvironment modulators and prospective cancer biomarkers. Genes & development. 2012; 26(12):1287-1299.
Denzer et al. Exosome: from internal vesicle of the multivesicular body to intercellular signaling device. Journal of cell science. 2000; 113 Pt 19:3365-3374.
Gutwein et al. Cleavage of L1 in exosomes and apoptotic membrane vesicles released from ovarian carcinoma cells. Clinical cancer research: an official journal of the American Association for Cancer Research, 2005; 11(7):2492-2501.
Hoshino et al. Tumour exosome integrins determine organotropic metastasis. Nature. 2015; 527(7578):329-335.
Ju et al. Grape exosome-like nanoparticles induce intestinal stem cells and protect mice from DSS-induced colitis. Molecular therapy: the journal of the American Society of Gene Therapy. 2013; 21(7):1345-1357.

Lemoinne et al. The emerging roles of microvesicles in liver diseases. Nature reviews Gastroenterology & Hepatology. 2014; 11(6):350-361.
Liu et al. Contribution of MyD88 to the tumor exosome-mediated induction of myeloid derived suppressor cells. The American journal of pathology, 2010a; 176(5):2490-2499.
Liu et al. Contribution of MyD88 to the tumor exosome-mediated induction of myeloid derived suppressor cells. The American journal of pathology. 2010b; 176(5):2490-2499.
Liu et al. Murine mammary carcinoma exosomes promote tumor growth by suppression of NK cell function. Journal of immunology. 2006; 176(3):1375-1385.
Liu et al. Passive tumor targeting of renal-clearable luminescent gold nanoparticles: long tumor retention and fast normal tissue clearance. Journal of the American Chemical Society, 2013; 135(13):4978-4981.
Masyuk et al. Biliary exosomes influence cholangiocyte regulatory mechanisms and proliferation through interaction with primary cilia. American journal of physiology Gastrointestinal and liver physiology. 2010; 299(4):G990-999.
Minciacchi et al. Extracellular vesicles in cancer: exosomes, microvesicles and the emerging role of large oncosomes. Seminars in Cell & Developmental Biology, 2015; 40:41-51.
Mu et al. Interspecies communication between plant and mouse gut host cells through edible plant derived exosome-like nanoparticles. Molecular nutrition & food research. 2014; 58(7):1561-1573.
Nakano et al. Extracellular vesicles in the biology of brain tumour stem cells—implications for inter-cellular communication, therapy and biomarker development. Seminars in cell & developmental biology. 2015; 40:17-26.
Navabi et al. Preparation of human ovarian cancer ascites-derived exosomes for a clinical trial. Blood cells, molecules & diseases. 2005; 35(2):149-152.
Osawa et al. Liver acid sphingomyelinase inhibits growth of metastatic colon cancer. The Journal of clinical investigation. 2013; 123(2)834-843.
Redzic et al. Glioblastoma extracellular vesicles: reservoirs of potential biomarkers. Pharmacogenomics and personalized medicine. 2014; 7:65-77.
Thery. Cancer: Diagnosis by extracellular vesicles. Nature. 2015; 523(7559):161-162.
Vader et al. Extracellular vesicles: emerging targets for cancer therapy. Trends in molecular medicine. 2014; 20(7):385-393.
Valadi et al. Exosome-mediated transfer of mRNAs and microRNAs is a novel mechanism of genetic exchange between cells. Nature cell biology. 2007; 9(6):654-659.
Wang et al. Delivery of therapeutic agents by nanoparticles made of grapefruit-derived lipids. Nature communications. 2013; 4:1867.
Wang et al. Grapefruit-Derived Nanovectors Use an Activated Leukocyte Trafficking Pathway to Deliver Therapeutic Agents to Inflammatory Tumor Sites. Cancer research, 2015; 75(12):2520-2529.
Wang et al. Targeted drug delivery to intestinal macrophages by bioactive nanovesicles released from grapefruit. Molecular therapy: the journal of the American Society of Gene Therapy. 2014; 22(3):522-534.
Webber et al. Extracellular vesicles as modulators of the cancer microenvironment, Seminars in cell & developmental biology. 2015; 40:27-34.
Xiang et al. Induction of myeloid-derived suppressor cells by tumor exosomes. Int J Cancer. 2009; 124(11):2621-2633.
Xiang et al. miR-155 promotes macroscopic tumor formation yet inhibits tumor dissemination from mammary fat pads to the lung by preventing EMT. Oncogene. 2011; 30(31):3440-3453.
Yang et al. Detection of tumor cell-specific mRNA and protein in exosome-like microvesicles from blood and saliva, PloS one. 2014; 9(11):e110641.
Yu et al. Tumor exosomes inhibit differentiation of bone marrow dendritic cells. Journal of immunology. 2007; 178(11):6867-6875.
Yue et al. The tetraspanins CD151 and Tspan8 are essential exosome components for the crosstalk between cancer initiating cells and their surrounding, Oncotarget. 2015; 6(4):2366-2384.

(56) References Cited

OTHER PUBLICATIONS

Zhang & Grizzle. Exosomes: a novel pathway of local and distant intercellular communication that facilitates the growth and metastasis of neoplastic lesions. The American journal of pathology. 2014; 184(1):28-41.
Zhang et al. Microenvironment-induced PTEN loss by exosomal microRNA primes brain metastasis outgrowth. Nature. 2015; 527(7576):100-104.
Zhuang et al. Treatment of brain inflammatory diseases by delivering exosome encapsulated anti-inflammatory drugs from the nasal region to the brain. Molecular therapy: the journal of the American Society of Gene Therapy, 2011; 19(10): 1769-1779.
Alizadeh et al. "Induction of anti-glioma natural killer cell response following multiple low-dose intracerebral CpG therapy," Clin Cancer Res, 2010, vol. 16, pp. 3399-3408.
Berquin et al. "Multi-targeted therapy of cancer by omega-3 fatty acids," Cancer Lett, 2008, vol. 269, pp. 363-377.
Bhatt et al. "Synthesis and in vivo antitumor activity of poly(I-glutamic acid) conjugates of 208-camptothecin," J Med Chem., 2003, vol. 46, pp. 190-193.
Bidros et al. "Novel drug delivery strategies in neuro-oncology," Neurotherapeutics, 2009, vol. 6, pp. 539-546.
Blaskovich. Discovery of JSI-124, a selective janus kinase signal transducer and activator of transcription 3 signaling pathway inhibitor with potent antitumor activity against human and murine cancer cells in mice, Can Res, 2003, 63, 1270-1279.
Chaudhury & Das (2015). Folate receptor targeted liposomes encapsulating anti-cancer drugs. Current pharmaceutical biotechnology 16: 333-343.
Chen et al. Enhanced cellular uptake of folic acid-conjugated PLGA-PEG nanoparticles loaded with vincristine sulfate in human breast cancer. Drug Dev Ind Pharm 37, 1339-1346, doi:10.3109/03639045.2011.575162 (2011).
Moorthi et al. Nanotherapeutics to overcome conventional cancer chemotherapy limitations. J Pharm Pharm Sci 14, 67-77 (2011).
Cho et al. "Therapeutic nanoparticles for drug delivery in cancer," Clin. Cancer Res., 2008, vol. 14:(5), pp. 1310-1316.
Cho. MicroRNAs as therapeutic targets and their potential applications in cancer therapy. Expert opinion on therapeutic targets. 2012; 16(8):747-759.
Dai et al. "Phase I clinical trial of autologous ascites-derived exosomes combined with GM-CSF for colorectal cancer," Mol. Ther., 2008, vol. 16(4), pp. 782-790.
Dauty et al. (2002). Intracellular delivery of nanometric DNA particles via the folate receptor. Bioconjugate chemistry 13: 831-839.
Dhawan et al. (2013). Targeting folate receptors to treat invasive urinary bladder cancer. Cancer research 73: 875-884.
Escudier et al. "Vaccination of metastatic melanoma patients with autologous dendritic cell (DC) derived-exosomes: results of the first phase I clinical trial," J. Transl. Med., 2005, vol. 3(1), p. 10.
Franzen, S (2011). A comparison of peptide and folate receptor targeting of cancer cells: from single agent to nanoparticle. Expert opinion on drug delivery 8: 281-298.
Friedman et al. "Curcumin analogues exhibit enhanced growth suppressive activity in human pancreatic cancer cells," Anticancer Drugs, 2009, vol. 20(6), pp. 444-449.
Geng et al., MicroRNA-192 suppresses liver metastasis of colon cancer, Oncogene, vol. 33, pp. 5332-5340. (Year: 2014).
Hirsjarvi, S., Passirani, C. & Benoit, J. P. Passive and active tumour targeting with nanocarriers. Curr Drug Discov Technol 8, 188-196 (2011).
Humphreys K J, McKinnon R A and Michael M Z. miR-18a inhibits CD042 and plays a tumour suppressor role in colorectal cancer cells. PloS one. 2014; 9(11):e112288.
International Preliminary Report on Patentability corresponding to International Patent Application No. PCT/US2011/023747 dated Aug. 7, 2012.
Jiang, H, Wang, P, Li, X, Wang, Q, Deng, Z B, Zhuang, X et al. (2014). Restoration of miR17/20a in solid tumor cells enhances the natural killer cell antitumor activity by targeting Mekk2. Cancer immunology research 2: 789-799.
Khar, Induction of stress response renders human tumor cell lines resistant to curcumin-mediated apoptosis, Cell Stress and Chaperones, 2001, 6, 4, 368-376.
Kolhatkar, R., Lote, A. & Khambati, H. Active tumor targeting of nanomaterials using folic acid, transferrin and integrin receptors. Curr Drug Discov Technol 8, 197-206 (2011).
Kularatne, S A, and Low, P S (2010). Targeting of nanoparticles: folate receptor. Methods in molecular biology 624: 249-265.
Kusmartsev et al. "Immature myeloid cells and cancer-associated immune suppression," Cancer Immunol Immunother, 2002, vol. 51, pp. 293-298.
Kusmartsev et al. "Inhibition of myeloid cell differentiation in cancer: the role of reactive oxygen species," J Leukoc Biol, 2003, vol. 74, pp. 186-196.
Liu, J., Kolar, C., Lawson, T. A. & Gmeiner, W. H. Targeted drug delivery to chemoresistant cells: folic acid derivatization of FdUMP[10] enhances cytotoxicity toward 5-FU-resistant human colorectal tumor cells. J Org Chem 66. 5655-5663 (2001).
Marchetti, C, Palaia, I, Giorgini, M, De Medici, C, Iadarola, R, Vertechy, L et al. (2014). Targeted drug delivery via folate receptors in recurrent ovarian cancer: a review. OncoTargets and therapy 7: 1223-1236.
Markman, M., "Pegylated liposomal doxorubicin in the treatment of cancer of the breast anc ovary," Expert Opin. Pharmacother, 2006, vol. 7, pp. 1469-1474.
Mayhew, E.G. et al. 1987. Effects of liposome-entrapped doxorubicin on liver metastases of mouse colon carcinomas 26 and 38. Journal of the National Cancer Institute 78(4): 707-713. specif. p. 707, 708.
Murakami et al. "Targeting NOX, INOS and COX-2 in inflammatory cells: chemoprevention using food phytochemicals," Int J Cancer, 2007, vol. 121, pp. 2357-2363.
Narayanan et al. "Liposome-encapsulation of curcumin and resveratrol in combination reduced prostate cancer incidence in PTEN knock-out mice," Int. J. Cancer, 2009, vol. 125, pp. 1-8.
Nukolova, N. V., Oberoi, H. S., Cohen, S. M., Kabanov, A. V. & Bronich, T. K. Folate-decorated nanogels for targeted therapy of ovarian cancer. Biomaterials 32, 5417-5426, doi:10.1016/j.biomaterials. 2011.04.006 (2011).
Qian B Z, Li J, Zhang H, Kitamura T, Zhang J, Campion L R, Kaiser E A, Snyder L A and Pollard J W. CCL2 recruits inflammatory monocytes to facilitate breast-tumour metastasis. Nature. 2011; 475(7355):222-225.
Raimondo S, Naselli F, Fontana S, Monteleone F, Lo Dico A, Saieva L et al. Citrus limon-derived nanovesicles inhibit cancer cell proliferation and suppress CML xenograft growth by inducing TRAIL-mediated cell death. Oncotarget. 2015; 6(23):19514-27.
Reymond, N., D'Agua, B.B. & Ridley, A.J. Crossing the endothelial barrier during metastasis. Nature reviews.Cancer 13, 858-870 (2013).
Roger E, Lagarce F, Garcion E, Benoit JP. Lipid nanocarriers improve paclitaxel transport throughout human intestinal epithelial cells by using vesicle-mediated transcytosis. J Control Release. 2009;140(2):174-181. Prepublished on Aug. 25, 2009 as DOI 80168-3659(09)00548-3 [pii]10.1016/j.jconrel.2009.08.010.
Rosenthal et al. "Phase IV study of liposomal daunorubicin (DaunoXome) in AIDS-related kaposi sarcoma," Am_J_Clin_Oncol., 2002, vol. 25, pp. 57-59.
Ryan A E, Colleran A, O'Gorman A, O'Flynn L, Pindjacova J, Lohan P, O'Malley G, Nosov M, Mureau C and Egan L J. Targeting colon cancer cell NF-kappaB promotes an anti-tumour M1-like macrophage phenotype and inhibits peritoneal metastasis. Oncogene. 2015; 34(12):1563-1574.
Scott et al. "Emerging roles for phospholipase A2 enzymes in cancer," Biochimie, 2010, vol. 92:(6), pp. 620-626.
Shedden, K. et al. 2003. Expulsion of small molecules in vesicles shed by cancer cells: association with gene expression and chemosensitivity profiles. Cancer Research 63: 4331-4337. specif. pp. 4331, 4335.
Taheri, A. , Atyabi, F., Salman Nouri, F. et al. Nanoparticle sof Conjugated Methotrexate-Human Serum Albumin: Preparation and Cytotoxicity Evaluations. Journal of Nanomaterials 2011 ;2011.

(56) References Cited

OTHER PUBLICATIONS

United States Patent and Trademark Office, International Search Report and Written Opinion issued in corresponding Application No. PCT/US15/25337, dated Jul. 1, 2015.

United States Patent and Trademark Office, International Search Report and Written Opinion issued in corresponding Application No. PCT/US16/040710, dated Sep. 23, 2016.

USPTO/ISA, International Search Report and Written Opinion in corresponding international application PCT/US2011/023747, completed Mar. 22, 2011.

Van den Eynden G G, Majeed AW, Illemann M, Vermeulen P B, Bird N C, Hoyer-Hansen G, Eefsen R L, Reynolds A R and Brodt P. The multifaceted role of the microenvironment in liver metastasis: biology and clinical implications. Cancer research. 2013; 73(7):2031-2043.

Van Niel et al. "Exosomes: A common pathway for a specialized function," J _ Biochem., 2006, vol. 140(1), pp. 13-21.

Wolfers et al. "Tumor-derived exosomes are a source of shared tumor rejection antigens for CTL cross-priming," Nat Med., 2001, vol. 7(3), pp. 297-303.

Xiang, X. et al. TLR2-mediated expansion of MDSCs is dependent on the source of tumor exosomes. Am J Pathol 177, 1606-1610, doi:10.2353/ajpath.2010.100245 (2010).

Xu S, Wei J, Wang F, Kong L Y, Ling X Y, Nduom E, Gabrusiewicz K, Doucette T, Yang Y, Yaghi N K, Fajt V, Levine J M, Qiao W, Li X G, Lang F F, Rao G et al. Effect of miR-142-3p on the M2 macrophage and therapeutic efficacy against murine glioblastoma. Journal of the National Cancer Institute. 2014; 106(8).

Xue et al., Solid lipid-PEI hybrid nanocarrier: An integrated approach to provide extended, targeted, and safer siRNA therapy of prostate cancer in an all-in-one manner, ACS Nano, vol. 5, pp. 7034-7047. (Year: 2011).

Yagi et al. "A nanoparticle system specifically designed to deliver short interfering RNA inhibits tumor growth in vivo," Cancer Res, 2009, vol. 69(16), pp. 6531-6538.

Yang F, Zhang W, Shen Y and Guan X. Identification of dysregulated microRNAs in triple-negative breast cancer (review). International journal of oncology. 2015; 46(3):927-932.

Zhang H-G, Curcumin reverses breast tumor exosomes mediated immune suppression of NK cell tumor cytotoxicity, 2007, Biochimica Biophysica Acta, 1773, 1116-1123.

\* cited by examiner

RNA SEQUENCING

| Gene | Description | Exosome | HG-NV |
|---|---|---|---|
| Rtn4r | reticulon 4 receptor | 0 | 24 |
| Sfta2 | surfactant associated 2 | 0 | 21 |
| Ifitm1 | interferon induced transmembrane protein 1 | 0 | 15 |
| Comtd1 | catechol-O-methyltransferase domain containing 1 | 0 | 12 |
| Ifna15 | interferon alpha 15 (predict) | 0 | 8 |
| Hba-a1 | hemoglobin alpha adult chain 1 | 0 | 8 |
| Il1f8 | interleukin 1 family member 8 | 0 | 8 |
| Ifnb1 | interferon beta 1 fibroblast | 0 | 7 |
| Ayp1 | activator of yeast meiotic promoters 1 | 0 | 7 |
| Gm20611 | predicted gene 20611 | 0 | 11 |
| Hprt | hypoxanthine guanine phosphoribosyl transferase | 66 | 0 |
| Tceb2 | transcription elongation factor B (SIII) polypeptide 2 | 58 | 0 |
| Ifitm2 | interferon induced transmembrane protein 2 | 58 | 0 |
| Slpi | secretory leukocyte peptidase inhibitor | 140 | 3 |
| Npm1 | nucleophosmin 1 | 1600 | 52 |
| Bag5 | BCL2-associated athanogene 5 | 29 | 0 |
| Itgb1 | integrin beta 1 (fibronectin receptor beta) | 49 | 1 |
| Rab2a | RAB2A member RAS oncogene family NM_021518.3 | 17 | 0 |
| Malat1 | metastasis associated lung adenocarcinoma transcript 1 | 342 | 16 |
| Kdm5c | Kdm5c adjacent non-coding transcript | 31 | 0 |

FIG. 2E

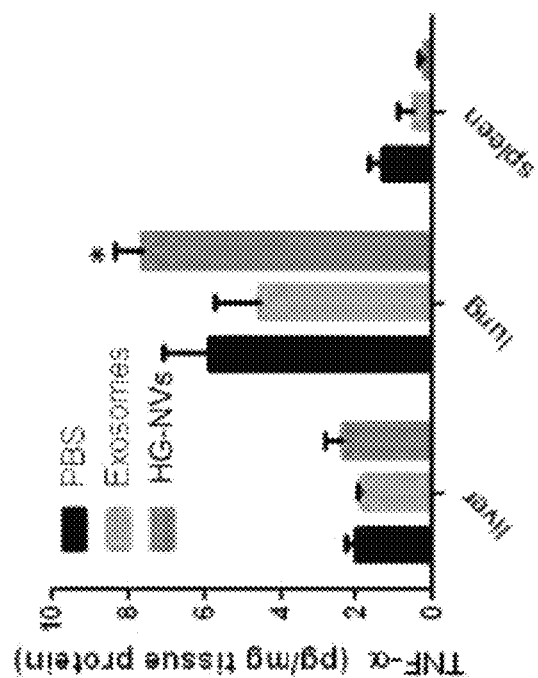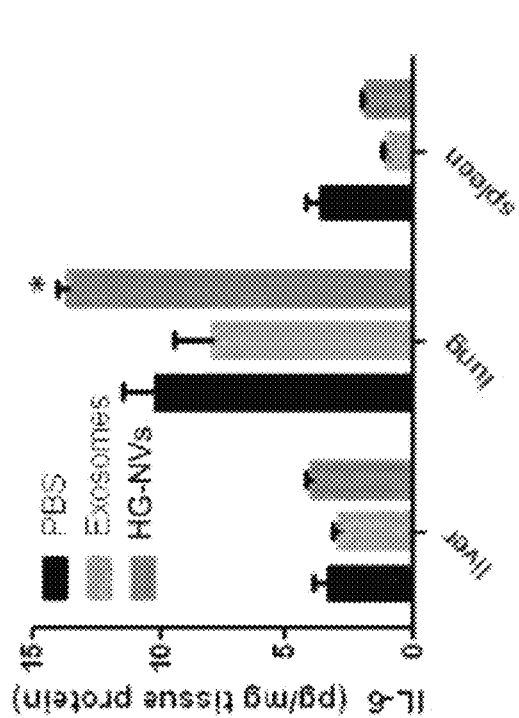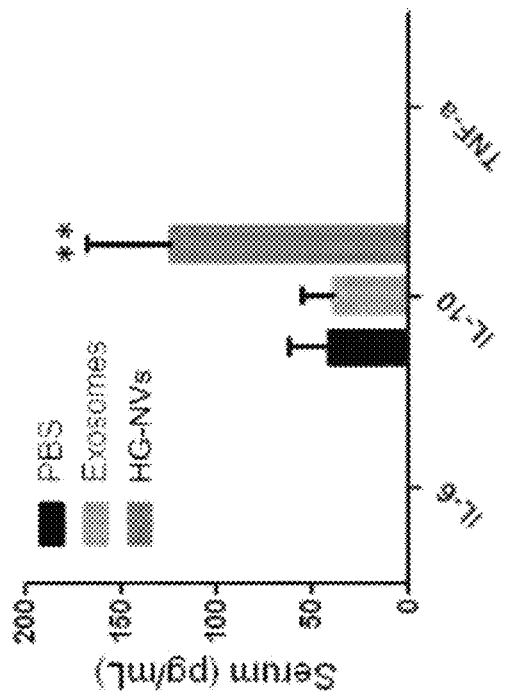
FIG. 6C

Mouse Cytokine Array Panel A Transparency Overlay

Part # 607584

| Location | Analyte | Location | Analyte |
|---|---|---|---|
| A1 | Positive Control | C8 | IL-12p70 |
| A2 | Blank | C9 | IL-16 |
| A3 | Blank | C10 | IL-17 |
| A4 | Blank | C11 | IL-23 |
| A5 | Blank | C12 | IL-27 |
| A6 | Blank | D1 | IP-10/CXCL10 |
| A7 | Blank | D2 | I-TAC/CXCL11 |
| A8 | Blank | D3 | KC |
| A9 | Blank | D4 | M-CSF |
| A10 | Blank | D5 | JE/MCP-1/CCL2 |
| A11 | Blank | D6 | MCP-5/CCL12 |
| A12 | Positive Control | D7 | MIG/CXCL9 |
| B1 | BLC/BCA-1/CXCL13 | D8 | MIP-1 alpha/CCL3 |
| B2 | C5a | D9 | MIP-1 beta/CCL4 |
| B3 | G-CSF | D10 | MIP-2 |
| B4 | GM-CSF | D11 | RANTES/CCL5 |
| B5 | I-309/CCL1 | D12 | SDF-1/CXCL12 |
| B6 | Eotaxin/CCL11 | E1 | TARC/CCL17 |
| B7 | ICAM-1 | E2 | TIMP-1 |
| B8 | IFN-gamma | E3 | TNF-alpha |
| B9 | IL-1 alpha | E4 | TREM-1 |
| B10 | IL-1 beta | E5 | Blank |
| B11 | IL-1ra | E6 | Blank |
| B12 | IL-2 | E7 | Blank |
| C1 | IL-3 | E8 | Blank |
| C2 | IL-4 | E9 | Blank |
| C3 | IL-5 | E10 | Blank |
| C4 | IL-6 | E11 | Blank |
| C5 | IL-7 | E12 | Blank |
| C6 | IL-10 | F1 | Positive Control |
| C7 | IL-13 | | |

FIG. 8

NANOVESICLES, METHODS, AND SYSTEMS FOR DIAGNOSIS AND PROGNOSIS OF CANCER

RELATED APPLICATIONS

This application claims priority from U.S. Provisional Application Ser. No. 62/482,754, filed Apr. 7, 2017, the entire disclosure of which is incorporated herein by this reference.

GOVERNMENT INTEREST

This invention was made with government support under grant numbers R01AT008617 and UH2TR000875 awarded by the National Institutes of Health. The government has certain rights in the invention.

TECHNICAL FIELD

The presently-disclosed subject matter generally relates to nanovesicles, methods, and systems for diagnosis and prognosis of cancer. In particular, certain embodiments of the presently-disclosed subject matter relate to methods for diagnosis and prognosis of cancer in a subject based on the isolation and identification of a sub-population of nanovesicles in a biological sample obtained from a subject.

BACKGROUND

Intercellular communication is a hallmark of multicellular organisms. Recently, extracellular microvesicles (EVs) have been recognized as one of the major mechanisms for intercellular communication. EVs have been isolated from diverse body fluids, including semen, blood, urine, saliva, breast milk, amniotic fluid, ascites fluid, cerebrospinal fluid, and bile. However, EVs include more than one type, and whether a particular subpopulation of EVs is the predominant type in a specimen or upon isolation is not known.

The recent increase of EV research has strongly emphasized the application of these nanovesicles as diagnostic and treatment monitoring tools. Utilizing the most abundant EVs circulated in the body fluid will be the best resource for such applications. A primary class of EVs is thought to be exosomes. However, current protocols used for isolation of exosomes do not aid in determining if exosomes are the most abundant EVs in a sample. Moreover, exosomes carry various proteins, bioactive lipids and genetic information to alter the phenotype and function of recipient cells. Thus, exosomes have been implicated in numerous biological and pathological processes. Like other EVs, exosomes are heterogeneous in size (50-150 nm) and in function, and are released from many cell types. The heterogeneity of exosomes makes it challenging to determine if a specific sub-population of exosomes is the dominate subpopulation or phenotype in a clinical specimen. Current strategies for characterizing exosomes are limited to multiple in vitro manipulations for isolation and purification, followed by analytic approaches that generate data that may not represent what takes place in vivo. Therefore, the ability to identify, isolate, and molecularly characterize EVs with minimal in vitro manipulation is urgently needed and could be highly beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes nanovesicles, methods, and systems for diagnosis and prognosis of cancer. In particular, certain embodiments of the presently-disclosed subject matter include methods for diagnosis and prognosis of cancer in a subject based on the isolation and identification of a sub-population of nanovesicles in a biological sample obtained from a subject. In some embodiments, a method for diagnosis or prognosis of a cancer in a subject is provided that comprises the steps of: providing a biological sample from a subject; isolating one or more nanovesicles from the biological sample, where the one or more nanovesicles have a diameter of about 8-12 nm, a charge of about −10±5 mV, one or more RNA molecules selected from Table 2b, one or more peptides selected from Tables 3b or 3d, one or more lipids selected from Table 4, or combinations thereof; determining the amount in the biological sample of the one or more nanovesicles; and comparing the amount of the one or more nanovesicles in the sample, if present, to a control level of the one or more nanovesicles. The subject can then be diagnosed as having a cancer or a risk thereof if there is a measurable difference in the amount of the one or more nanovesicles in the sample as compared to the control level. In some embodiments, the cancer is selected from the group consisting of breast cancer, colon cancer, lung cancer, and liver cancer. In some embodiments, the cancer is a metastatic cancer. In some embodiments, a treatment for the cancer is selected or modified based on the determined amount of the one or more nanovesicles.

With respect to the biological sample used to isolate the one or more nanovesicles, in some embodiments, the biological sample comprises blood, plasma, or serum. In some embodiments, the biological sample includes one or more tumor cells, such as, in certain embodiments, one or more tumor cells from a tumor biopsy.

In some embodiments, isolating the one or more exosomes from biological sample comprises an additional step of depleting exosomes from the biological sample prior to isolating the one or more nanovesicles. In some embodiments, in addition to isolating the nanovesicles, the methods described herein further include a step of determining an amount of the one or more peptides selected from Table 3b or 3d in the one or more nanovesicles using mass spectrometry (MS) analysis, immunoassay analysis, or both. In some embodiments, the methods further include a step of determining an amount in the sample of one or more RNA molecules selected from Table 2b in the one or more nanovesicles using a probe or primer specific for the one or more RNA molecules. In some embodiments, an amount in the sample of one or more lipids selected from Table 4 in the one or more nanovesicles is determined using mass spectrometry (MS) analysis.

Further provided, in some embodiments of the presently-disclosed subject matter are methods for identifying tumor metastasis in a subject. In some embodiments, a method for identifying tumor metastasis in a subject is provided that comprises the steps of: providing a biological sample including one or more tumor cells from the subject; fractionating the biological sample to obtain a fraction including one or more exosomes and one or more nanovesicles of the presently-disclosed subject matter, the nanovesicles having a diameter of about 8-12 nm; isolating the one or more nanovesicles from the fraction including the one or more nanovesicles; determining the amount in the biological sample of the one or more nanovesicles; and comparing the amount of the one or more nanovesicles in the biological sample, if present, to a control level of the one or more nanovesicles, wherein the subject is diagnosed as having a tumor metastasis, or a risk thereof, if there is a measurable difference in the amount of the one or more nanovesicles in the sample as compared to the control level.

Further features and advantages of the presently-disclosed subject matter will become evident to those of ordinary skill in the art after a study of the description, figures, and non-limiting examples in this document.

BRIEF DESCRIPTION OF THE DRAWINGS

(FIG. 1A) graphs showing size distribution of the nanovesicles where 800 μl of samples were added to a cuvette and the size distribution was determined using a Zetasizer Nano ZS; (FIG. 1B-1C) graphs and images showing size distribution of banded 4T1 samples from sucrose gradient ultracentrifugation visualized by the Zetasizer Nano ZS (FIG. 1B) and by electro-microscopy (FIG. 1C); and (FIG. 1D) a graph showing the surface Zetapotential of the particles determined using the Zetasizer Nano ZS.

FIGS. 2A-2I include images and graphs showing the characterization of tumor cell derived HG-NV RNA, including: (FIG. 2A) an image showing, after electrophoresis on a 12% polyacrylamide gel, HG-NV RNA pretreated with/without RNase, stained with ethidium bromide, and visualized using a UVP PhotoDoc-It™ Imaging System; (FIG. 2B) a graph showing total RNA from HG-NVs and exosomes and quantified using Nanodrop spectrophotometry to measure absorbance at 260 nm, and expressed as ng/μg of microvesicle protein, where error bars represent standard deviation (±SD) (**p<0.01), and where "N" represents the number of samples analyzed; (FIG. 2C) an XY-scatter plot showing the log 2 transformed read counts of RNA sequencing data between exosomes (X-axis) and HG-NVs (Y-axis) purified from 4T1 cells, where the red dots represent RNAs that are higher in HG-NVs than in exosomes (differential expression of log 2 value>2), the green dots represent the RNAs that are higher in exosomes than in HG-NVs, and the blue dots represent similar levels of RNAs detected in exosomes and HG-NVs; (FIG. 2D) a venn diagram showing comparative RNA overlap of the HG-NVs and exosomes; (FIG. 2E) a schematic diagram showing listed RNAs randomly and that are predominately presented in the HG-NVs (upper panel) or vice versa (bottom panel); (FIG. 2F) real-time PCR quantitation of RNAs isolated from HG-NVs and exosomes of 4T1 cell line (left panel) or plasma of 3-week 4T tumor bearing mice (right panel), where fold changes of HG-NV RNA were expressed as the levels of HG-NV RNA/exosomes RNA, *P<0.05 and **P<0.01 (two-tailed t-test), and where data are representative of three independent experiments (n=3 error bars, SEM); (FIG. 2G) a graph showing real-time PCR quantitation of RNAs isolated from peripheral blood HG-NVs of naïve mice, 21 day 4T1 tumor bearing mice, and 24 h LPS challenged mice, where fold changes of HG-NV RNA were expressed as the levels of HG-NV RNA from 4T1 tumor bearing mice or LPS challenged mice/PBS treated mice (naïve mice), *P<0.05 and **P<0.01 (two-tailed t-test), and where data are representative of two independent experiments (n=5 error bars, SEM); (FIG. 2H) a schematic diagram showing approximately 300 RNAs that are 5-fold or above lower in HG-NVs than in exosomes and that were selected and analyzed with ingenuity pathway analysis (IPA), where the pathways that are regulated by HG-NV derived RNAs are boxed; and (FIG. 2I) a schematic diagram and graph showing listed RNAs isolated from MDA-MB-231HG-NV and exosomes that were quantified using real-time PCR, *P<0.05 (two-tailed t-test), where data are representative of three independent experiments (n=3 error bars, SEM.).

(FIG. 3A) an image showing, after electrophoresis on an 8% SDS polyacrylamide gel, a representative gel stained with Coomassie Blue and scanned using an Odyssey Imaging System; (FIG. 3B) a venn diagram (left panel) showing comparative protein overlap of the HG-NVs and exosomes and an image showing TSG101, CD63, albumin, and GAPDH expression analyzed by Western blotting; (FIGS. 3C-3D) graphs showing the results of an analysis where approximately 200-300 genes that are highly expressed in 4T1 (FIG. 3C) or MDA-MB-231 (FIG. 3D) HG-NVs or exosomes were analyzed with ingenuity path analysis (IPA), where the graphs show the top ten canonical pathways that are regulated by 4T1 or MDA-MB-231HG-NV and exosome derived genes, and where the x-axis represents −log(p-value), where multiple-testing corrected p-values were obtained using the Benjamini Hochberg method and represent the significant enrichment of uploaded genes in the functional and canonical pathways shown in Y-axis.

FIG. 4A is a representative image of a chromatography plate scanned using an Odyssey Scanner, where the results represent one of four independent experiments. FIG. 4B includes pie charts with a summary of the putative lipid species in 4T1 exosomes and HG-NVs, reported as percent of total GELN lipids (PS: Phosphatidylserine; PI: Phosphatidylinositol; PE: Phosphatidylethanolamines; PC: Phosphatidylcholines; SM/DSM: Mono/Di/N-(dodecanoyl)-sphing-4-enine-1-phosphocholin).

(FIG. 5A) images showing the imaging of DiR dye labeled 4T1 exosomes and HG-NV administered intravenously (i.v.) to mice (Left panel) and in vivo distribution of DiR dye labeled 4T1 exosomes and HG-NVs determined by scanning (Odyssey scanner) each organ of mice i.v. injected with DiR dye labeled 4T1 exosomes and HG-NVs (right panel); (FIG. 5B) graphs showing, at 16 h after PKH67 florescent dye labeled 4T1 HG-NVs were administrated intravenously, percentages of lung and liver leukocytes quantitatively analyzed by FACS; (FIG. 5C) images and graphs showing inflammatory cytokine expression in HG-NV and exosome stimulated bone marrow derived macrophages (top panel), immature myeloid cells (middle panel) and dendritic cells (bottom panel) determined using the Proteome Profiler from R&D systems, where each dot represents a cytokine detected by a capture antibody and printed in duplicate on the membrane, and where the signal intensity of dots on the developed X-ray film was quantified using the LI-COR imaging system and analyzed with LI-COR® Image Studio™ Lite Software V3.1.

FIGS. 6A-6E include graphs and images showing that tumor cell derived HG-NVs promote tumor progression, including: (FIG. 6A) growth curves of 4T1 tumors by orthotopical injection of 4T1 cells into the mammary fat pads in BALB/c mice (5 mice per group) tail-vein injected with 4T1 exosomes or HG-NVs (40 μg/mouse), with a schematic representation of the injection schedule (left panel), where error bars represent standard deviation (±SD) (two-way ANOVA; **$p<0.01$); (FIG. 6B) representative photographs and graphs showing the H&E stained tissue of 4T1 tumor metastases per field of sectioned lung (upper panel) and liver (bottom panel) of 30-day tumor bearing mice, where the results are based on three independent experiments (n=5), and where the means of the number of metastatic foci/field are shown ($P<0.001$); (FIG. 6C) graphs showing, before mice were sacrificed at day 30 after tumor cells were injected, the levels of IL-6 and TNFα in the lysates from each tissue as labeled in the figure quantitatively analyzed using an ELISA, and where levels of IL-6, IL-10 and TNFα in the sera were also quantitatively analyzed using an ELISA, data presented as the mean±S.E.M.; *$p<0.05$, **$p<0.01$; (FIG. 6D) growth curves of CT26 tumors after subcutaneous injection of CT26 cells in BALB/c mice (5 mice per group) which were intra-tumorally injected with CT26 exosomes, HG-NV (100 μg/mouse), and PBS as a control, along with a schematic representation of the injection schedule (left panel), where error bars represent standard deviation (±SD) (two-way ANOVA; *$p<0.05$, ***$p<0.001$); (FIG. 6E) a representative photograph and graph showing the H&E stained tissue of CT26 micro-tumors per field of sectioned liver at low magnification (upper panel) and higher magnification (bottom panel) of 21-day tumor bearing mice.

FIG. 8 is a table and a schematic showing selected capture antibodies as listed (left panel) spotted in duplicate on nitrocellulose membranes, where the positive signals seen on developed film can be quickly identified by placing the transparency overlay template on the array image and aligning it with the pairs of reference spots in three corners of each array.

DESCRIPTION OF EXEMPLARY EMBODIMENTS

Figure 1A:
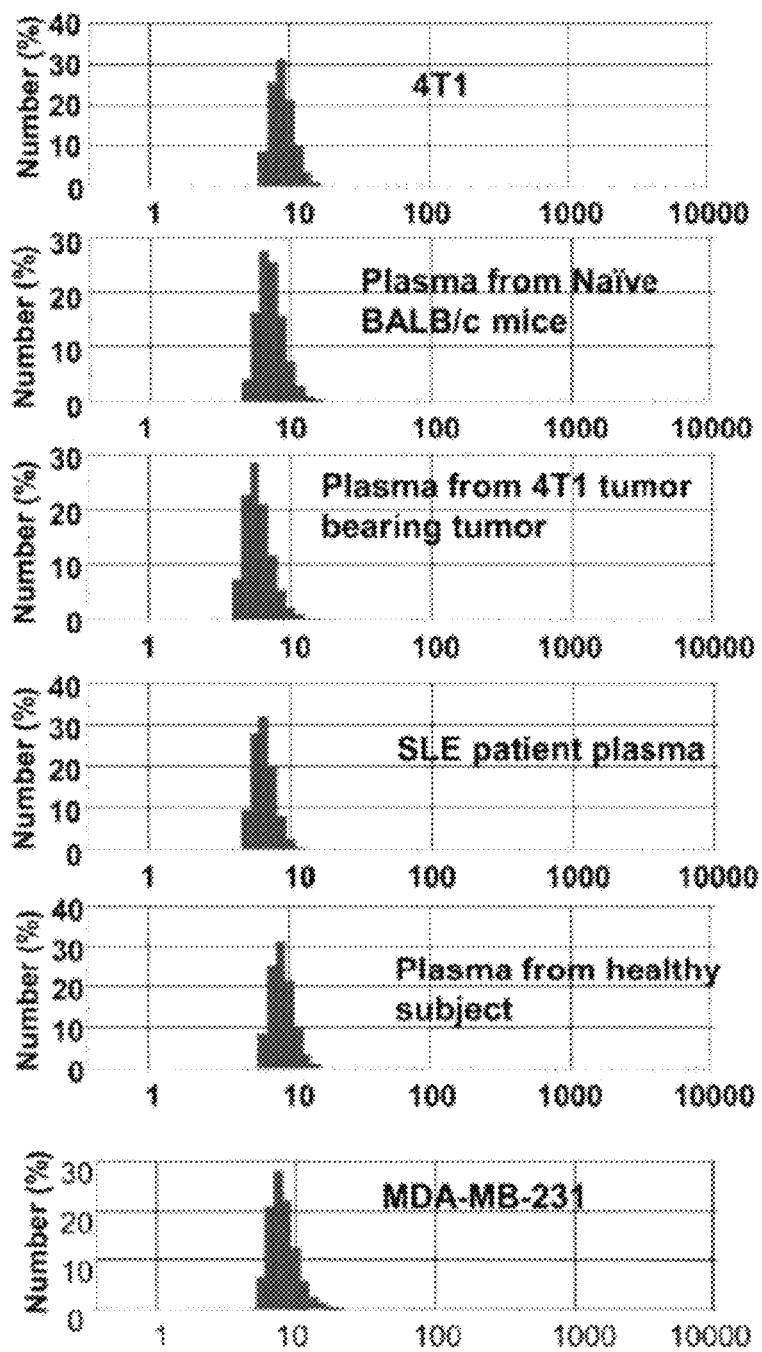
FIGS. 1A-1D include graphs and images showing the identification and characterization of the nanovesicles of the presently-disclosed subject matter, referred to herein as HG-NV, including.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist of" (closed), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, an identified fragment of a peptide (e.g., by mass spectrometry) is intended to encompass the fragment as well as the full-length peptide. As such, determining an amount of a biomarker in a sample can include determining an amount of the full-length biomarker polypeptide, modified variants, and/or fragments thereof.

The presently-disclosed subject matter is based, at least in part, on the discovery of a novel population of nanovesicles (referred to herein as HG-NVs) that, unlike other identified extracellular microvesicles (EVs) including exosomes (which cannot be detected using a nanosizer without concentration in vitro), are 8-12 nm in size and can be detected from blood and cell cultured supernatants without in vitro manipulations. In particular, HG-NVs released from mouse and human tumor cells were characterized. HG-NVs were found to have a number of unique characteristics in comparison with corresponding exosomes purified from identical samples. HG-NVs released from tumor cells were relatively homogenous in size; had specific RNAs induced in a disease dependent manner in a mouse breast tumor model and a LPS induced septic shock mouse model; and had higher percentages of phosphatidyl (PS) lipids. In combination with the feature that HG-NVs are a predominate set of EVs, and without wishing to be bound by any particular theory, it was believed that HG-NVs could be utilized as a better source for disease diagnosis. As such, the biological effect of HG-NVs on promoting tumor progression was further demonstrated in tumor metastasis. In this regard, it was determined that that the HG-NVs had increased diagnostic value that allowed the HG-NVs to be used as a non-invasive diagnostic and screening tool to detect stages of certain types of cancers, among other things.

The presently-disclosed subject matter includes nanovesicles, methods, and systems for diagnosis and prognosis of cancer. In particular, certain embodiments of the presently-disclosed subject matter include methods for diagnosis and prognosis of cancer in a subject based on the isolation and identification of a sub-population of nanovesicles in a biological sample obtained from a subject. In some embodiments, the presently-disclosed subject matter includes methods and systems for diagnosing cancer a subject, and for determining whether to initiate or continue prophylaxis or treatment of cancer in a subject, by isolating and/or identifying at least one nanovesicle as described herein in a biological sample from a subject.

In some embodiments of the presently-disclosed subject matter, a method for diagnosing cancer in a subject is provided. The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a nanovesicle (e.g., HG-NVs), the amount (including presence or absence) of which is indicative of the presence, severity, or absence of the condition.

Along with diagnosis, clinical disease prognosis is also an area of great concern and interest. It is important to know the stage and rapidity of advancement of the cancer in order to plan the most effective therapy. If a more accurate prognosis can be made, appropriate therapy, and in some instances less severe therapy for the patient can be chosen. Measurement of nanovesicle levels disclosed herein can be useful in order to categorize subjects according to advancement of the cancer who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of diagnostic nanovesicle or other biomarker levels disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not having a detectable amount of the nanovesicles or having a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a nanovesicle level of greater than a control level in some embodiments can signal that a subject is more likely to suffer from a cancer than subjects with a level less than or equal to the control level, as determined by a level of statistical significance. Additionally, a change in nanovesicle concentration from baseline levels can be reflective of subject prognosis, and the degree of change in nanovesicle levels can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a prognostic or diagnostic nanovesicle can be established, and the degree of change in the level of the indicator in a biological sample can simply be compared to the threshold degree of change in the level. A preferred threshold change in the level for nanovesicle of the presently-disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently-disclosed subject matter, multiple determination of one or more diagnostic or prognostic nanovesicles can be made, and a temporal change in the nanovesicles can be used to monitor the progression of disease and/or efficacy of appropriate therapies directed against the disease. In such an embodiment for example, one might expect to see a decrease or an increase in the nanovesicle(s) over time during the course of effective therapy. Thus, the presently-disclosed subject matter provides in some embodiments a method for determining treatment efficacy and/or progression of a cancer in a subject. In some embodiments, the method comprises determining an amount of the nanovesicles associated with cancer, i.e., the HG-NVs, in biological samples collected from the subject at a plurality of different time points and comparing the amounts of the nanovesicle(s) in the samples collected at different time points. For example, a first time point can be selected prior to initiation of a treatment and a second time point can be selected at some time after initiation of the treatment. One or more nanovesicle levels can be measured in each of the samples taken from different time points and qualitative and/or quantitative differences noted. A change in the amounts of the biomarker levels from the first and second samples can be correlated with determining treatment efficacy and/or progression of the disease in the subject.

The terms "correlated" and "correlating," as used herein in reference to the use of diagnostic and prognostic nanovesicles, refers to comparing the presence or quantity of the nanovesicles in a subject to its presence or quantity in subjects known to suffer from, or known to be at risk of, a given condition (e.g., a cancer); or in subjects known to be free of a given condition, i.e. "normal individuals". For example, a nanovesicle level in a biological sample can be compared to a level known to be associated with a specific type of cancer. The sample's nanovesicle level is said to have been correlated with a diagnosis; that is, the skilled artisan can use the nanovesicle level to determine whether the subject suffers from a specific type of cancer, and respond accordingly. Alternatively, the sample's nanovesicle level can be compared to a control marker level known to be associated with a good outcome (e.g., the absence of a cancer), such as an average level found in a population of normal subjects.

In certain embodiments, a diagnostic or prognostic nanovesicle is correlated to a condition or disease by merely its presence or absence. In other embodiments, a threshold level of a diagnostic or prognostic nanovesicle can be established, and the level of the nanovesicle in a subject sample can simply be compared to the threshold level.

As noted, in some embodiments, multiple determination of one or more diagnostic or prognostic nanovesicle can be made, and a temporal change in the marker can be used to determine a diagnosis or prognosis. For example, a diagnostic nanovesicle can be determined at an initial time, and again at a second time. In such embodiments, an increase in the marker from the initial time to the second time can be diagnostic of a particular type of cancer or a given prognosis. Likewise, a decrease in the nanovesicle from the initial time to the second time can be indicative of a particular type of cancer, or a given prognosis. Furthermore, the degree of change of one or more markers can be related to the severity of cancer and future adverse events, including metastasis, as describe further herein below.

The skilled artisan will understand that, while in certain embodiments comparative measurements can be made of the same diagnostic marker at multiple time points, one can also measure a given marker at one time point, and a second marker at a second time point, and a comparison of these markers can provide diagnostic information.

With regard to the step of providing a biological sample from the subject, the term "biological sample" as used herein refers to any body fluid or tissue potentially comprising the nanovesicles of the presently-disclosed subject matter. In some embodiments, for example, the biological sample can be a blood sample, a serum sample, a plasma sample, or sub-fractions thereof. In some embodiments, the biological sample comprises one or more tumor cells. In some embodiments, the biological sample comprises a tumor biopsy.

Turning now to the nanovesicles (i.e., the HG-NVs) identified and isolated in accordance with the presently-disclosed subject matter, in some embodiments and prior to isolating the one or more nanovesicles, any exosomes present in the biological sample are first depleted from the biological sample. For instance, in some embodiments, the step of isolating the nanovesicles of the presently-disclosed subject matter from the biological sample is accomplished by first subjecting the biological sample to consecutive centrifugation steps (e.g., 500×g, 2000×g, 3000×g, 1000×g) to remove cellular debris and larger vesicles. The supernatant from those initial centrifugation steps can then be subjected to an ultracentrifugation procedure (e.g., 100,000×g for 2 hr) to pellet exosomes. The supernatants from those ultracentrifugation procedures, which are exosome depleted and include the nanovesicles of the presently-disclosed subject matter, can then be removed, and the nanovesicles isolated by passing the exosome-depleted supernatant through an ultrafiltration module (e.g., a column that traps molecules greater than 500 kDa). The collected nanovesicles (e.g., that were retained on the column) can then be concentrated and subjected to procedures such as sucrose gradient centrifugation for further isolation and purification.

As described above, and by isolating the nanovesicles through procedures such as the foregoing, the nanovesicles described herein comprise a newly discovered population of vesicles that, unlike other identified extracellular microvesicles (EVs) including exosomes, have a number of characteristics that distinguish the presently-described nanovesicles from other vesicles, such as exosomes that typically have a greater diameter on the order of 50-150 nm. In some embodiments, the nanovesicles described for use herein have or can be characterized by having a diameter of about 8-12 nm, a charge of about −10±5 mV, one or more RNA molecules selected from Table 2b, one or more peptides selected from Tables 3b or 3d, one or more lipids selected from Table 4, or combinations thereof. In some embodiments, such RNA molecules, peptide, or lipids further serve as diagnostic or prognostic biomarkers. In this regard, in some embodiments and in addition to isolating the nanovesicles, the methods described herein further include a step of determining an amount of the one or more peptides selected from Table 3b or 3d in the one or more nanovesicles. In some embodiments, the methods further comprise a step of determining an amount in the sample of the one or more RNA molecules selected from Table 2b in the nanovesicles. In some embodiments, an amount in the sample of the one or more lipids selected from Table 4 in the nanovesicles is determined using mass spectrometry (MS) analysis. In some embodiments, by making use of the RNA, protein, or lipid profiles of the nanovesicles described herein, the RNA, protein, or lipid markers can be utilized as specific indicators of a stage of disease or as an indicator of health status (e.g., young versus aged). In certain embodiments, an RNA profile of a subject can be amplified (e.g., via PCR) to increase the sensitivity of a particular method.

With respect to the identification of the additional markers in the biological sample (i.e., in addition to the identification and isolation of the nanovesicles themselves), various methods known to those skilled in the art can be used to identify the peptides, RNA molecules, and/or lipids in the provided biological sample. In some embodiments, determining the amount of biomarkers in samples comprises using an RNA measuring assay to measure mRNA encoding biomarker polypeptides in the sample and/or using a protein measuring assay to measure amounts of biomarker polypeptides in the sample.

In certain embodiments, the amounts of biomarkers can be determined by probing for mRNA of the biomarker in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding biomarker polypeptides) immobilized on a substrate, e.g., array, or microarray, or quantitated by real time PCR (e.g., quantitative real-time PCR, such as available from Bio-Rad Laboratories, Hercules, Calif., U.S.A.). Because the probes to which the nucleic acid molecules of the sample are bound are known, the molecules in the sample can be identified. In this regard, DNA probes for one or more of the RNA molecules selected from Table 2b can be immobilized on a substrate and provided for use in practicing a method in accordance with the present subject matter.

With regard to determining amounts of biomarker peptides or lipids in samples, mass spectrometry and/or immunoassay devices and methods can be used to measure biomarker polypeptides in samples and mass spectrometry can readily be used to measure biomarker lipids in samples, although other methods are well known to those skilled in the art as well. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

In some embodiments, mass spectrometry (MS) analysis can be used alone or in combination with other methods (e.g., immunoassays) to determine the presence and/or quantity of the one or more biomarkers of interest (e.g., one or more peptides selected from Tables 3b or 3d, or one or more lipids selected from Table 4, or combinations thereof) in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated herein by this reference.

Although certain embodiments of the method only call for a qualitative assessment of the presence or absence of the one or more nanovesicles or other markers in the biological sample, other embodiments of the method call for a quantitative assessment of the amount of each of the one or more markers in the biological sample. Such quantitative assessments can be made, for example, using one of the above mentioned methods, as will be understood by those skilled in the art.

In certain embodiments of the method, a subject is identified having cancer upon identifying in a biological sample obtained from the subject one or more nanovesicles, RNA molecules, peptides, or lipids disclosed herein. In certain embodiments of the method, it can be desirable to include a control sample that is analyzed concurrently with the biological sample, such that the results obtained from the biological sample can be compared to the results obtained from the control sample. Additionally, it is contemplated that standard curves can be provided, with which assay results for the biological sample can be compared. Such standard curves present levels of protein marker as a function of assay units, i.e., fluorescent signal intensity, if a fluorescent signal is used. Using samples taken from multiple donors, standard curves can be provided for control levels of the one or more markers in normal tissue. It is further contemplated that the efficacy, accuracy, sensitivity, and/or specificity of the method can be enhanced by probing for multiple nanovesicles or other markers in the biological sample. For example, in certain embodiments of the method, the biological sample can be probed for one or more peptides selected from Tables 3b or 3d and/or one or more lipids selected from Table 4.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to identifying the approximate time from onset of the event, the presence and amount of salvageable tissue, the appropriateness of drug therapies, the effectiveness of various therapies, and identification of the subject's outcome, including risk of future events.

The analysis of markers can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

As mentioned above, depending on the embodiment of the method, identification of the one or more nanovesicles or other markers can be a qualitative determination of the presence or absence of the markers, or it can be a quantitative determination of the concentration of the markers. In this regard, in some embodiments, the step of identifying the subject as having cancer or a risk thereof requires that certain threshold measurements are made, i.e., the levels of the one or more nanovesicles in the biological sample exceed control level. In certain embodiments of the method, the control level is any detectable level of the nanovesicles or other markers. In other embodiments of the method where a control sample is tested concurrently with the biological sample, the control level is the level of detection in the control sample. In other embodiments of the method, the control level is based upon and/or identified by a standard curve. In other embodiments of the method, the control level is a specifically identified concentration, or concentration range. As such, the control level can be chosen, within acceptable limits that will be apparent to those skilled in the art, based in part on the embodiment of the method being practiced and the desired specificity, etc.

With respect to the cancer diagnosed in accordance with the presently-disclosed subject matter, the term "cancer" is used herein to refer to all types of cancer or neoplasm or malignant tumors found in animals, including leukemias, carcinomas, melanoma, and sarcomas. Examples of cancers are cancer of the brain, bladder, breast, cervix, colon, head and neck, kidney, lung, non-small cell lung, mesothelioma, ovary, prostate, sarcoma, stomach, uterus and Medulloblastoma. In some embodiments, the cancer is selected from the group consisting of breast cancer, colon cancer, lung cancer, and liver cancer. In some embodiments, the cancer is a metastatic cancer as the nanovesicles described herein have been found to be involved in the promotion of tumor progression in a subject.

Further provided, in some embodiments of the presently-disclosed subject matter methods and assays for identifying tumor metastasis in a subject. In some embodiments, a method for identifying tumor metastasis in a subject is provided that comprises the steps of: providing a biological sample including one or more tumor cells from the subject; fractionating the biological sample to obtain a fraction including one or more exosomes and one or more nanovesicles of the presently-disclosed subject matter, the nanovesicles having a diameter of about 8-12 nm; isolating the one or more nanovesicles from the fraction including the one or more nanovesicles; determining the amount in the biological sample of the one or more nanovesicles; and comparing the amount of the one or more nanovesicles in the biological sample, if present, to a control level of the one or more nanovesicles, wherein the subject is diagnosed as having a tumor metastasis, or a risk thereof, if there is a measurable difference in the amount of the one or more nanovesicles in the sample as compared to the control level.

Still further provided, in some embodiments, is a composition comprising a nanovesicle having a characteristic selected from the group consisting of: a diameter of about 8-12 nm; a charge of about −10±5 mV; one or more RNA molecules selected from Table 2b; one or more peptides selected from Tables 3b or 3d; one or more lipids selected from Table 4; an increased percentage of phosphatidylserine; and combinations thereof. In some embodiments, an isolated nanovesicle is provided that has a characteristic selected from the group consisting of: a diameter of about 8-12 nm; a charge of about −10±5 mV; one or more RNA molecules selected from Table 2b; one or more peptides selected from Tables 3b or 3d; one or more lipids selected from Table 4; an increased percentage of phosphatidylserine; and combinations thereof.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Material and Methods for Examples 1-5

Isolation of HG-NV.

Figure 7:
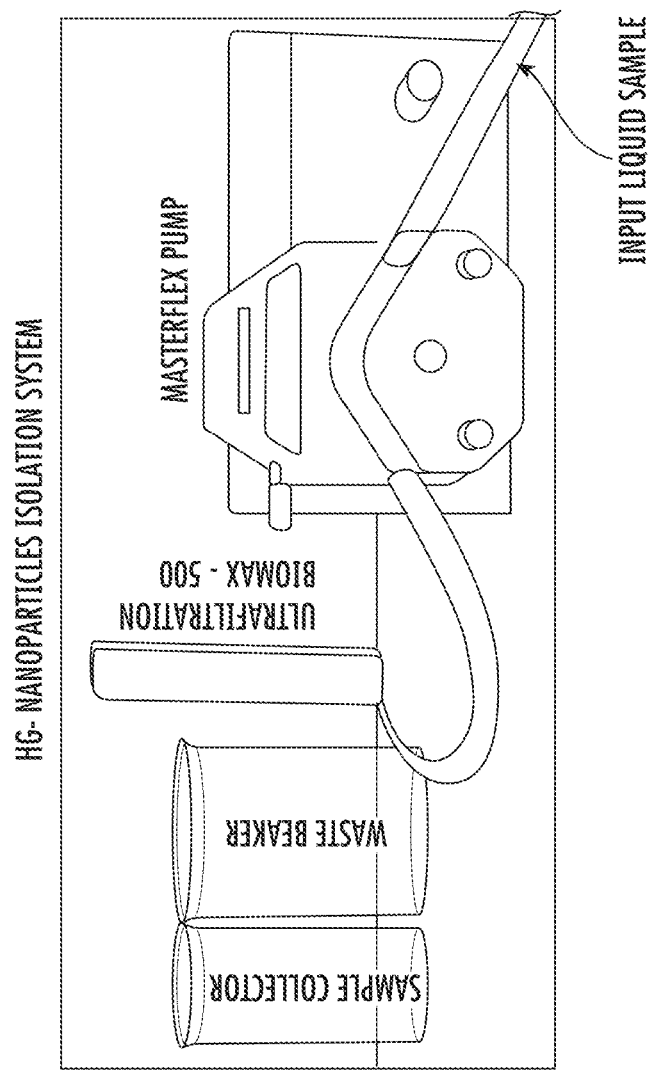
FIG. 7 is an image showing the workstation setup for HG-NV isolation, where the sample is continually pumped through the plastic tube using a pressure-regulated pump into the Biomaxx500 column, where the molecules >500 kDas are retained and collected in the "sample collector", and the molecules<500 kDas pass through the column and are collected in the "Waste Beaker."

To characterize the HG-NVs, other subset populations of EVs were eliminated from the samples. To do this, the supernatants were saved after exosomes had been isolated using a protocol described below in "Exosome isolation." The isolation and concentration of HG-NVs (HG-nanovesicle isolation system) consists of an Ultrafiltration Biomax-500 (Millipore) and a Masterflex pump with a speed controller. The schematic of the HG-NV isolation system is depicted in FIG. 7. The supernatants with exosomes depleted were passed through a 0.2 µm filter before loading on the HG-NV isolation system. The supernatants were passed through the Ultrafiltration Biomax-500 column at a flow rate of approximately 3 ml/min, and any molecules less than 500 kDa that passed through the column were collected in a waste jar. Molecules larger than 500 kDa were retained, concentrated, and subjected to sucrose gradient centrifugation.

Purification of HG-NVs Using Sucrose Gradients.

After passing through the HG-NV isolation system, molecules larger than 500 kDa were centrifuged on a 8-45% sucrose density gradient as described previously. The purified HG-NVs and exosomes were prepared for EM using a conventional procedure and observed using an FEI Tecnai F20 electron microscope operated at 80 kV and a magnification of 30,000. Photomicrographs were taken using an AMT camera system.

Cell Culture.

The 4T1 mouse mammary tumor, MDA-MB-231 human breast tumor, CT26 colon tumor and 2H11 endothelial cell lines were purchased from ATCC. Cells were cultured in high glucose DMEM supplemented 10% FBS and antibiotics (100 units/ml penicillin and 100 µg/ml streptomycin) at 37° C. in a humidified atmosphere containing 5% $CO_2$. For exosome and HG-NV isolation, cells were cultured in DMEM supplemented with 10% FBS, previously centrifuged at 100,000×g overnight to eliminate bovine-derived exosomes. After 24 h in culture, the cells were washed with PBS 2× and cultured for additional 24 h with sera free DMEM medium. The supernatants were harvested for isolating exosomes and HG-nanoparticles and measuring HG-nanoparticle size.

Measurement of Particles Size and Zeta Potential.

Measurement of the average particle size and particle size distribution, and zeta potential was performed using a Zetasizer Nano ZS (Malvern Instruments, Malvern, UK). The supernatants collected from the cultured cells or plasma collected from mice or human subjects were diluted in PBS before particle size was measured with the Zetasizer Nano ZS according to the instructions described in the manual. Hydrodynamic diameter was determined by dynamic light scattering. The average and standard deviation (SD) were calculated from at least 10 samples. Human samples from healthy subjects and patients were collected at University of Louisville Hospital. Use of human samples was approved by the Institutional Review Board of the University of Louisville Hospital and was conducted in accordance with international guidelines for the use of human tissues.

Exosome Isolation.

Exosomes were isolated according to a protocol that was described previously. In brief, cell culture medium was subjected to consecutive centrifugation steps (500×g, 2,000×g, 3,000×g and 10,000×g) to remove cellular debris and large vesicles. Exosomes were then pelleted with ultracentrifugation at 100,000×g (2 hr) and resuspended in PBS for sucrose gradient centrifugation using the method as described previously. The exosome-depleted supernatants were saved for isolation of HG-NVs. The protein content of the exosomes and HG-NVs were determined using a BCA protein assay kit (Pierce, Rockford, Ill., USA).

SDS-PAGE and Western Blot Analyses.

100 µl of each sample (40 µg) were added to an equal volume of boiling 2× sample buffer and kept at 100° C. for 7 min as described previously. The samples were then subjected to 10% SDS-polyacrylamide gel electrophoresis and separated proteins were transferred to nitrocellulose membranes. The western blot was carried out with the anti-CD63, Tsg101, albumin antibodies (Santa Cruz Biotechnology, Santa Cruz, Calif.) or anti-GAPDH antibody as a control.

RNA Extraction and Real-Time PCR.

Total RNA from 4T1 exosomes and HG-NVs was extracted by TRIzol Reagent. Briefly, exosomes and smaller particle samples were homogenized in 1 ml Trizol and incubated at 22° C. for 10 min. 0.2 ml of chloroform was mixed and incubated with Trizol reagent at 22° C. for 2-3 min. Samples were centrifuged at 12,000×g for 15 min at 4° C. The aqueous phase was transferred into a new tube, 0.5 ml of 100% isopropanol added to the aqueous phase and the sample incubated at 22° C. for 10 min. The sample was centrifuged at 12,000×g for 10 min at 4° C. and the pellet washed with 1 ml of 75% ethanol and dissolved in DEPC treated water for RNA sequencing and real-time PCR analysis. For quantification of genes of interest, RNA (300 ng) was reverse-transcribed with Superscript III and random primers (Invitrogen). cDNA samples were amplified in a CFX96 Realtime System (Bio-Rad Laboratories, Hercules, Calif., USA) and Sso Fasteva green supermixture (Bio-Rad Laboratories) according to the manufacturer's instructions. Fold changes in mRNA expression between treatments and controls were determined by the SCT method as described previously. Differences between groups were determined using a two-sided Student's t-test and one-way ANOVA. Error bars on plots represent ±SE, unless otherwise noted. The data were normalized to a GAPDH reference. All primers were purchased from Eurofins MWG Operon. All assays were performed in triplicate a minimum of three times.

To confirm that the nucleic acid isolated from HG-NVs was RNA, nucleic acid from HG-NVs was treated with 1.0 µg/µl RNase (Sigma) or DEPC treated water as a control for 15 min at 37° C. before the samples were loaded on a 12% polyacrylamide gel. A total of 1 µg RNA isolated from HG-NVs was resolved on 12% polyacrylamide (acrylamide/bis-acrylamide, 29:1) gels containing 8 M Urea and 1× Tris-Boric Acid-EDTA (TBE, 89 mM tris (pH 7.6), 89 mM boric acid, 2 mM EDTA). After electrophoresis, the gel was stained with ethidium bromide (0.5 µg/ml) and visualized using a UVP PhotoDoc-It™ Imaging System (UVP, Montpelier, Md.).

RNA Sequencing Analysis.

Total RNA was extracted from 4T1 exosomes and HG-NVs and submitted to the Translational Genomics Research Institute (Phoenix, Ariz., USA) for whole transcriptome (WT) sequencing analysis. Briefly, the RNA concentration was measured using Quant-it Ribogreen Assay (Life Technologies). 10 ng of RNA were used in the SMARTer Universal Low Input RNA kit (Clontech) for cDNA synthesis. Once cDNA was made, the double stranded cDNA in the samples was measured using Picogreen (Life Technologies). 10 ng ds cDNA were used in the Kapa Biosciences kit, each sample was assigned a unique PCR barcode and 6 PCR cycles were performed for each sample. Samples were then pooled and loaded onto an Illumina HiSeq 2500. For both the WT and small-RNA sequencing, the raw sequence image files from the Illumina HiSeq 2500 in the form of .bcl are converted to the fastq format and checked to ensure the quality scores did not deteriorate drastically at the read ends. The fastqs were trimmed to remove the adapters using Trimmomatic, where the leading and trailing low quality bases below 3 were removed and any reads under the minimum length of 36 nts were discarded. The fastqs were then aligned to the 8059 expressed sequence tags (ESTs) for the 38116 ESTs for Zingiber Officinale from NCBI or the mouse genome (MouseGRCm38, ENSEMBL 79) using STAR v2.4.0j. The STAR aligned sam files are converted to .bam files and sorted by coordinated positions using SAM tools v0.1.19. The read counts were generated using htseq-count (intersection non-empty mode) and the counts for each of the ESTs were generated using idxstats by SAMtools v0.1.19. To validate the RNA sequencing data, a qPCR analysis was performed. The genes that are significantly higher in HG-NVs than in exosomes were further analyzed using the Ingenuity Pathways Analysis (IPA) software (Ingenuity Systems, Redwood City, Calif.). Briefly, a file containing gene identifiers (ID) was uploaded and specified mouse as the species. Enrichment of the focus genes (about 300 genes) in the networks were assessed via Fisher's exact test and used to rank the networks. Furthermore, the software identified top functions and diseases associated with each network via enrichment scores, highlighting the biological significance of the results.

Proteomic Analysis.

4T1 and MDA-MD-231 exosomes and HG-NVs were lysed in protein lysis buffer and 100 µg of proteins were electrophoresed on 10% SDS-polyacrylamide gels. Coomassie-stained SDS-polyacrylamide gels were cut into 10 strips to correlate with the gel lanes and trypsinized. The digested peptides were loaded on a 100 nm×10 cm capillary column packed in-house with C18 Monitor 100 A-spherical silica beads and eluted by a 1 h gradient of 10-100% acetonitrile, 0.1% TFA. Mass spectrometry analysis was performed and analyzed using an LTQ XL spectrometer (Thermo Finnigan) at the UAB Proteomic Core Facility. Protein hits were validated using a method as described previously. Proteins were evaluated by Ingenuity Pathways Analysis software to identify global functions of the proteins. The biological functions assigned to each network were ranked according to the significance of that biological function to the network. A Fischer's exact test was used to calculate a p value. A detailed description of IPA can be found on the Ingenuity Systems website.

Lipidomic Analysis.

Lipid samples extracted from either 4T1 exosomes or HG-NVs were submitted to the Lipidomics Research Center, Kansas State University (Manhattan, Kans.) for analysis using a method as described previously. In brief, the lipid composition was determined using a triple quadrupole mass spectrometer (an Applied Biosystems Q-TRAP, Applied Biosystems, Foster City, Calif.). The data were reported as % of total signal for the molecular species determined after normalization of the signals to internal standards of the same lipid class.

Tlc Analysis.

Lipids from either 4T1 exosomes or HG-NVs were extracted and quantitatively analyzed using a method as described previously. LC was performed according to the method of Masukawa et al. Briefly, HPTLC-plates (silica gel 60 with concentrating zone, 20 cm×10 cm; Merck) were used for the separation. After aliquots of concentrated lipid samples extracted from either 4T1 exosome or HG-NV lipids were separated on a plate, the plate was developed with chloroform/methanol/acetic acid (190:9:1, by vol). After drying, the plates were sprayed with a 10% copper sulfate and 8% phosphoric acid solution and were then charred by heating at 180° C. for 5 min. The plate was imaged with an Odyssey Scanner (LI-COR Bioscience, Lincoln Nebr.).

In Vitro Differentiation of DC and Macrophages from BM Precursors.

BM-derived DC were generated from primary cultures of femoral marrow from 6- to 8-wk-old female wild-type (WT) BALB/c mice as described previously. In brief, BM cells were flushed from the femurs of 6- to 8-wk-old mice using an RPMI 1640-filled syringe to obtain a single-cell suspension. After erythrocytes were depleted, the cells were washed twice with RPMI 1640 (Invitrogen Life Technologies) containing 1% heat-inactivated FBS, and then resuspended in RPMI 1640 supplemented with 10% exosomes depleted FBS, 1 mM pyruvate (Sigma-Aldrich), 1× nonessential amino acids (Sigma-Aldrich), 2 mM glutamine (Sigma-Aldrich), 50 nM 2-ME (Invitrogen Life Technologies), and 20 ng/ml recombinant mouse GM-CSF and 20 pg/ml mouse IL-4 (PeproTech) for DC differentiation and M-CSF (100 U/ml) for macrophages differentiation. The cells were plated at a density of $2 \times 10^6$ cells/ml in 6-well plates and cultured at 37° C. in a 5% $CO_2$ atmosphere. After 7 days in ex vivo culture, the differentiated DCs (>90% $CD11b^+CD11c^+$) and macrophages (90%>$CD11b^+F4/80^+$) determined by FACS analysis were treated with 4T1 exosomes or HG-NVs (10 μg/ml). Seven hours after the treatments, cell culture supernatant was harvested for cytokine array assay.

In Vitro Culture Immature Myeloid Cells from BM Precursors.

Bone marrow was isolated and cultured after RBC lysis as described previously. RBC-depleted bone marrow cells were cultured in RPMI 1640 medium containing 10% exosomes depleted FBS with the addition of glutamine, 2-ME, sodium pyruvate, nonessential amino acid, antibiotics (Invitrogen), and GM-C S F (20 ng/ml), and cultured at 37° C. in a 5% $CO_2$ atmosphere. 4T1 exosomes or HG-NVs (10 μg/ml) were added to the BM cell culture medium on days 0 and 3. Seven hours after the last addition of 4T1 exosomes or HG-NV (10 μg/ml), cell culture supernatant was harvested for cytokine array assay as described below.

Cytokines Detection in the Supernatants of Cultured Cells.

Inflammatory cytokines in the cultured supernatants harvested from BM derived DCs, macrophages, and immature monocytes were detected with Proteome Profiler Mouse Cytokine Array kit (Cat. No. ARY006, R&D System, Minneapolis, Minn., USA) according to the manufacturer's protocol. Briefly, the supernatant of samples was collected by centrifugation at 10,000×g for 5 min at 4° C. and the total protein was quantified using a NanoDrop 8000. After blocking for 1 h, the membranes were incubated with a mixture of reconstituted Cytokine Array Detection Antibody Cocktail and the supernatant overnight at 4° C. After washing 3×, the membranes were incubated with streptavidin-HRP for 30 min at 22° C. After washing 3×, the membranes were incubated with 1 ml of Chemi Regent Mix for 1-2 min at 22° C. before exposing to X-ray film for 1-5 min. The signal intensity of each dot was quantified with LI-COR imaging system and analyzed with LI-COR® Image Studio™ Lite Software V3.1 (Li-COR bioscience, Lincoln, Nebr.)

Mice.

Six to 12-week-old BALB/c and NOD-scidIL-2Ry$^{null}$ (NOG) mice which lack mature T cells, B cells, or functional NK cells, and are deficient in cytokine signaling were obtained from Jackson Laboratories. All animal procedures were approved by the University of Louisville Institutional Animal Care and Use Committee.

Hematoxylin and Eosin (H&E) Staining.

For histopathology analysis, H&E staining was performed on paraffin-embedded liver and lung sections using a method as described previously.

Tumor Cell and Endothelial Cell Proliferation Assay.

4T1 tumor cells and 2H11 endothelial cells cultured at 80% confluency were treated with 4T1 exosomes or HG-NV (30 μg/ml) for 24 h. Then, the cells were detached from the cell culture plate using trypsin digestion and washed with PBS. The cell pellet was incubated with cold 70% ethanol for 2 h at −20° C. The cells were washed twice with staining buffer (PBS with 1% FBS, 0.09% $NaN_3$), and stained for 30 min with properly diluted anti-Ki-67 antibody (e-biosciences). Stained cells were washed prior to FACS analysis.

In Vivo Image of i.v. Injected HG-NVs.

To determine the distribution of HG-NVs in mice, DiR dye labeled 4T1 HG-NVs (50 μg) were prepared and intravenously injected into mice. The mice were imaged over a 6-hour period using a Carestream Molecular Imaging system (Carestream Health, Woodbridge, Conn.). For controls, mice (five per group) received DIR dye in PBS at the same concentration for DIR dye-labeled HG-NVs. Images were collected using a high-sensitivity CCD camera with an exposure time of 2 minutes for imaging.

To determine the percentages of leukocytes from liver and lung taking up HG-NVs, BALB/c mice (n=5) were tail-vein injected with 100 μg PKH67 (Sigma) fluorescent dye labeled HG-NVs/mouse in 100 μl of PBS. 16 h after the injection, mice were sacrificed and leukocytes from liver and lung were isolated using a method as described previously. Isolated cells were stained with anti-CD11C (dendritic cells), F4/80 (macrophages), and CD11b (total myeloid cells) or Ly6C (monocytes). Subsets of populations with PKH67$^+$ cells were defined using antibodies against CD11c, F4/80, CD11b or Ly6C. All data were analyzed using FlowJo FACS software.

Murine Breast Cancer and Colon Cancer Models.

Xenograft tumor growth models were used to demonstrate the biological effects of tumor cell derived HG-NVs on tumor progression. To generate a mouse model of breast cancer, $5 \times 10^4$ 4T1 tumor cells per mouse were orthotopically injected into the mammary fat pads. Female BALB/c mice were purchased from the Jackson Laboratory (Bar Harbor, Me.). When tumors reached approximately 60 mm³ in volume, the mice were randomly assigned to different treatment groups and i.v. injected with 4T1 HG-NVs or exosomes. Mice were treated every 3 days for a total of 4 times. Growth of the tumors was measured using a method as described previously. Within two weeks after the last injection of HG-NVs, the tumors became necrotic, at which time the experiment had to be terminated. Liver and lung metastasis was evaluated on formalin fixed, paraffin embedded tissue. Serial sections of 5 µm thickness were stained with H&E for morphological analysis.

To generate a mouse model of colon cancer, 1×10⁵ colon tumor cells were injected subcutaneously per mouse. When tumors reached approximately 50 mm³ in volume, the mice were randomly assigned to different treatment groups and injected intra-tumor with CT26 HG-NVs or exosomes (100 µg in 30 µl of PBS) on day 0 and 6. At day 1 after the last intra-tumor injection of CT26 HG-NVs or exosomes, a small left abdominal flank incision was made and the spleen was exteriorized for the intra-splenic injection of CT26 tumor cells (1×10⁵). The prepared cells were injected into the spleen using a 30-gauge needle. To prevent tumor cell leakage and bleeding, a cotton swab was held over the site of injection for 1 min. The injected spleen was returned to the abdomen and the wound was sutured with 6-0 black silk. For both 4T1 breast cancer and CT26 colon cancer models, liver and lung metastasis was evaluated on formalin fixed, paraffin embedded tissue. Serial sections of 5 µm thickness were stained with H&E for morphological analysis. Growth of the tumors was measured using a method as described previously. Tumors were measured with a caliper and tumor volumes were calculated using the formula: length×width² and presented as the mean±SD. The number of metastatic foci was counted under low-power (10× objective) in at least 5 randomly selected locations of each H&E stained specimen of liver and lung by 3 observers blinded to the treatment protocol. The number of tumor nodules represents the mean, with error bars representing the SEM.

To determine the effect of HG-NVs and exosomes on the induction of the cytokines IL-6 and TNF-α, which both play a role in the inflammatory mediated promotion of tumor progression, cytokine levels were measured on lung and liver tissue lysates using ELISA kits (eBioscience). Removed lung and liver tissue was flash-frozen in liquid nitrogen until subjected to lysis. To obtain tissue lysates, approximately 30 to 50 mg of tissues were minced and sonicated in 500 µl of lysis buffer (50 mM Tris-HCl pH 7.5) containing 100 mM sodium fluoride, 30 mM sodium pyrophosphate, 2 mM sodium molybdate, 1 mM sodium ortho vanadate, 1 mM glycerophosphate, and 1× protease inhibitor cocktail on ice. Samples were centrifuged at 13,000 rpm for 20 minutes at 4° C. Clear supernatant was collected and used for ELISA. Protein quantification in the lysate was done using the bicinchoninic acid (BCA) method. Serum were also collected on the day when mice were sacrificed and used in an ELISA to detect the induction of cytokines IL-6, IL-10 and TNF-α.

Quantification of HG-NV and Exosome RNA from Mice in a LPS-Induced Septic Shock Mouse Model and 4T1 Tumor Bearing Mice.

Nine week-old BALB/c female mice were intraperitoneally injected with LPS (10 mg/kg of body weight) or PBS as control. Anticoagulated blood samples were collected 18 h after the I.P. injection. HG-NV RNA was extracted from exosome depleted plasma and the levels of HG-NV RNA were quantitatively analyzed with real-PCR assay. Anticoagulated blood samples were collected from 4T1 tumor bearing mice for quantitative analysis of levels of HG-NV and exosome RNA. Fold changes of HG-NV RNA were expressed as the levels of HG-NV RNA from 4T1 tumor bearing mice or LPS challenged mice compared to PBS treated mice (naïve mice).

Example 1—Identification of Nanovesicles

Figure 1B:
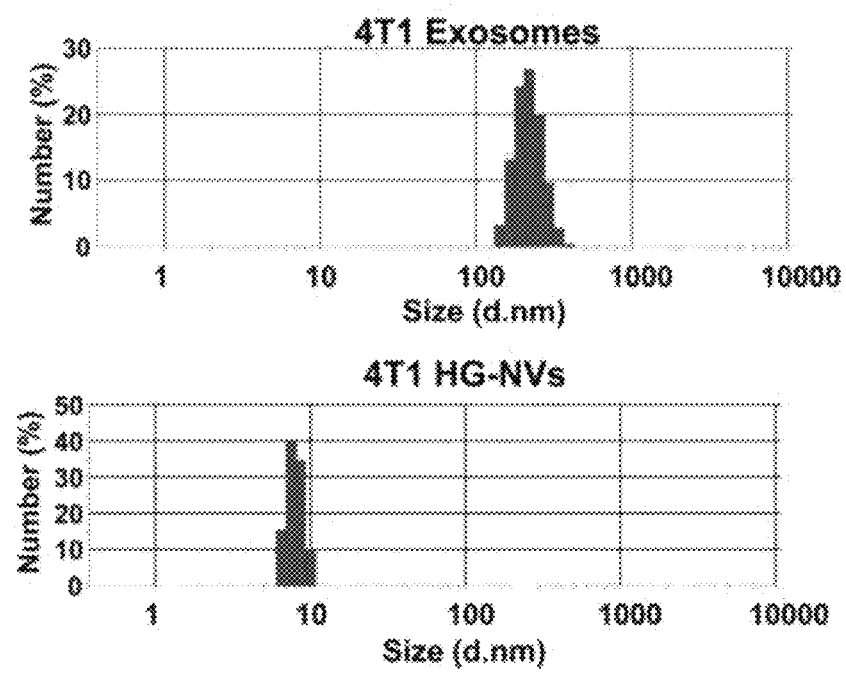
Figure 1C:
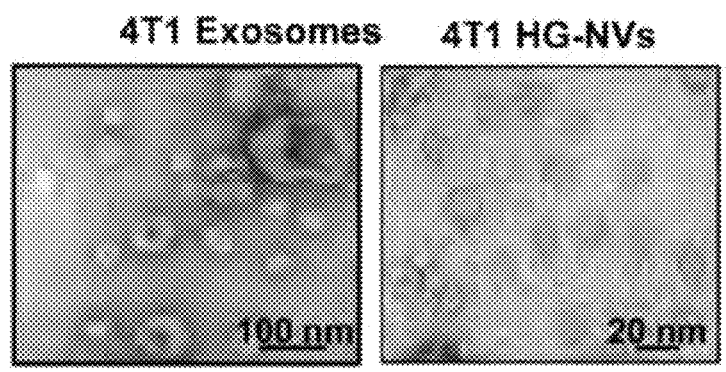
Figure 1D:
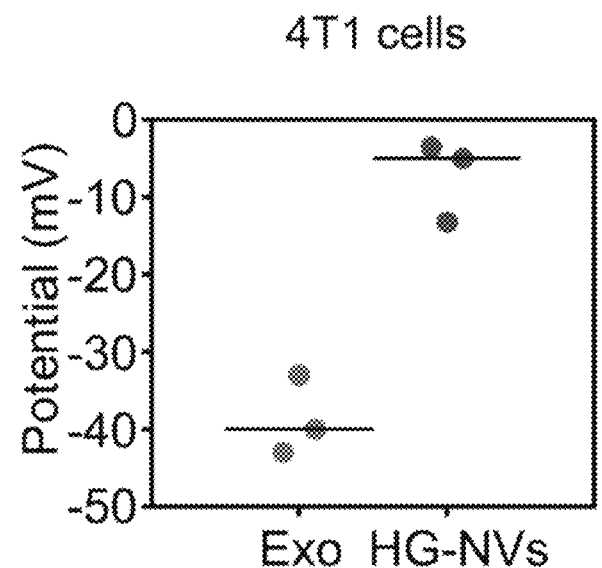

The heterogeneous size of EVs is based on data generated from EVs after multiple in vitro manipulations. The identification of EVs prior to isolation by in vitro manipulations was not possible. Peripheral blood collected from naïve and tumor bearing mice, healthy subjects and diseased patients, was first examined in the cell culture supernatants using a standard nanosizer (Zetasizer Nano ZS). It was observed that all samples examined predominantly contained nanosize particles (FIG. 1A). Nanosize particles were detected in the blood of naïve mice (8.79±1.68 nm), 4T1 breast tumor bearing mice (7.12±2.11 nm), SLE patients (7.69±1.57 nm) and healthy subjects (9.25±1.37 nm), means±S.E.M). Nanosized particles were also been detected in cell culture supernatants of 4T1 cells (9.41±1.83 (nm) and of MDA-MB-231 human breast tumor cell line (8.94±2.55 (nm) indicating that EVs with a diameter of 8-12 nm were readily detected in blood and cell culture supernatants. The presence of the EVs with a diameter of 8-12 nm was also observed in the blood samples of mice with acute inflammation induced by an IP injection of LPS and in blood samples from different genetic background mice (C57BL/6 versus BALB/c) (Table 1). Therefore, unlike other EVs, with minimal in vitro manipulation this extracellular HG-NV can be detected with a nanosizer and are much less heterogeneous in size (8-12 nm) than other EVs (for an example, exosomes, 50-150 nm, microparticles 300-1,000 nm). To further characterize the HG-NVs released from 4T1 tumor cells, HG-NVs from exosome-depleted samples were isolated with a simple column infiltration method. The column filtration consisted of a filter with 500 kDa cutoff (FIG. 7) and pumped to regulate the speed of fluid passing through the column. After a simple, one step procedure for sample concentration with the column infiltration, followed by sucrose gradient purification, the size distribution of the HG-NVs was determined using a nanosizer (FIG. 1B) and confirmed by electron microscopy (FIG. 1C). HG-NVs were less charged (FIG. 1D) than other exosomes isolated from the same sample used for HG-NV isolation.

TABLE 1

Size of Peripheral Blood HG-NVs

| | | 0 h | LPS 6 h | LPS 24 h |
|---|---|---|---|---|
| C57BL/6 | M | 7.489 ± 2.238 | 7.449 ± 1.70 | 8.212 ± 2.122 |
| | F | 7.242 ± 1.465 | 7.254 ± 1.732 | 7.518 ± 1.975 |
| | P | 8.409 ± 2.298 | 7.108 ± 1.811 | 8.193 ± 2.332 |
| BALB/C | M | 8.79 ± 2.068 | 9.481 ± 2.054 | 6.195 ± 1.622 |
| | F | 8.60 ± 2.049 | 9.18 ± 1.869 | 7.312 ± 1.918 |
| | P | 6.29 ± 1.834 | 8.375 ± 1.988 | 7.78 ± 2.042 |
| SCID | M | 8.214 ± 2.153 | 8.754 ± 2.183 | 7.692 ± 2.225 |
| | F | 7.303 ± 1.873 | 7.336 ± 1.992 | 6.769 ± 1.931 |

Note:
Plasma collected from mice (n = 5) as listed in the first column were diluted in PBS before the particles' size were measured with a Zetasizer Nano ZS. M = male, F = female, and P = pregnancy, SCID = NK and T cell immune deficient NSG mice. Peripheral blood was collected at 0, 6, and 24 h after mice were i.p. injected with LPS (18.5 mg/kg, Sigma-Aldrich).

Example 2—Identification of HG-NV RNA Composition

Figure 2A:
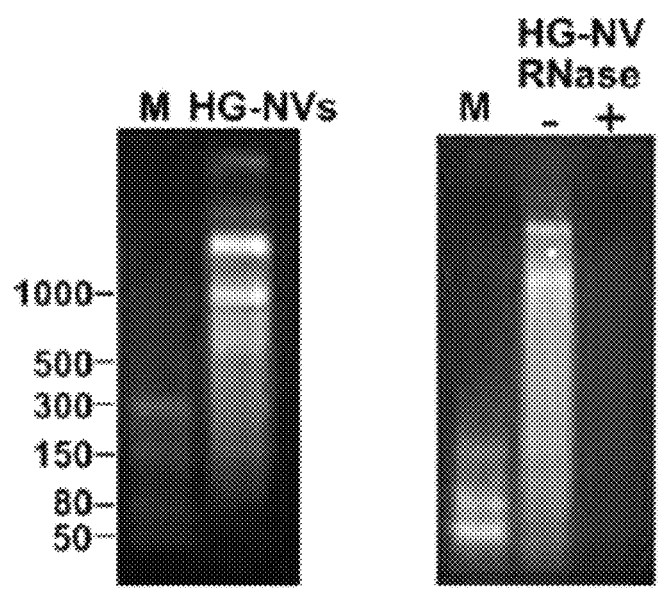
Figure 2B:
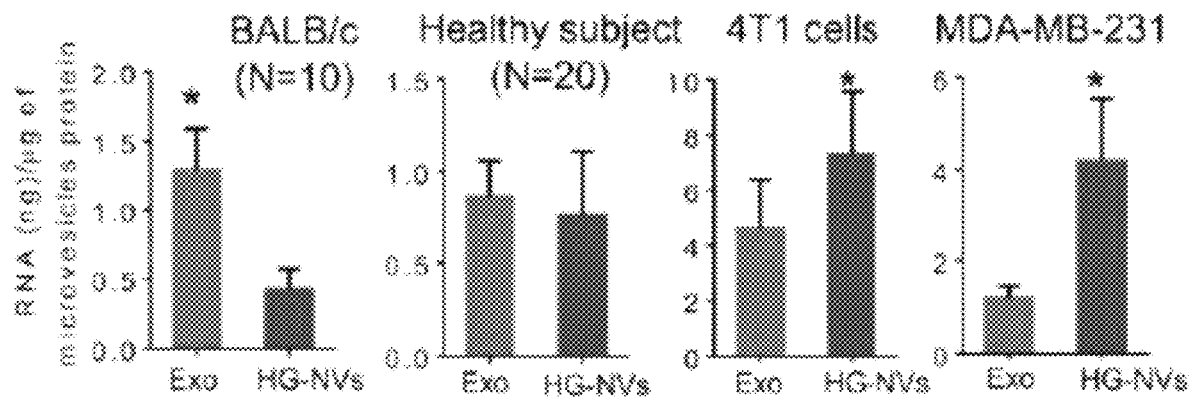

Most cells release extracellular vesicles (EVs) containing RNAs, proteins, and lipids. To determine whether HG-NVs contained RNA, the HG-NVs and exosomes were taken from 4T1 cells and their RNA was isolated. Substantial amounts of small-sized RNAs were detected by gel electrophoresis. The HG-NV RNA was found to be resistant to RNase treatment (FIG. 2A, right panel). Next, the amounts of RNAs from HG-NVs were compared with the amounts of RNAs in exosomes. Interestingly, although the amounts of HG-NV RNAs from naïve mouse plasma was less than those from exosomes, there was no difference in the levels of RNA present in the HG-NVs and exosomes from the plasma of healthy subjects (FIG. 2B). However, the amounts of RNA extracted from HG-NVs of 4T1 cells and the MDA-MB-231 human breast tumor cells were higher than the amounts of RNAs extracted from their exosomes (FIG. 2B, right two panels).

Figure 2C:
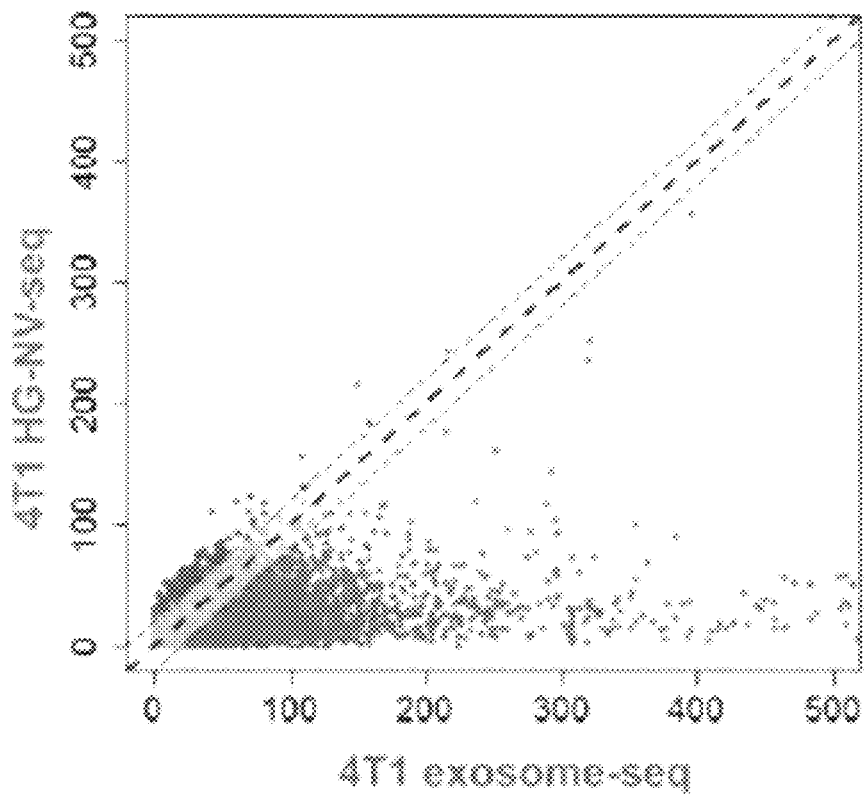
Figure 2D:
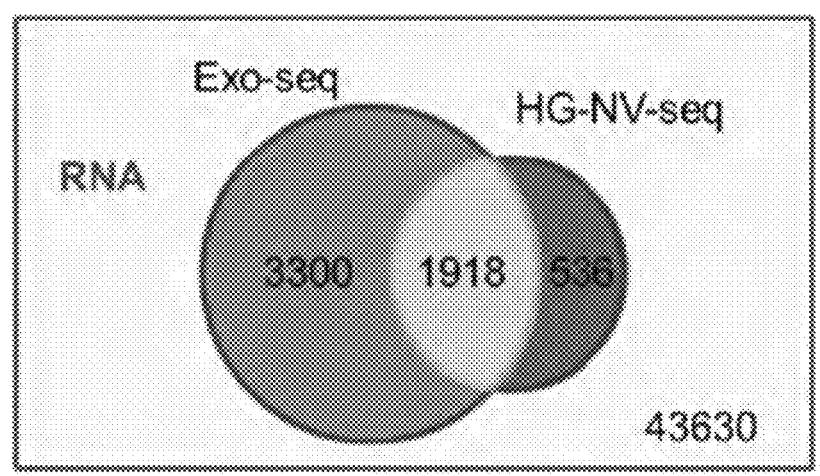
Figure 2F:
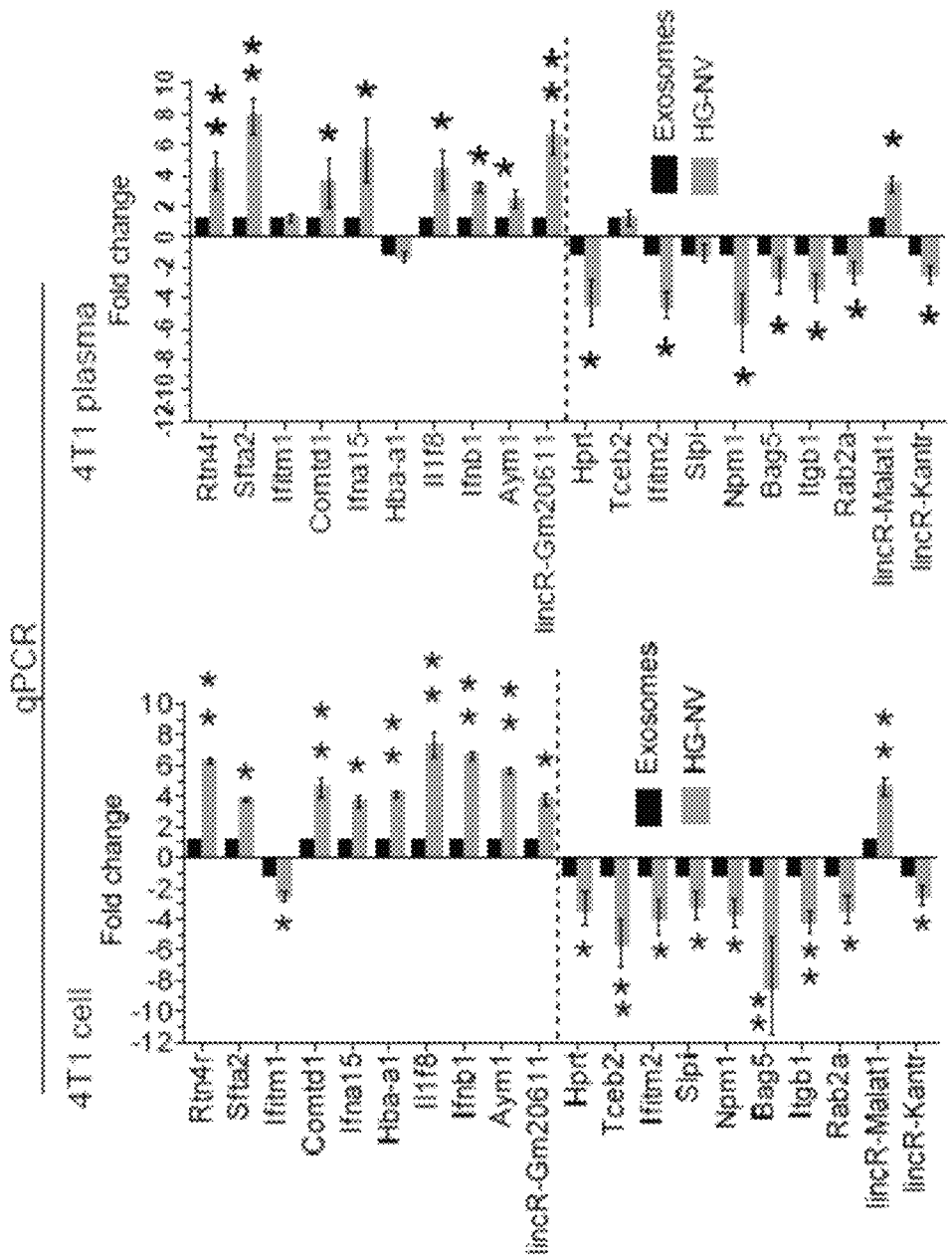
Figure 2G:
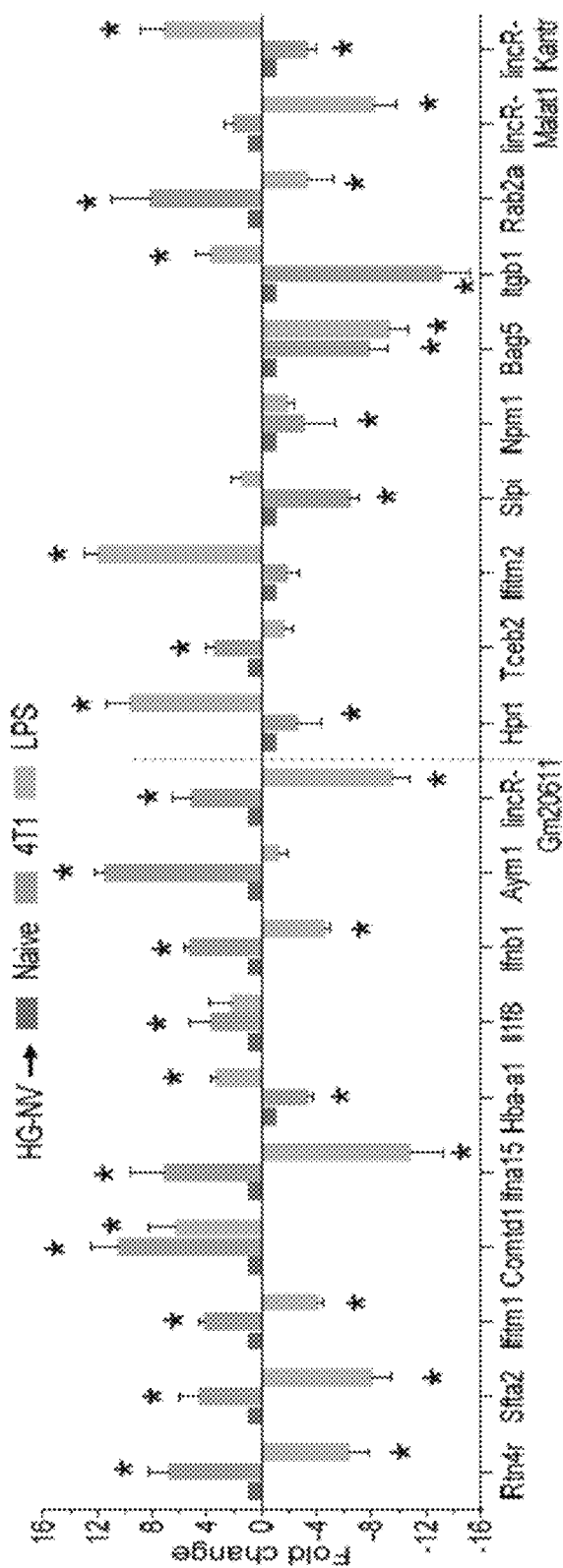
Figure 2H:
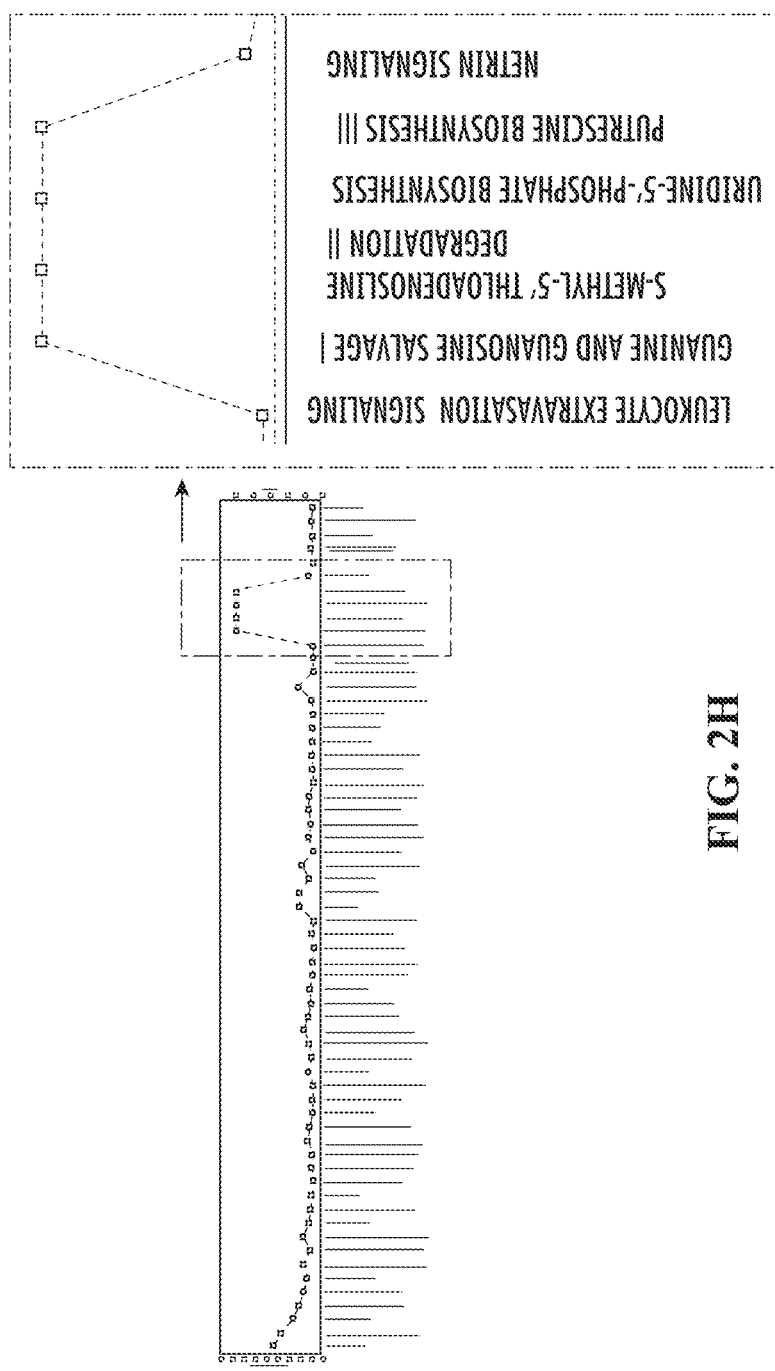
Figure 2I:
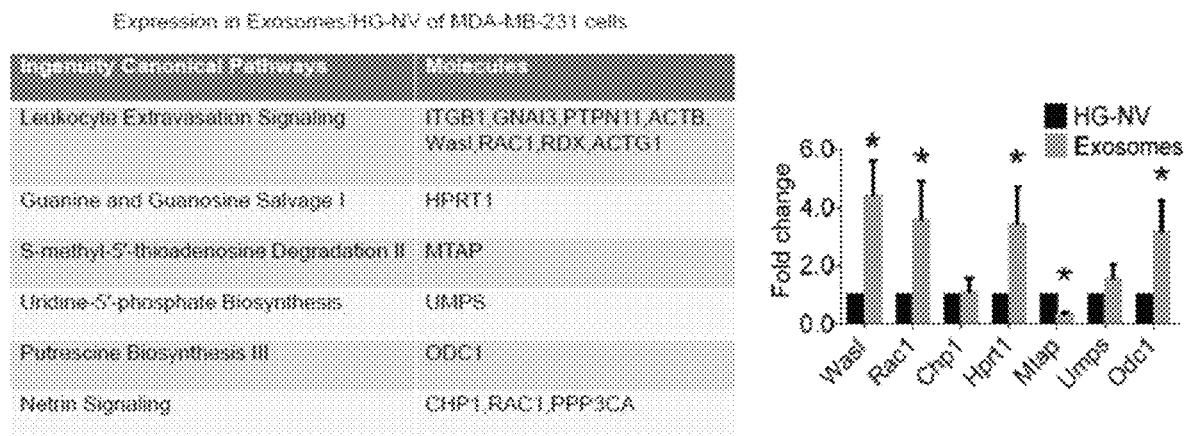

To examine if the RNAs were unique to or common between exosomes and HG-NVs, RNA from 4T1 HG-NVs and exosomes was sequenced (Tables 2a-2b). For RNA data analysis, the low abundant RNAs (<4 normalized counts per million RNA reads) were first removed and the remaining RNAs were then compared between 4T1 exosomes and HG-NVs (FIG. 2C). Of these, 1,918 were detected in both exosomes and HG-NVs (FIG. 2D). In addition to the RNAs that were shared, some RNAs were also identified that were unique to HG-NVs (536) and exosomes (3,300). To validate the RNA sequencing data, a qPCR analysis was performed on 20 RNAs that were randomly selected from the RNA profile that were present or absent in HG-NVs in comparison to exosomes. The data (18/20 RNAs) (FIGS. 2E-2F) from qPCR were consistent with the data generated from RNA sequencing. Next it was determined whether the PCR data generated from the 4T1 cell line could be repeated in an animal model for potential use as biomarkers for disease diagnosis. HG-NVs and exosomes were isolated from the plasma of 4T1 tumor bearing mice. The data (FIG. 2F, right panel, 17/20 RNAs) from qPCR were consistent with the data generated from the 4T1 cell line. Then, it was further determined whether the HG-NV RNAs that increased in 4T1 tumor bearing mice was disease specific by comparing the results with a LPS induced inflammation model. The reason a LPS induced inflammation mouse model was used was because inflammation has been known to be involved in the development and progression of numerous diseases. Fifteen out of 20 HG-NV RNAs were 4T1 tumor specific. Eight of 15 of HG-NV RNAs were increased in the plasma of 4T1 tumor bearing and 7/15 were decreased in comparison with HG-NV RNAs in the plasma of LPS challenged mice. Collectively, the PCR data suggested that these HG-NV RNAs could be used as a biomarker for disease diagnosis. The data generated from ingenuity path analysis (IPA) of 4T1 HG-NVs and exosome RNA profiles suggested that the most abundant functions for HG-NV RNAs (FIG. 2H) were altered and related to the biosynthesis pathways of guanine/guanosine, adenosine/uridine and putrescine biosynthesis III. This conclusion was also supported by real-time PCR results generated from MDA-MB-231 exosome/HG-NV RNA. Seven randomly selected RNAs that are involved in the biosynthesis pathways of guanine/guanosine, adenosine/uridine and putrescine biosynthesis III were quantitatively analyzed with real-time PCR. The results indicate that 6/7 of HG-NV genes are decreased in the MDA-MB-231 HG-NV in comparison to MDA-MB-231 exosomes (FIG. 2I).

TABLE 2a

High-level RNA Detected in Exosome of 4T1

| Identified Proteins | Counts exo | Counts HG-NV | log2- fold change |
|---|---|---|---|
| mitochondrially encoded 16S rRNA | 8647 | 53 | 7.3 |
| mitochondrially encoded 12S rRNA | 11722 | 87 | 7.1 |
| RNA, Y3 small cytoplasmic (asso Ro protein) | 1882 | 16 | 6.8 |
| ribosomal protein L14 | 518 | 6 | 6.2 |
| ribosomal protein L23 | 409 | 5 | 6.1 |
| RNA, Y1 small cytoplasmic, Ro- associated | 1451 | 21 | 6.0 |
| RNA, 7SK, nuclear | 2568 | 42 | 5.9 |
| predicted gene 15564 | 6086 | 102 | 5.9 |
| mitochondrially encoded cytochrome b | 696 | 11 | 5.9 |
| predicted gene, 22973 | 376 | 6 | 5.8 |
| golgi SNAP receptor complex member 2 | 688 | 12 | 5.7 |
| mitochondrially encoded cytochrome c oxidase I | 785 | 14 | 5.7 |
| ribosomal protein S20 | 393 | 7 | 5.6 |
| ribosomal protein S11 | 1198 | 24 | 5.6 |
| guanosine diphosphate dissociation inhibitor 2 | 204 | 4 | 5.4 |
| solute carrier family 25, member 4 | 309 | 7 | 5.3 |
| ferritin light chain 1 | 2905 | 74 | 5.3 |
| predicted gene 15772 | 881 | 22 | 5.3 |
| stearoyl-Coenzyme A desaturase 2 | 612 | 15 | 5.3 |
| actin, beta | 686 | 18 | 5.2 |
| ribosomal protein S26 | 276 | 7 | 5.1 |
| lectin, galactose binding, soluble I | 687 | 19 | 5.1 |
| spindlin 1 | 205 | 5 | 5.1 |
| ribosomal protein L35 | 230 | 6 | 5.0 |
| eukaryotic translation initiation factor 3, subunit A | 719 | 21 | 5.0 |
| ferritin heavy chain 1 | 2434 | 74 | 5.0 |
| mitochondrially encoded NADH dehydrogenase 1 | 410 | 12 | 5.0 |
| AHNAK nucleoprotein (desmoyokin) | 1688 | 53 | 5.0 |
| nucleolin | 3301 | 105 | 5.0 |
| predicted pseudogene 8730 | 464 | 14 | 5.0 |

TABLE 2a-continued

High-level RNA Detected in Exosome of 4T1

| Identified Proteins | Counts exo | Counts HG-NV | log2-fold change |
|---|---|---|---|
| eukaryotic translation initiation factor 4E binding protein 2 | 305 | 9 | 4.9 |
| ribosomal protein S7 | 458 | 14 | 4.9 |
| nucleophosmin 1 | 1600 | 52 | 4.9 |
| Finkel-Biskis-Reilly murine sarcoma virus ubiquitously expressed | 149 | 4 | 4.9 |
| ribosomal protein L13A | 415 | 13 | 4.9 |
| DnaJ (Hsp40) homolog, subfamily A, member 2 | 198 | 6 | 4.8 |
| ribosomal protein L28 | 396 | 13 | 4.8 |
| aldolase A, fructose-bisphosphate | 509 | 17 | 4.8 |
| guanine nucleotide binding protein (G protein), beta polypeptide 2 like 1 | 422 | 14 | 4.8 |
| histone cluster 1, H4d | 251 | 8 | 4.8 |
| mitochondrially encoded NADH dehydrogenase 2 | 334 | 11 | 4.8 |
| ribosomal protein S9 | 466 | 16 | 4.8 |
| Rho GTPase activating protein 11A | 567 | 20 | 4.8 |
| ribosomal protein L36 | 214 | 7 | 4.7 |
| neuroepithelial cell transforming gene 1 | 373 | 13 | 4.7 |
| ribosomal protein S3A1 | 665 | 24 | 4.7 |
| ribosomal protein S23 | 158 | 5 | 4.7 |
| histone cluster 1, H2ak | 130 | 4 | 4.7 |
| eukaryotic translation elongation factor 1 alpha 1 | 3271 | 124 | 4.7 |
| mitochondrially encoded NADH dehydrogenase 4 | 225 | 8 | 4.7 |
| ribosomal protein L37 | 249 | 9 | 4.6 |
| ribonuclease P RNA component H1 | 8824 | 354 | 4.6 |
| N(alpha)-acetyltransferase 50, NatE catalytic subunit | 148 | 5 | 4.6 |
| ribosomal protein S6 | 615 | 24 | 4.6 |
| ribosomal protein L4 | 658 | 26 | 4.6 |
| acidic (leucine-rich) nuclear phosphoprotein 32 family, member B | 437 | 17 | 4.6 |
| ribosomal protein L19 | 1067 | 43 | 4.6 |
| eukaryotic translation initiation factor 4, gamma 2 | 377 | 15 | 4.6 |
| ribosomal protein L41 | 351 | 14 | 4.6 |
| potassium channel tetramerisation domain containing 10 | 670 | 29 | 4.5 |
| ribosomal protein L18A | 795 | 35 | 4.5 |
| zinc finger, CCHC domain containing 24 | 330 | 14 | 4.5 |
| ubiquitin-conjugating enzyme E2D 3 | 109 | 4 | 4.5 |
| tyrosine 3-monooxygenase/tryptophan 5-monooxygenase activation protein, zeta polypeptide | 241 | 10 | 4.5 |
| LSMI2 homolog (*S. cerevisiae*) | 139 | 5 | 4.5 |
| PRELI domain containing 1 | 278 | 11 | 4.5 |
| chromobox 5 | 763 | 32 | 4.5 |
| ribosomal protein SA | 1285 | 55 | 4.5 |
| eukaryotic translation elongation factor 2 | 1493 | 65 | 4.5 |
| vesicle amine transport protein 1 homolog (*T californica*) | 134 | 5 | 4.5 |
| nudix (nucleoside diphosphate linked moiety X)-type motif 4 | 194 | 8 | 4.4 |
| poly(A) binding protein, cytoplasmic 1 | 3178 | 146 | 4.4 |
| tubulin, beta 5 class I | 427 | 19 | 4.4 |
| predicted gene 9625 | 127 | 5 | 4.4 |
| ribosomal protein S16 | 126 | 5 | 4.4 |
| histone cluster 1, H1e | 336 | 15 | 4.4 |
| U2AF homology motif (UHM) kinase 1 | 483 | 22 | 4.4 |
| H3 histone, family 3B | 417 | 19 | 4.4 |
| sestrin 3 | 145 | 6 | 4.4 |
| methylthioadenosine phosphorylase | 145 | 6 | 4.4 |
| glia maturation factor, beta | 144 | 6 | 4.4 |
| ribosomal protein L30 | 304 | 14 | 4.3 |
| transcription factor 20 | 970 | 47 | 4.3 |
| metastasis associated lung adenocarcinoma transcript 1 | 342 | 16 | 4.3 |
| pantothenate kinase 3 | 180 | 8 | 4.3 |
| S100 calcium binding protein A6 (calcyclin) | 159 | 7 | 4.3 |
| ribosomal protein S21 | 199 | 9 | 4.3 |
| predicted gene, 26191 | 458 | 22 | 4.3 |
| leucine rich repeat containing 58 | 157 | 7 | 4.3 |
| mitochondrially encoded NADH dehydrogenase 5 | 662 | 33 | 4.3 |
| ribosomal protein L32 | 308 | 15 | 4.3 |
| ribosomal protein S27A | 286 | 14 | 4.3 |
| trafficking protein, kinesin binding 2 | 668 | 34 | 4.3 |
| nuclear fragile X mental retardation protein interacting protein 2 | 94 | 4 | 4.2 |
| cytochrome b5 reductase 3 | 529 | 27 | 4.2 |
| predicted gene, 22405 | 112 | 5 | 4.2 |
| transformation related protein 53 inducible nuclear | 260 | 13 | 4.2 |

TABLE 2a-continued

High-level RNA Detected in Exosome of 4T1

| Identified Proteins | Counts exo | Counts HG-NV | log2-fold change |
|---|---|---|---|
| protein 2 profilin 1 | 184 | 9 | 4.2 |
| RNA binding motif protein 3 | 91 | 4 | 4.2 |
| glutathione peroxidase 4 | 91 | 4 | 4.2 |
| ribosomal protein, large, P0 | 1157 | 62 | 4.2 |
| charged multivesicular body protein 3 | 127 | 6 | 4.2 |
| ribosomalprotein L17 | 180 | 9 | 4.2 |
| fibroblast growth factor receptor substrate 2 | 161 | 8 | 4.2 |
| heat shock protein 90 alpha (cytosolic), class B member 1 | 1335 | 74 | 4.2 |
| ribosomal protein L12 | 367 | 20 | 4.1 |
| guanine nucleotide binding protein, alpha 13 | 259 | 14 | 4.1 |
| prothymosin alpha | 120 | 6 | 4.1 |
| ornithine decarboxylase, structural 1 | 1218 | 70 | 4.1 |
| heat shock protein 9 | 205 | 11 | 4.1 |
| ribosomal protein L8 | 906 | 52 | 4.1 |
| platelet-activating factor acetylhydrolase, isoform 1b, subunit 2 | 187 | 10 | 4.1 |
| ribosomal protein L13 | 611 | 35 | 4.1 |
| ribosomal protein S14 | 135 | 7 | 4.1 |
| growth arrest specific 5 | 556 | 32 | 4.1 |
| pyruvate kinase, muscle | 487 | 28 | 4.1 |
| keratin 18 | 150 | 8 | 4.1 |
| family with sequence similarity 168, member B | 753 | 44 | 4.1 |
| Rho GDP dissociation inhibitor (GDI) alpha | 233 | 13 | 4.1 |
| lactate dehydrogenase A | 248 | 14 | 4.1 |
| eukaryotic translation initiation factor 3, subunit E | 115 | 6 | 4.1 |
| cold shock domain containing E1, RNA binding | 506 | 30 | 4.0 |
| transforming growth factor, beta receptor I | 178 | 10 | 4.0 |
| ribosomal protein L38 | 178 | 10 | 4.0 |
| microtubule-associated protein, RP/EB family, member 1 | 551 | 33 | 4.0 |
| ring finger and CCCH-type zinc finger domains 2 | 355 | 21 | 4.0 |
| actin, gamma, cytoplasmic 1 | 257 | 15 | 4.0 |
| nuclear factor I/X | 384 | 23 | 4.0 |
| protein S10 | 79 | 4 | 4.0 |

TABLE 2b

High-level RNA Detected in HG-NV of 4T1

| Identified Proteins | Counts exo | Counts HG-NV | log2-fold change |
|---|---|---|---|
| cDNA sequence BC018473 | 0 | 31 | −5.0 |
| reticulon 4 receptor | 0 | 24 | −4.6 |
| surfactant associated 2 | 0 | 21 | −4.5 |
| predicted gene, 21786 | 0 | 20 | −4.4 |
| olfactory receptor 430 | 0 | 17 | −4.2 |
| predicted gene 7672 | 0 | 16 | −4.1 |
| interferon induced transmembrane protein 1 | 0 | 15 | −4.0 |
| expressed sequence BB014433 | 0 | 15 | −4.0 |
| predicted gene 9443 | 0 | 15 | −4.0 |
| vomeronasal 1 receptor 212 | 0 | 14 | −3.9 |
| predicted gene 13031 | 0 | 13 | −3.8 |
| T cell receptor alpha variable 7D-3 | 0 | 13 | −3.8 |
| predicted gene 29539 | 0 | 13 | −3.8 |
| Indian hedgehog | 0 | 12 | −3.7 |
| catechol-O-methyltransferase domain containing 1 | 0 | 12 | −3.7 |
| predicted gene, 22061 | 0 | 12 | −3.7 |
| predicted gene, 23247 | 0 | 12 | −3.7 |
| predicted gene 8225 | 0 | 12 | −3.7 |
| CCAAT/enhancer binding protein | 0 | 12 | −3.7 |
| histocompatibility 2, blastocyst | 0 | 12 | −3.7 |
| olfactory receptor 1156 | 0 | 12 | −3.7 |
| immunoglobulin kappa variable 3-10 | 0 | 12 | −3.7 |
| predicted gene 11931 | 0 | 12 | −3.7 |
| predicted gene 12869 | 0 | 12 | −3.7 |
| predicted gene 13434 | 0 | 12 | −3.7 |
| predicted gene, 26752 | 0 | 12 | −3.7 |
| predicted gene 29150 | 0 | 12 | −3.7 |
| predicted pseudogene 336 | 0 | 12 | −3.7 |
| predicted gene 12010 | 1 | 24 | −3.6 |
| predicted pseudogene 8818 | 0 | 11 | −3.6 |
| predicted gene 13771 | 0 | 11 | −3.6 |
| predicted gene 2381 | 0 | 11 | −3.6 |
| predicted gene 20611 | 0 | 11 | −3.6 |
| predicted gene 5435 | 0 | 11 | −3.6 |
| predicted gene 28351 | 0 | 11 | −3.6 |
| predicted gene 8531 | 0 | 11 | −3.6 |
| predicted gene 29441 | 0 | 11 | −3.6 |
| TEC RP23-420P19.1 | 0 | 11 | −3.6 |
| secretoglobin, family 1B, member 20 | 1 | 22 | −3.5 |
| T-box 1 | 0 | 10 | −3.5 |
| olfactory receptor 367, pseudogene | 0 | 10 | −3.5 |
| Sec61 beta subunit | 1 | 21 | −3.5 |
| predicted gene, 26228 | 0 | 10 | −3.5 |
| ankyrin repeat domain 63 | 2 | 32 | −3.5 |
| predicted gene 13983 | 0 | 10 | −3.5 |
| nuclear encoded rRNA 5S 34 | 0 | 10 | −3.5 |
| predicted gene 12590 | 0 | 10 | −3.5 |
| predicted gene 14262 | 0 | 10 | −3.5 |
| RIKEN cDNA 4930515B02 gene | 0 | 10 | −3.5 |
| RIKEN cDNA 1700073E17 gene | 0 | 10 | −3.5 |

TABLE 2b-continued

High-level RNA Detected in HG-NV of 4T1

| Identified Proteins | Counts exo | HG-NV | log2- fold change |
|---|---|---|---|
| predicted gene 15860 | 0 | 10 | −3.5 |
| predicted gene 15775 | 0 | 10 | −3.5 |
| predicted gene, 25958 | 0 | 10 | −3.5 |
| predicted gene 12626 | 0 | 10 | −3.5 |
| TEC RP23-272A7.1 | 0 | 10 | −3.5 |
| processed_pseudogene RP23-21511.2 | 0 | 10 | −3.5 |
| beta-1,3-glucuronyltransferase 2 | 1 | 20 | −3.4 |
| homeobox All | 1 | 19 | −3.3 |
| RIKEN cDNA C130073F 10 gene | 0 | 9 | −3.3 |
| olfactory receptor 250 | 0 | 9 | −3.3 |
| microRNA 369 | 0 | 9 | −3.3 |
| defensin beta 43 | 0 | 9 | −3.3 |
| predicted gene 11553 | 0 | 9 | −3.3 |
| predicted gene 15381 | 0 | 9 | −3.3 |
| predicted gene 12386 | 0 | 9 | −3.3 |
| predicted gene 15660 | 0 | 9 | −3.3 |
| predicted gene 5319 | 0 | 9 | −3.3 |
| cytochrome P450, family 4, subfamily a, polypeptide 29, pseudogene 1 | 0 | 9 | −3.3 |
| predicted gene 14893 | 0 | 9 | −3.3 |
| predicted gene 14108 | 0 | 9 | −3.3 |
| predicted gene 15666 | 0 | 9 | −3.3 |
| RIKEN cDNA E130120K24 gene | 0 | 9 | −3.3 |
| predicted gene 13716 | 0 | 9 | −3.3 |
| predicted gene, 24500 | 0 | 9 | −3.3 |
| matrin 3, pseudogene 2 | 0 | 9 | −3.3 |
| predicted gene 8356 | 0 | 9 | −3.3 |
| histocompatibility 2, Q region locus 2 | 0 | 9 | −3.3 |
| predicted gene 20447 | 0 | 9 | −3.3 |
| serine/cysteine peptidase inhibitor, clade B (ovalbumin), member 10 | 0 | 9 | −3.3 |
| predicted gene, 18006 | 0 | 9 | −3.3 |
| predicted gene, 27784 | 0 | 9 | −3.3 |
| TEC RP24-329M13.1 | 0 | 9 | −3.3 |
| predicted gene 5973 | 2 | 28 | −3.3 |
| TEC RP23-184I13.2 | 2 | 28 | −3.3 |
| cysteine-rich secretory protein 4 | 1 | 18 | −3.2 |
| predicted pseudogene 5540 | 1 | 18 | −3.2 |
| predicted gene 13446 | 1 | 18 | −3.2 |
| predicted gene, 26617 | 1 | 18 | −3.2 |
| RIKEN cDNA 4930455D15 gene | 1 | 18 | −3.2 |
| ankyrin repeat domain 33 | 2 | 27 | −3.2 |
| predicted gene 15784 | 2 | 27 | −3.2 |
| lymphocyte antigen 6 complex, locus G6E | 0 | 8 | −3.2 |
| interleukin 1 family, member 8 | 0 | 8 | −3.2 |
| late cornified envelope- like proline-rich 1 | 0 | 8 | −3.2 |
| predicted pseudogene 5578 | 0 | 8 | −3.2 |
| olfactory receptor 981 | 1 | 17 | −3.2 |
| predicted gene 5065 | 0 | 8 | −3.2 |
| sorting nexin 32 | 1 | 17 | −3.2 |
| protease, serine 34 | 1 | 17 | −3.2 |
| serine/cysteine peptidase inhibitor, clade B (ovalbumin), member 3D | 0 | 8 | −3.2 |
| olfactory receptor 539 | 0 | 8 | −3.2 |
| TEC RP23-259O15.2 | 0 | 8 | −3.2 |
| TEC RP23-141H24.1 | 0 | 8 | −3.2 |
| TEC RP23-293F4.2 | 0 | 8 | −3.2 |
| processed pseudogene RP23-46419.1 | 0 | 8 | −3.2 |
| complement factor D (adipsin) | 0 | 8 | −3.2 |
| RIKEN cDNA 4930431F12 gene | 0 | 8 | −3.2 |
| olfactory receptor 319 | 0 | 8 | −3.2 |
| hemoglobin alpha, adult chain 1 | 0 | 8 | −3.2 |
| microRNA 489 | 0 | 8 | −3.2 |
| predicted gene 16020 | 0 | 8 | −3.2 |
| NEDD4 binding protein 2, opposite strand | 0 | 8 | −3.2 |
| predicted gene 10518 | 0 | 8 | −3.2 |
| predicted gene, 25614 | 0 | 8 | −3.2 |
| immunoglobulin kappa variable 12-47 | 0 | 8 | −3.2 |
| predicted gene 11434 | 0 | 8 | −3.2 |
| RIKEN cDNA 2210409E12 gene | 0 | 8 | −3.2 |
| guanine nucleotide binding protein (G protein), gamma 2 subunit, pseudogene 1 | 0 | 8 | −3.2 |
| predicted gene 8475 | 0 | 8 | −3.2 |
| predicted gene 12191 | 0 | 8 | −3.2 |
| predicted gene 14805 | 0 | 8 | −3.2 |
| predicted gene 15159 | 0 | 8 | −3.2 |
| predicted gene 15812 | 0 | 8 | −3.2 |
| predicted gene 16064 | 0 | 8 | −3.2 |
| RIKEN cDNA 1700123012 gene | 0 | 8 | −3.2 |
| cDNA sequence BC039966 | 1 | 17 | −3.2 |
| predicted gene, 25603 | 0 | 8 | −3.2 |
| predicted gene 6397 | 0 | 8 | −3.2 |
| predicted gene 8428 | 1 | 17 | −3.2 |
| predicted gene, 22002 | 0 | 8 | −3.2 |
| predicted gene, 21847 | 0 | 8 | −3.2 |
| vomeronasal 1 receptor 30 | 0 | 8 | −3.2 |
| interferon alpha 15 | 0 | 8 | −3.2 |
| predicted gene, 16907 | 4 | 44 | −3.2 |
| predicted gene, 17800 | 0 | 8 | −3.2 |
| predicted gene, 26980 | 0 | 8 | −3.2 |
| predicted gene 29253 | 0 | 8 | −3.2 |
| predicted gene 7114 | 0 | 8 | −3.2 |
| leucine rich repeat containing 32 | 2 | 25 | −3.1 |
| predicted gene 4745 | 1 | 16 | −3.1 |
| zona pellucida like domain containing 1 | 1 | 16 | −3.1 |
| T cell receptor beta, variable 16 | 1 | 16 | −3.1 |
| RIKEN cDNA 2210017GI8 gene | 1 | 16 | −3.1 |
| predicted gene, 27043 | 1 | 16 | −3.1 |
| TEC RP24-111F24.1 | 1 | 16 | −3.1 |
| icos ligand | 4 | 41 | −3.1 |
| gasdermin C-like 1 | 2 | 24 | −3.1 |
| 21975 | 2 | 24 | −3.1 |
| RIKEN cDNA E530011L22 gene | 2 | 24 | −3.1 |
| cholinergic receptor, muscarinic 4 | 2 | 23 | −3.0 |
| predicted gene 12221 | 0 | 7 | −3.0 |
| olfactory receptor 1388 | 0 | 7 | −3.0 |
| fibroblast growth factor binding protein 1 | 0 | 7 | −3.0 |
| interferon beta 1, fibroblast | 0 | 7 | −3.0 |
| glycine receptor, alpha 4 subunit | 0 | 7 | −3.0 |
| homeobox ClO | 1 | 15 | −3.0 |
| glycoprotein m6a | 0 | 7 | −3.0 |
| small proline-rich protein 2B | 0 | 7 | −3.0 |
| olfactory receptor 1356 | 0 | 7 | −3.0 |
| WAP four-disulfide core domain 21 | 0 | 7 | −3.0 |
| activator of yeast meiotic promoters 1 | 0 | 7 | −3.0 |
| RIKEN cDNAM5C1000I18 gene | 1 | 15 | −3.0 |
| prolactin family 3, subfamily d, member 1 | 0 | 7 | −3.0 |
| vomeronasal 1 receptor 232 | 0 | 7 | −3.0 |
| transmembrane protein 235 | 1 | 15 | −3.0 |
| formyl peptide receptor, related sequence 6 | 0 | 7 | −3.0 |
| zinc finger protein 456 | 0 | 7 | −3.0 |
| serine (or cysteine) peptidase inhibitor, clade B, member 1c | 0 | 7 | −3.0 |
| predicted gene 12838 | 0 | 7 | −3.0 |
| predicted gene 12006 | 0 | 7 | −3.0 |

Example 3—Identification of HG-NV Protein Composition

Figure 3A:
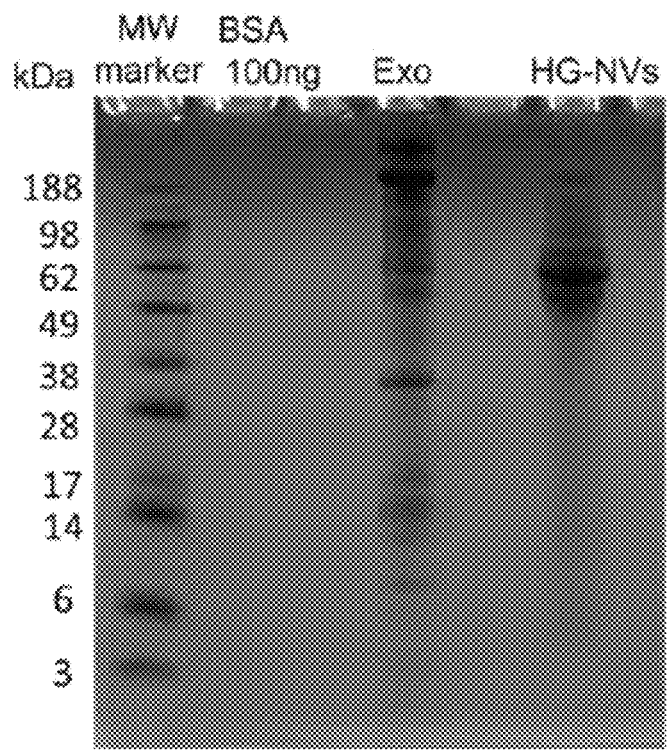
FIGS. 3A-3D include images and graphs showing the characterization of tumor cell derived HG-NV proteins, including.
Figure 3B:
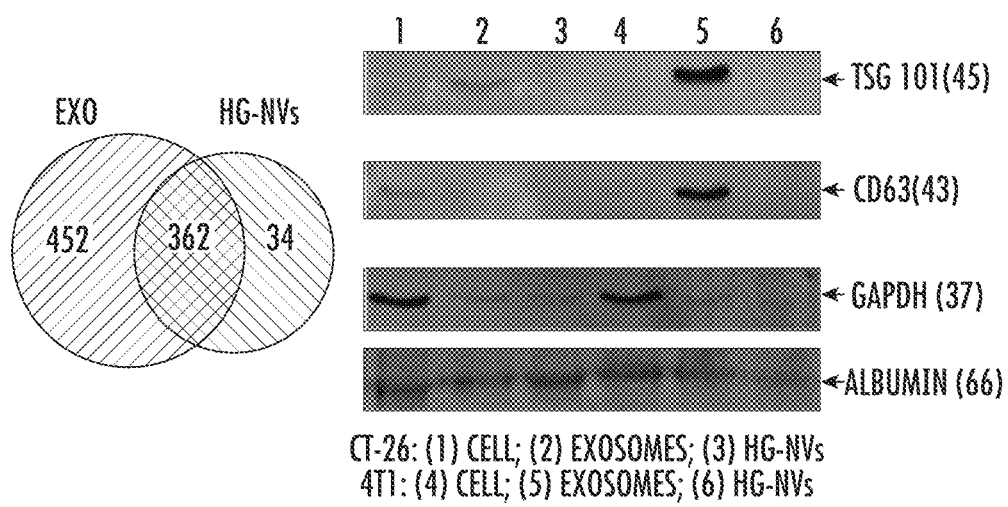

Shown in FIG. 3A (left panel) is the migration pattern of 4T1 EV proteins stained with Coomassie blue and Table 3a-3d is a listing of the proteins. A total of 848 proteins were identified in the 4T1 EV proteome. In general, many of the proteins identified contained two or more unique peptide hits. Table 3 contains detailed information on all of the proteins identified for exosomes and HG-NVs, including the number of unique peptides identified per protein. The pie chart (FIG. 3B, left panel) shows that of these proteins, 362 were common to both exosomes and HG-NVs. Furthermore a total of 452 unique proteins were identified in exosomes and 34 unique proteins were identified in HG-NVs (FIG. 3B, left panel). To validate the protein data generated from MS/MS analysis, a western blot analysis was performed on proteins that were randomly selected from the protein profile that were increased or decreased in HG-NVs in comparison with exosomes. Western blot analysis (FIG. 3B) indicated that both TSG101 and CD63, both of which are considered as exosomal markers, were enriched in exosomes. Albumin was detected in both the exosomes and HG-NVs, suggesting that an equal amount of protein was loaded which validates the western blot results. A higher level of GAPDH was detected in the cell lysates, suggesting that exosomes CD63 and Tsg101 are selectively sorted into the exosomes.

TABLE 3a

High-level protein detected in exosome of 4T-1 with proteomics analysis by HPLC-MS

| Identified Proteins | Access # | MW (kDa) | Counts |
|---|---|---|---|
| Basement membrane-specific heparan sulfate proteoglycan core protein | E9PZ16 | 470 | 184 |
| Anastellin | G5E8M2 | 263 | 171 |
| Gag-pro-pol polyprotein | Q1KYM2 | 194 | 82 |
| Serum albumin | P02769 | 69 | 62 |
| Programmed cell death 6-interacting protein | Q9WU78 | 96 | 46 |
| Filamin-A | Q8BTMB | 281 | 39 |
| Talin-1 | P26039 | 270 | 36 |
| Protein Ahnak | E9Q616 | 604 | 35 |
| Moesin | P26041 | 68 | 35 |
| Clathrin heavy chain 1 | Q68FD5 | 192 | 34 |
| Heat shock cognate 71 kDa protein | P63017 | 71 | 32 |
| Sodium/potassium-transporting ATPase subunit alpha | Q8VDN2 | 113 | 27 |
| Tubulointerstitial nephritis antigen-like | H3BJ97 | 49 | 24 |
| Milk fat globule-EGF factor 8 protein, isoform CRA_a | Q3TDU5 | 47 | 24 |
| Myosin-9 | Q8VDD5 | 226 | 23 |
| Unconventional myosin-Ic | Q9WTI7 | 122 | 22 |
| Melanome antigen | Q2HJ08 | 74 | 22 |
| EH domain-containing protein 2 | Q8BH64 | 61 | 22 |
| Annexin A5 | P48036 | 36 | 22 |
| Actin, cytoplasmic 1, N-terminally processed | F8WI82 | 42 | 22 |
| Vimentin | P20152 | 54 | 21 |
| Polyadenylate-binding protein 1 | P29341 | 71 | 21 |
| Integrin beta-1 | P09055 | 88 | 21 |
| Annexin A2 | P07356 | 39 | 21 |
| Pyruvate kinase isozymes M1/M2 | P52480 | 58 | 20 |
| Prostaglandin F2 receptor negative regulator | Q9WV91 | 99 | 20 |
| Annexin | Q3U5N9 | 39 | 20 |
| Thrombospondin-1 | P35441 | 130 | 19 |
| Integrin alpha-3 | Q62470 | 117 | 19 |
| Heat shock protein HSP 90-beta | P11499 | 83 | 19 |
| EH domain-containing protein 1 | Q9WVK4 | 61 | 19 |
| Ras GTPase-activating-like protein IQGAP1 | F6ZJB0 | 191 | 18 |
| Elongation factor 1-alpha 1 | P10126 | 50 | 18 |
| Collagen alpha-1(XII) chain | E9PX70 | 334 | 18 |
| 78 kDa glucose-regulated protein | P20029 | 72 | 18 |
| 14-3-3 protein zeta/delta | P63101 | 28 | 18 |
| Guanine nucleotide-binding protein G(i) subunit alpha-2 | P08752 | 40 | 17 |
| Elongation factor 2 | P58252 | 95 | 17 |
| ATP synthase subunit alpha, mitochondrial | Q03265 | 60 | 17 |
| Annexin A3 | O35639 | 36 | 17 |
| 4F2 cell-surface antigen heavy chain | P10852 | 58 | 17 |
| ATP synthase subunit beta, mitochondrial | P56480 | 56 | 16 |
| Tubulin alpha-1C chain | P68373 | 50 | 15 |
| Major vault protein | Q9EQK5 | 96 | 15 |
| Glypican-1 | Q9QZF2 | 61 | 15 |
| ADP/ATP translocase 1 | P48962 | 33 | 15 |
| Glyceraldehyde-3-phosphate dehydrogenase | E9PX42 | 36 | 14 |
| Erythrocyte band 7 integral membrane protein | P54116 | 31 | 14 |
| Ceruloplasmin, isoform CRA_a | G3X8Q5 | 124 | 14 |
| Annexin A11 | P97384 | 54 | 14 |
| Alpha-enolase | P17182 | 47 | 14 |
| 60 kDa heat shock protein, mitochondrial | P63038 | 61 | 14 |
| Voltage-dependent anion-selective channel protein 1 | Q60932 | 32 | 13 |
| Syntenin-1 | O08992 | 32 | 13 |
| Inactive lyrosine-protein kinase 7 | Q8BKG3 | 118 | 13 |
| Flotillin-1 | O08917 | 48 | 13 |
| Ephrin type-A receptor 2 | Q03145 | 109 | 13 |
| Endophilin-A2 | Q62419 | 42 | 13 |
| Tumor susceptibility gone 101 protein | Q61187 | 44 | 12 |
| Rep1A-retro1 | C5H0E8 | 21 | 12 |
| Keratin, type II cytoskeletal 5 | D3Z4Y4 | 60 | 12 |
| Complement C3 | P01027 | 186 | 12 |
| Chloride intracellular channel protein 1 | Q9Z1Q5 | 27 | 12 |
| Tubulin beta-6 chain | Q922F4 | 50 | 11 |
| Transforming protein RhoA | Q9QUI0 | 22 | 11 |
| Rab GDP dissociation inhibitor beta | Q61598 | 51 | 11 |

TABLE 3a-continued

High-level protein detected in exosome of 4T-1 with proteomics analysis by HPLC-MS

| Identified Proteins | Access # | MW (kDa) | Counts |
|---|---|---|---|
| Peptidyl-prolyl cis-trans isomerase | Q3UAJ1 | 18 | 11 |
| Malate dehydrogenase, mitochondrial | P08249 | 36 | 11 |
| Heat shock protein 9 | Q7TSZ0 | 73 | 11 |
| Galectin-3-binding protein | Q07797 | 64 | 11 |
| Fibulin 2, isoform CRA_c | G5E8B3 | 132 | 11 |
| Cytoplasmic dynein 1 heavy chain 1 | Q9JHU4 | 532 | 11 |
| Collagen alpha-2(IV) chain | P08122 | 167 | 11 |
| Collagen alpha-1(XVIII) chain | P39061 | 182 | 11 |
| Brain acid soluble protein 1 | Q91XV3 | 22 | 11 |
| Annexin A4 | P97429 | 38 | 11 |
| Aldehyde dehydrogenase, mitochondrial | P47738 | 57 | 11 |
| Vacuolar protein sorting-associated protein 28 homolog | Q9D1C8 | 25 | 10 |
| T-complex protein 1 subunit beta | P80314 | 57 | 10 |
| Putative helicase MOV-10 | D3YVL0 | 114 | 10 |
| Prohibitin | P67778 | 30 | 10 |
| Neutral amino acid transporter B(0) | E9PUM8 | 58 | 10 |
| Myofertin | Q69ZN7 | 233 | 10 |
| Long-chain-fatty-acid-CoA ligase 4 | Q9QUJ7 | 79 | 10 |
| Integrin alpha V | A2AKI5 | 112 | 10 |
| Immunoglobulin superfamily member 8 | Q8R368 | 65 | 10 |
| Basigin | P18572 | 42 | 10 |
| 40S ribosomal protein S3 | P62908 | 27 | 10 |
| 14-3-3 protein beta/alpha | Q9CQV8 | 28 | 10 |
| Vinculin | Q64727 | 117 | 9 |
| Vacuolar protein sorting-associated protein 37B | Q8R0J7 | 31 | 9 |
| Serine protease HTRA1 | Q9R116 | 51 | 9 |
| Ras-related protein Ral-B | Q9JIW9 | 23 | 9 |
| Prolow-density lipoprotein receptor-related protein | Q91ZX7 | 505 | 9 |
| Programmed cell death protein 6 | P12815 | 22 | 9 |
| Profilin-1 | P62962 | 15 | 9 |
| Polyubiquitin-C | PDCG50 | 83 | 9 |
| Poly(rC)-binding protein 2 | Q61990 | 38 | 9 |
| Peroxiredoxin-1 | P35700 | 22 | 9 |
| Keratin, type I cytoskeletal 14 | Q61781 | 53 | 9 |
| Integrin alpha 6 | Q8CC06 | 120 | 9 |
| Histone H2B type 1-F/J/L | P10853 | 14 | 9 |
| Ezrin | P26040 | 69 | 9 |
| EH domain-containing protein 4 | Q9EQP2 | 61 | 9 |
| Tyrosine-protein kinase Lyn | P25911 | 59 | 8 |
| Transgelin-2 | Q9WVA4 | 22 | 8 |
| Ras-related protein Rab-11B | P46638 | 24 | 8 |
| RAB14 protein | Q50HX0 | 24 | 8 |
| Protein Rab1 | H7BX41 | 22 | 8 |
| Protein Gm10119 | D3Z6C3 | 30 | 8 |
| Plexin-B2 | B2RXS4 | 206 | 8 |
| Multivesicular body subunit 12A | Q78HU3 | 29 | 8 |
| Monocarboxylate transporter 1 | P53986 | 53 | 8 |
| Integrin beta-3 | Q54890 | 87 | 8 |
| H-2 class I histocompatibility antigen, D-D alpha chain | P01900 | 41 | 8 |
| Guanine nucleotide-binding protein G(s) subunit alpha isoforms XLas | Q6R0H7 | 122 | 8 |
| Gap junction alpha-1 protein | P23242 | 43 | 8 |
| Fructose-bisphosphate aldolase A | P05064 | 39 | 8 |
| Flotillin 2 | Q5SS83 | 47 | 8 |
| DnaJ homolog subfamily A member 1 | P63037 | 45 | 8 |
| Coagulation factor V | O88783 | 247 | 8 |
| 60S ribosomal protein L7 | P14148 | 31 | 8 |
| 40S ribosomal protein S4, X isoform | Q545F8 | 28 | 8 |
| 40S ribosomal protein S2 | P25444 | 31 | 8 |
| 14-3-3 protein eta | P68510 | 28 | 8 |
| Phosphate carrier protein, mitochondrial | Q8VEM8 | 40 | 7 |
| Nras protein | Q4FJP3 | 22 | 7 |
| Nidogen-1 | P10493 | 137 | 7 |
| L-lactate dehydrogenase A chain | P06151 | 36 | 7 |
| Histone H2A type 1-F | Q8CGP5 | 14 | 7 |
| Guanine nucleotide binding protein, alpha 11 | Q91X95 | 42 | 7 |
| Glia-derived nexin | Q07235 | 44 | 7 |
| Galectin-1 | P16045 | 15 | 7 |
| Endoplasmin | P08113 | 92 | 7 |
| E3 ubiquitin-protein ligase Itchy | Q8C863 | 99 | 7 |
| Vacuolar protein sorting-associated protein 37C | Q8R105 | 38 | 7 |
| Sorting nexin-9 | Q91VH2 | 67 | 7 |
| Sorting nexin 18 | Q8C788 | 68 | 7 |
| Na/K-transporting ATPase subunit β-3 | P97370 | 32 | 7 |

TABLE 3a-continued

High-level protein detected in exosome of 4T-1 with proteomics analysis by HPLC-MS

| Identified Proteins | Access # | MW (kDa) | Counts |
|---|---|---|---|
| Ras-related protein Rap-2a | Q80ZJ1 | 21 | 7 |
| Ras-related protein Rab-5C | P35278 | 23 | 7 |
| Protein Gm10260 | F5H8M6 | 18 | 7 |
| Protein Fat1 | E9PYL7 | 508 | 7 |
| Protein Farp1 | F8VPU2 | 119 | 7 |
| Prohibitin-2 | E9Q313 | 20 | 7 |
| Phosphoglycerate mutase 1 | Q9DBJ1 | 29 | 7 |
| D-3-phosphoglycerate dehydrogenase | Q61753 | 57 | 7 |
| Cofilin-1 | P18760 | 19 | 7 |
| Charged multivesicular body protein 4b | Q9D8B3 | 25 | 7 |
| Chaperonin containing TCP-1 theta subunit | Q9WVS5 | 60 | 7 |
| Calnexin | P35564 | 67 | 7 |
| Basement membrane-specific heparan sulfate proteoglycan core protein | Q05793 | 398 | 7 |
| ATP synthase subunit O, mitochondrial | Q9DB20 | 23 | 7 |
| Aspartate aminotransferase, mitochondrial | P05202 | 47 | 7 |
| 60S acidic ribosomal protein P0 | P14869 | 34 | 7 |
| 60 kDa SS-A/Ro ribonucleoprotein | O08848 | 60 | 7 |
| 5'-nucleotidase | Q61503 | 64 | 7 |
| Ras-related protein Rab-2A | P53994 | 24 | 6 |
| Protein FAM49B | Q921M7 | 37 | 6 |
| Protein disulfide-isomerase A6 | Q3TML0 | 49 | 6 |
| Protein disulfide-isomerase A3 | P27773 | 57 | 6 |
| Phospholipid scramblase 3 | Q9JIZ9 | 32 | 6 |
| Phosphoglycerate kinase 1 | P09411 | 45 | 6 |
| Peroxidasin homolog | Q3UQ28 | 165 | 6 |
| Nucleoside diphosphate kinase B | Q01768 | 17 | 6 |
| Niban-like protein 1 | Q8R1F1 | 85 | 6 |
| Neutral amino acid transporter A | O35874 | 56 | 6 |
| Ubiquitin-like modifier-activating enzyme 1 | Q02053 | 118 | 6 |
| Triosephosphate isomerase | P17751 | 32 | 6 |
| Transferrin receptor protein 1 | Q62351 | 86 | 6 |
| T-complex protein 1 subunit zeta | P80317 | 58 | 6 |
| T-complex protein 1 subunit eta | P80313 | 60 | 6 |
| T-complex protein 1 subunit alpha | P11983 | 60 | 6 |
| Synaptosomal-associated protein 23 | O09044 | 23 | 6 |
| Synaptic vesicle membrane protein VAT-1 homolog | Q62465 | 43 | 6 |
| Succinyl-CoA:3-ketoacid-coenzyme A transferase 1, mitochondrial | Q3UJQ9 | 52 | 6 |
| S-methyl-5'-thioadenosine phosphorylase | Q9CQ65 | 31 | 6 |
| RuvB-like 1 | P60122 | 50 | 6 |
| Rps16 protein | Q5C2Y9 | 19 | 6 |
| Ras-related protein Rab-5A | Q9CQD1 | 24 | 6 |
| Map4k4 protein | B7ZNR9 | 138 | 6 |
| IST1 homolog | Q9CX00 | 39 | 6 |
| H-2K(D) antigen | O35641 | 41 | 6 |
| Glypican-4 | P51655 | 63 | 6 |
| Glutamate dehydrogenase 1, mitochondrial | P26443 | 61 | 6 |
| Glucose-6-phosphate isomerase | P06745 | 63 | 6 |
| Fumarate hydratase, mitochondrial | P97807 | 54 | 6 |
| Formin-like protein 2 | A2APV2 | 123 | 6 |
| Electron transfer flavoprotein subunit alpha, mitochondrial | Q99LC5 | 35 | 6 |
| EGF-like repeat and discoidin I-like domain-containing protein 3 | O35474 | 54 | 6 |
| Dolichyl-diphosphooligosaccharide-protein glycosyltransferase subunit 2 | A2ACG7 | 68 | 6 |
| Disks large homolog 1 | D3Z388 | 92 | 6 |
| Dihydropyrimidinase-related protein 2 | O08553 | 62 | 6 |
| Collagen alpha-1(IV) chain | P02463 | 161 | 6 |
| Clusterin | Q06890 | 52 | 6 |
| Bone morphogenetic protein 1 | P98063 | 112 | 6 |
| ATP citrate lyase | Q3V117 | 121 | 6 |
| Alpha-actinin-4 | P57780 | 105 | 6 |
| ADP-ribosylation factor 2 | Q8BSL7 | 21 | 6 |
| Adenosylhomocysteinase | P50247 | 48 | 6 |
| Actin-related protein 3 | Q99JY9 | 47 | 6 |
| 60S ribosomal protein L18 | Q642K1 | 22 | 6 |
| 3-hydroxyacyl-CoA dehydrogenase type-2 | A2AFQ2 | 28 | 6 |
| 14-3-3 protein theta | P68254 | 28 | 6 |

TABLE 3b

High-level protein detected in HG-NV of 4T-1 with proteomics analysis by HPLC-MS

| Identified Proteins | Access # | MW (kDa) | Counts |
|---|---|---|---|
| Anastellin | G5E8M2 | 263 | 188 |
| Basement membrane-specific heparan sulfate proteoglycan core protein | E9PZ16 | 470 | 168 |
| Serum albumin | P02769 | 69 | 162 |
| Collagen alpha-1(XII) chain | E9PX70 | 334 | 64 |
| Inter-alpha-trypsin inhibitor heavy chain H2 | Q61703 | 108 | 60 |
| Actin, cytoplasmic 1, N-terminally processed | F8WI82 | 42 | 52 |
| Heat shock cognate 71 kDa protein | P63017 | 71 | 44 |
| Thrombospondin-1 | P35441 | 130 | 44 |
| Programmed cell death 6-interacting protein | Q9WU78 | 96 | 40 |
| Talin-1 | P26039 | 270 | 36 |
| Complement C3 | P01027 | 186 | 32 |
| Gag-pro-pol polyprotein | Q1KYM2 | 194 | 28 |
| Prostaglandin F2 receptor negative regulalor | Q9WV91 | 99 | 28 |
| Heat shock protein HSP 90-beta | P11499 | 83 | 28 |
| Elongation factor 1-alpha 1 | P10126 | 50 | 28 |
| Ceruloplasmin, isoform CRA_a | G3X8Q5 | 124 | 28 |
| Proltow-density lipoprotein receptor-related protein 1 | Q91ZX7 | 505 | 24 |
| Histone H2A type 1-F | Q8CGP5 | 14 | 24 |
| Serotransferrin | Q921I1 | 77 | 24 |
| Insulin-like growth factor 2 receptor | B7ZWC4 | 274 | 24 |
| Titin | A2ASS6 | 3906 | 24 |
| Tubulointerstitial nephritis antigen-like | H3BJ97 | 49 | 20 |
| Melanoma antigen | Q2HJ08 | 74 | 20 |
| Integrin beta-1 | P09055 | 88 | 20 |
| Tubulin alpha-1C chain | P68373 | 50 | 20 |
| Keratin, type II cytoskeletal 5 | D3Z4Y4 | 60 | 20 |
| Vinculin | Q64727 | 117 | 20 |
| Serine protease HTRA1 | Q9R118 | 51 | 20 |
| Keratin, type I cytoskeletal 14 | Q61781 | 53 | 20 |
| Histone H2B type 1-F/J/L | P10853 | 14 | 20 |
| Clusterin | Q06890 | 52 | 20 |
| Keratin, type I cytoskeletal 10 | E9QLP8 | 49 | 20 |
| Heat shock protein HSP 90-alpha | P07901 | 85 | 20 |
| Protein Apob | E9Q414 | 509 | 20 |
| Inter-alpha-trypsin inhibitor heavy chain H3 | E9PVS1 | 78 | 20 |
| Apoa1 protein | Q58EV2 | 23 | 20 |
| 14-3-3 protein zeta/delta | P63101 | 28 | 16 |
| Alpha-enolase | P17182 | 47 | 16 |
| Chloride intracellular channel protein 1 | Q9Z1Q5 | 27 | 16 |
| Galactin-3-binding protein | Q07797 | 64 | 16 |
| 60S acidic ribosomal protein P0 | P14869 | 34 | 16 |
| Keratin, type II cytoskeletal 1 | P04104 | 66 | 16 |
| Krt2 protein | B2RTP7 | 71 | 16 |
| Antithrombin-III | P32261 | 52 | 16 |
| Serum albumin | P07724 | 69 | 16 |
| Type VI collagen alpha 3 subunit | O88493 | 287 | 16 |
| Thrombospondin-4 | Q9Z1T2 | 106 | 16 |
| Nucleophosmin | Q9DAY9 | 28 | 16 |
| Laminin B1 subunit 1 | B9EKB0 | 202 | 16 |
| Procollagen C-endopeptidase enhancer 1 | Q61398 | 50 | 16 |
| Insulin-like growth factor-binding protein 4 | P47879 | 26 | 16 |
| Collagen alpha-1(I) chain | P11087 | 138 | 16 |
| Milk fat globule-EGF factor 8 protein, isoform CRA_a | Q3TDU5 | 47 | 12 |
| Annexin A2 | P07358 | 39 | 12 |
| ATP synthase subunit beta, mitochondrial | P56480 | 56 | 12 |
| Glyceraldehyde-3-phosphate dehydrogenase | E9PX42 | 38 | 12 |
| Rap1A-retro1 | C5H0E8 | 21 | 12 |
| Cytoplasmic dynein 1 heavy chain 1 | Q9JHU4 | 532 | 12 |
| Collagen alpha-1(XVIII) chain | P39061 | 182 | 12 |
| Polyubiquitin-C | P0CG50 | 83 | 12 |
| Coagulation factor V | O88783 | 247 | 12 |
| Basement membrane-specific heparan sulfate proteoglycan core protein | Q05793 | 398 | 12 |
| Triosephosphate isomerase | P17751 | 32 | 12 |
| Adenosylhomocysteinase | P50247 | 48 | 12 |
| 60S ribosomal protein L18 | Q642K1 | 22 | 12 |
| Nucleolin | P09405 | 77 | 12 |
| 60S ribosomal protein L3 | P27659 | 46 | 12 |
| Alpha-2-macroglobulin-P | Q6GQT1 | 164 | 12 |
| 40S ribosomal protein S9 | D3YWH9 | 16 | 12 |
| Protein Pzp | D3YW52 | 167 | 12 |
| Laminin subunit alpha-5 | Q61001 | 404 | 12 |
| Collagen alpha-1(VI) chain | Q04857 | 108 | 12 |

TABLE 3b-continued

High-level protein detected in HG-NV of 4T-1 with proteomics analysis by HPLC-MS

| Identified Proteins | Access # | MW (kDa) | Counts |
|---|---|---|---|
| Beta-globin | A8DUN2 | 16 | 12 |
| Renin receptor | Q9CYN9 | 39 | 12 |
| Prothrombin | P19221 | 70 | 12 |
| Fibulin-1 | Q08879 | 78 | 12 |
| Bromodomain-containing protein 9 | Q3UQU0 | 67 | 12 |
| Beta-glucuronidase | P12265 | 74 | 12 |
| Abnormal spindle-like microcephaly-associated protein homolog | Q8CJ27 | 364 | 12 |
| Sister chromatid cohesion protein PDS5 homolog B | F8WHU5 | 165 | 12 |
| Inter alpha-trypsin inhibitor, heavy chain 4 | A6X935 | 100 | 12 |
| Keratin, type II cytoskeletal 2 oral | Q3UV17 | 63 | 8 |
| Glutaminyl-tRNA synthetase | Q8BML9 | 88 | 8 |
| E3 SUMO-protein ligase RanBP2 | Q9ERU9 | 341 | 8 |
| Complement component 4B (Childo blood group) | B2RWX2 | 193 | 8 |
| Complement C1q tumor necrosis factor-related protein 3 | D3YZ61 | 35 | 8 |
| Collagen alpha-2(I) chain | Q01149 | 130 | 8 |
| Citrate synthase | Q80X68 | 52 | 8 |
| Beta-2-microglobulin | P01887 | 14 | 8 |
| U2 snRNP-associated SURP motif-containing protein | Q6NV83 | 118 | 8 |
| Synaptonemal complex protein 1 | Q62209 | 116 | 8 |
| Spatacsin | Q3UHA3 | 274 | 8 |
| Sortilin-related receptor | O88307 | 247 | 8 |
| Ryanodine receptor 3 | A2AGL3 | 551 | 8 |
| Ryanodine receptor 2 | E9Q401 | 565 | 8 |
| Rho guanine nucleotide exchange factor 4 | E0CX56 | 68 | 8 |
| Sodium/potassium-transporting ATPase subunit alpha-1 | Q8VDN2 | 113 | 8 |
| Unconventional myosin-Ic | Q9WTI7 | 122 | 8 |
| Pyruvate kinase isozymes M1/M2 | P52480 | 58 | 8 |
| Integrin alpha-3 | Q62470 | 117 | 8 |
| 78 kDa glucose-regulated protein | P20029 | 72 | 8 |
| Annexin A3 | O35639 | 38 | 8 |
| Glypican-1 | Q9QZF2 | 61 | 8 |
| 60 kDa heat shock protein, mitochondrial | P63038 | 61 | 8 |
| Tubulin beta-6 chain | Q922F4 | 50 | 8 |
| Fibulin 2, isoform CRA_c | G5E8B3 | 132 | 8 |
| Collagen alpha-2(IV) chain | P08122 | 167 | 8 |
| Annexin A4 | P97429 | 36 | 8 |
| T-complex protein 1 subunit beta | P80314 | 57 | 8 |
| Profilin-1 | P62962 | 15 | 8 |
| Ras-related protein Rab-11B | P46638 | 24 | 8 |
| 40S ribosomal protein S2 | P25444 | 31 | 8 |
| Protein Fat1 | E9PYL7 | 506 | 8 |
| Glia-derived nexin | Q07235 | 44 | 8 |
| Cofilin-1 | P18760 | 19 | 8 |
| Collagen alpha-1(IV) chain | P02483 | 161 | 8 |
| Bone morphogenetic protein 1 | P98063 | 112 | 8 |
| Cell division control protein 42 homolog | Q3UL78 | 17 | 8 |
| 40S ribosomal protein SA | P14206 | 33 | 8 |
| Tubulin beta-3 chain | Q9ERD7 | 50 | 8 |
| Proteasome subunit alpha type-4 | Q9R1P0 | 29 | 8 |
| Proteasome subunit alpha type-2 | P49722 | 26 | 8 |
| Keratin, type II cytoskeletal 8 | P11679 | 55 | 8 |
| Ferritin | Q3TJJ6 | 21 | 8 |
| Pigment epithelium-derived factor | P97298 | 46 | 8 |
| Peptidyl-prolyl cis-trans isomerase B | P24369 | 24 | 8 |
| Histone H3 | F8WI35 | 15 | 8 |
| CD 81 antigen, isoform CRA_c | Q91V78 | 26 | 8 |
| Serine/arginine-rich-splicing factor 1 | H7BX95 | 28 | 8 |
| Regucalcin | Q64374 | 33 | 8 |
| Protein Krt78 | E9Q0F0 | 112 | 8 |
| Protein Hba-a1 | F7CAE1 | 15 | 8 |
| Proteasome subunit beta type-3 | Q9R1P1 | 23 | 8 |
| Proteasome subunit alpha type-3 | O70435 | 28 | 8 |
| Nascent polypeptide-associated complex subunit α, muscle-specific form | P70670 | 220 | 8 |
| Lumican | P51885 | 38 | 8 |
| Histone H2A | Q5NC91 | 9 | 8 |
| Gelsolin | P13020 | 86 | 8 |
| Try10-like trypsinogen | Q7M754 | 27 | 8 |
| Terminal uridytyltransferase 4 | B2RX14 | 185 | 8 |
| Proviral envelope protein | P97406 (+2) | 66 | 8 |
| Protein Trp53bp1 | A2AU91 | 213 | 8 |

TABLE 3b-continued

High-level protein detected in HG-NV of 4T-1 with proteomics analysis by HPLC-MS

| Identified Proteins | Access # | MW (kDa) | Counts |
|---|---|---|---|
| Osteopontin | F8WIP8 | 33 | 8 |
| Ninein-like protein | Q6ZQ12 | 158 | 8 |
| Keratin, type II cytoskeletal 73 | Q6NXH9 | 59 | 8 |
| Keratin, type II cytoskeletal 72 | Q6IME9 | 57 | 8 |
| Keratin, type II cytoskeletal 6A | P50448 | 59 | 8 |
| Regulator of G-protein-signaling 12 | E9Q652 | 157 | 8 |
| Putative rRNA methyltransferase 3 | Q9DBE9 | 96 | 7 |
| Proteoglycan 4 | E0CZ58 | 135 | 7 |
| Protein Zfp457 | E9PUC7 | 75 | 7 |
| Protein Zfp281 | Q99LI5 | 97 | 7 |
| Protein sprouty homolog 1 | Q9QXV9 | 34 | 7 |
| Protein Neb | E9Q1W3 | 829 | 7 |
| Protein Gm15800 | E9PX61 | 453 | 7 |
| Protein Fam38a | E9PY63 | 125 | 6 |
| Protein FAM205A | A2APU8 | 146 | 6 |
| Pecanex-like protein 1 | E9QPL4 | 248 | 6 |
| Pantetheinase | Q9Z0K8 | 57 | 6 |
| Olfactory receptor 303 | Q8VFP0 | 36 | 6 |
| Nipped-B-like protein | Q6KCD5 | 315 | 6 |
| Neurofilament heavy polypeptide | P19246 | 117 | 6 |
| Methyl-CpG-binding protein 2 | Q9Z2D6 | 52 | 6 |
| Lysosomal alpha-mannosidase | O09159 | 115 | 6 |
| Lysine-specific demethylase 2B | D3YVU4 (+2) | 146 | 6 |
| Lipoxygenase homology domain-containing | C8YR32 | 236 | 6 |
| Lactoferrin | B8YJF9 | 78 | 6 |
| Keratin, type I cytoskeletal 13 | P08730 | 48 | 6 |
| Homeobox protein unc-4 homolog | O08934 | 54 | 6 |
| Histone-lysine N-methyltransferase MLL | P55200 | 430 | 6 |
| E3 ubiquitin-protein ligase MIB1 | Q80SY4 | 110 | 6 |
| Delta-1-pyrroline-5-carboxylate synthase | Q9Z110 | 87 | 6 |
| Dedicator of cytokinesis protein 4 | F6SJX1 | 227 | 6 |
| Collagen alpha-2(XI) chain | Q64739 | 172 | 6 |
| Collagen alpha-1(III) chain | F6SIG2 | 115 | 6 |
| Coiled-coil domain-containing protein 38 | Q8CDN8 | 66 | 6 |
| Canalicular multispecific organic onion transporter 2 | B2RX12 | 169 | 6 |
| Cadherin-8 | E9PZC1 | 28 | 6 |
| Brain-specific angiogenesis inhibitor 3 | Q80ZF8 | 171 | 6 |
| Biglycan | P28653 | 42 | 6 |
| Anaphase-promoting complex subunit 7 | Q9WVM3 | 63 | 6 |
| AA987161 protein | Q80VN4 | 120 | 6 |

TABLE 3c

High-level protein detected in exosomes of MDA-MB-231 cell with proteomics analysis by HPLC-MS.

| Identified Proteins | Access # | MW (kDa) | Counts |
|---|---|---|---|
| Cytoplasmic dynein 1 heavy chain 1 | Q14204 | 532 | 152 |
| Filamin-A | P21333 | 281 | 85 |
| Plectin | Q15149 | 532 | 80 |
| Myosin-9 | P35579 | 227 | 75 |
| DNA-dependent protein kinase catalytic subunit | P78527 | 469 | 70 |
| Fatty acid synthase | P49327 | 273 | 68 |
| Talin-1 | Q9Y490 | 270 | 60 |
| Clathrin heavy chain 1 | Q00610 | 192 | 59 |
| Myoferlin | Q9NZM1 | 235 | 53 |
| Filamin B | B2ZZ83 | 282 | 47 |
| Filamin-C | Q14315 | 291 | 42 |
| Fibronectin | P02751 | 263 | 38 |
| Bifunctional glutamate/proline-tRNA ligase | P07814 | 171 | 38 |
| Basement membrane-specific heparan sulfate proteoglycan core protein | P98160 | 469 | 34 |
| Translational activator GCN1 | Q92618 | 293 | 33 |
| Pre-mRNA-processing-splicing factor 8 | Q6P2Q9 | 274 | 32 |
| Ras GTPase-activating-like protein IQGAP1 | P46940 | 189 | 30 |
| Heterogeneous nuclear ribonucleoprotein U | Q00839 | 91 | 28 |

TABLE 3c-continued

High-level protein detected in exosomes of MDA-MB-231 cell with proteomics analysis by HPLC-MS.

| Identified Proteins | Access # | MW (kDa) | Counts |
|---|---|---|---|
| E3 ubiquitin-protein ligase UBR4 | Q5T4S7 | 574 | 27 |
| Chaperonin containing TCP1, subunit 8 (Theta), isoform CRA_a | G5E9B2 | 59 | 27 |
| Programmed cell death 6-interacting protein | Q8WUM4 | 96 | 27 |
| Sodium/potassium-transporting ATPase subunit alpha-1 | P05023 | 113 | 27 |
| T-complex protein 1 subunit eta | Q99832 | 59 | 27 |
| Collagen alpha-1(XII) chain | Q99715 | 333 | 25 |
| Isoleucine-tRNA ligase, cytoplasmic | P41252 | 145 | 25 |
| Elongation factor 1-alpha 1 | P68104 | 50 | 25 |
| T-complex protein 1 subunit gamma | P49368 | 61 | 25 |
| EGF-like repeat and discoidin I-like domain-containing protein 3 | Q43854 | 54 | 25 |
| Annexin | A6NN80 | 75 | 24 |
| Leucine-tRNA ligase, cytoplasmic | Q9P2J5 | 134 | 23 |
| U5 small nuclear ribonucleoprotein 200 kDa helicase | O75643 | 245 | 22 |
| Proteasome-associated protein ECM29 homolog | Q5VYK3 | 204 | 22 |
| Kinesin-1 heavy chain | P33176 | 110 | 21 |
| E3 ubiquitin-protein ligase HUWE1 | Q7Z6Z7 | 482 | 20 |
| CAD protein | P27708 | 243 | 20 |
| Tenascin | P24821 | 241 | 20 |
| T-complex protein 1 subunit epsilon | P48643 | 60 | 20 |
| Elongation factor 1-gamma | P26641 | 50 | 20 |
| Neuroblast differentiation-associated protein AHNAK | Q09666 | 629 | 19 |
| T-complex protein 1 subunit zeta | P40227 | 68 | 19 |
| Valine--tRNA ligase | P26640 | 140 | 19 |
| T-complex protein 1 subunit delta | P50991 | 58 | 18 |
| C-1-tetrahydrofolate synthase, cytoplasmic | P11586 | 102 | 18 |
| Peroxidasin homolog | Q92626 | 165 | 17 |
| 26S protease regulatory subunit 7 | P35998 | 49 | 17 |
| High mobility group protein B1 | Q5T7C4 | 18 | 17 |
| Aspartate--tRNA ligase, cytoplasmic | P14868 | 57 | 17 |
| 40S ribosomal protein S4, X isoform | P62701 | 30 | 16 |
| Ribosome-binding protein 1 | Q9P2E9 | 152 | 16 |
| 40S ribosomal protein S3 | P23396 | 27 | 16 |
| 6-phosphofructokinase type C | Q01813 | 88 | 16 |
| Integrin beta-1 | P05556 | 88 | 16 |
| Spectrin alpha chain, brain | Q13813 | 285 | 15 |
| 26S proteasome non-ATPase regulatory subunit 11 | O00231 | 47 | 15 |
| 40S ribosomal protein S3a | P61247 | 30 | 15 |
| Laminin subunit bata-2 | P55268 | 196 | 15 |
| Heterogeneous nuclear ribonucleoprotein M | P52272 | 78 | 14 |
| DNA topoisomerase 2-alpha | P11388 | 174 | 14 |
| Peroxiredoxin-1 | Q06830 | 22 | 14 |
| 26S proteasome non-ATPase regulatory subunit 1 | Q99460 | 106 | 14 |
| Arginine-tRNA ligase, cytoplasmic | P54138 | 75 | 14 |
| Laminin subunit alpha-5 | O15230 | 400 | 14 |
| 26S protease regulatory subunit 6A | P17980 | 49 | 14 |
| Inosine-5'-monophosphate dehydrogenase 2 | P12268 | 56 | 14 |
| Microtubule-associated protein 1B | P46821 | 271 | 14 |
| Eukaryotic translation initiation factor 3 subunit B | P55884 | 92 | 14 |
| Poly [ADP-ribose] polymerase 1 | P09874 | 113 | 14 |
| Proteasome subunit alpha type-1 | P25786 | 30 | 14 |
| Cell growth inhibiting protein 40 | Q2TTR7 | 134 | 13 |
| Ras-related protein Rab-7a | P51149 | 23 | 13 |
| Elongation factor 1-delta | P29692 | 31 | 13 |
| Laminin subunit gamma-1 | P11047 | 178 | 13 |
| Cell growth inhibiting protein 40 | Q2TTR7 | 134 | 13 |
| Ras-related protein Rab-7a | P51149 | 23 | 13 |
| Elongation factor 1-delta | P29692 | 31 | 13 |
| Laminin subunit gamma-1 | P11047 | 178 | 13 |
| 26S protease regulatory subunit 10B | P62333 | 44 | 12 |
| DNA topoisomerase 1 | P11387 | 91 | 12 |
| Ephrin type-A receptor 2 | P29317 | 108 | 12 |
| Major vault protein | Q14764 | 99 | 12 |
| 60 heat shock protein, mitochondrial | P10809 | 61 | 12 |
| 26S protease regulatory subunit 8 | A8K3Z3 | 45 | 12 |
| Heterogeneous nuclear ribonucleoproteins C1/C2 | P07910 | 34 | 12 |
| RuvB-like 2 | Q9Y230 | 51 | 12 |
| 60S ribosomal protein L4 | P36578 | 48 | 11 |
| 60S ribosomal protein L4 | P36578 | 48 | 11 |
| Cation-independent mannose-6-phosphate receptor | P11717 | 274 | 11 |
| 40S ribosomal protein S6 | P62753 | 29 | 11 |
| 40S ribosomal protein S2 | P15880 | 31 | 11 |
| 26S protease regulatory subunit 4 | P62191 | 49 | 11 |

TABLE 3c-continued

High-level protein detected in exosomes of MDA-MB-231 cell with proteomics analysis by HPLC-MS.

| Identified Proteins | Access # | MW (kDa) | Counts |
|---|---|---|---|
| Ribosomal protein S27a | Q5RKT7 | 18 | 11 |
| Peptidyl-prolyl cis-trans isomerase FKBP4 | Q02790 | 52 | 11 |
| FACT complex subunit SPT16 | Q9Y5B9 | 120 | 11 |
| Spectrin beta chain, brain 1 | Q01082 | 275 | 11 |
| 40S ribosomal protein S7 | P82081 | 22 | 10 |
| Structural maintenance of chromosomes 3 | Q86VX4 | 142 | 10 |
| Protein DEK | P35659 | 43 | 10 |
| 78 glucose-regulated protein | P11021 | 72 | 10 |
| Aminoacyl tRNA synthase complex-interacting multifunctional protein 1 | Q12904 | 34 | 10 |
| Splicing factor 3B subunit 1 | O75533 | 146 | 10 |
| Glycine-tRNA ligase | P41250 | 83 | 10 |
| HSPC027 | Q9Y6E3 | 43 | 10 |
| Multifunctional protein ADE2 | P22234 | 47 | 10 |
| 14-3-3 protein theta | P27348 | 28 | 10 |
| Proteasome subunit alpha type-2 | P25787 | 26 | 10 |
| Eukaryotic translation initiation factor 3 subunit D | O15371 | 64 | 10 |
| Proteasome subunit beta type-4 | P28070 | 29 | 10 |
| Proteasome subunit beta type-5 | P28074 | 28 | 10 |
| 60S ribosomal protein L10 | P27635 | 25 | 9 |
| Mitochondrial import receptor subunit TOM34 | Q15785 | 35 | 9 |
| Peptidyl-prolyl cis-trans isomerase A | Q567Q0 | 11 | 9 |
| RNA-binding protein Raly | Q9UKM9 | 32 | 9 |
| Structural maintenance of chromosomes protein 4 | Q9NTJ3 | 147 | 9 |
| 60S ribosomal protein L23 | P62829 | 15 | 9 |
| Elongation factor Tu, mitochondrial | P49411 | 50 | 9 |
| Heterogeneous nuclear ribonucleoprotein A1 | P09651 | 39 | 9 |
| Plasma membrane calcium-transporting ATPase 1 | P20020 | 139 | 9 |
| 60S ribosomal protein L7 | P18124 | 29 | 9 |
| Eukaryotic translation initiation factor 2 subunit 1 | P05198 | 36 | 9 |
| Prolow-density lipoprotein receptor-related protein 1 | Q07954 | 505 | 9 |
| Glutamine-tRNA ligase | P47897 | 88 | 9 |
| HLA class I histocompatibility antigen, A-2 alpha chain | P01892 | 41 | 9 |
| Brain acid soluble protein 1 | P80723 | 23 | 9 |
| Cofilin-1 | P23528 | 19 | 9 |
| Triosephosphate isomerase | P60174 | 31 | 9 |
| 60S ribosomal protein L6 | Q02878 | 33 | 8 |
| Acetyl-CoA carboxylase 1 | Q13085 | 266 | 8 |
| Histone H4 | P62805 | 11 | 8 |
| Tropomyosin 3 | Q5VU58 | 29 | 8 |
| ATP synthase subunit beta, mitochondrial | P06578 | 57 | 8 |
| Disco-interacting protein 2 homolog B | Q9P265 | 171 | 8 |
| Lactadherin | Q08431 | 43 | 8 |
| Ras-related protein Rab-13 | P51153 | 23 | 8 |
| RPL14 protein | Q6IPH7 | 24 | 8 |
| Stress-induced-phosphoprotein 1 | P31948 | 63 | 8 |
| 26S proteasome non-ATPase regulatory subunit 12 | O00232 | 53 | 8 |
| 40S Ribosomal protein S9 | P46781 | 23 | 8 |
| 60S ribosomal protein L3 | P39023 | 48 | 8 |
| 60S ribosomal protein L5 | P46777 | 34 | 8 |
| Fermitin family homolog 3 | Q86UX7 | 76 | 8 |
| Galpha12 protein | Q6B6N3 | 42 | 8 |
| Histone H2B type 2-F | Q5QNW6 | 14 | 8 |
| Integrin alpha-6 | P23229 | 127 | 8 |
| Sequestosome-1 | Q13501 | 48 | 8 |
| Serine protease 23 | O95084 | 43 | 8 |
| Transforming protein RhoA | P61586 | 22 | 8 |
| 26S protease regulatory subunit 6B | P43686 | 47 | 8 |
| Asparagine-tRNA ligase, cytoplasmic | O43776 | 83 | 8 |
| Coatomer subunit beta | P53618 | 107 | 8 |
| Ferritin light chain | P02792 | 20 | 8 |
| Heterogeneous nuclear ribonucleoprotein D0 | Q14103 | 38 | 8 |
| Neutral alpha-glucosidase AB | Q14897 | 107 | 8 |
| Neutral amino acid transporter B(0) | Q15758 | 57 | 8 |
| Poly(rC)-binding protein 1 | Q15365 | 37 | 8 |
| Proliferation-associated protein 2G4 | Q9UQ80 | 44 | 8 |
| Proteasome subunit alpha type-3 | P25788 | 28 | 8 |
| Transferrin receptor protein 1 | P02786 | 85 | 8 |
| Activated RNA polymerase II transcriptional coactivator p15 | P53999 | 14 | 8 |
| Aminoacyl tRNA synthase complex-interacting multifunctional protein 2 | Q13155 | 35 | 8 |
| LAMA4 protein | Q5D044 | 202 | 8 |
| Proteasome subunit alpha type-4 | P25789 | 29 | 8 |
| 60S ribosomal protein L17 | P18621 | 21 | 7 |

TABLE 3c-continued

High-level protein detected in exosomes of MDA-MB-231 cell with proteomics analysis by HPLC-MS.

| Identified Proteins | Access # | MW (kDa) | Counts |
|---|---|---|---|
| 60S ribosomal protein L26 | P61254 | 17 | 7 |
| 60S ribosomal protein L28 | P46779 | 16 | 7 |
| Citron | Q2M5E1 | 237 | 7 |
| 60S ribosomal protein L13 | P28373 | 24 | 7 |
| Kinectin | Q86UP2 | 156 | 7 |
| Protein S100-AB | P06703 | 10 | 7 |
| Sorbitol dehydrogenase | Q00796 | 38 | 7 |
| Chloride intracellular channel protein 4 | Q9Y696 | 29 | 7 |
| Eukaryotic translation initiation factor 3 subunit E | P60228 | 52 | 7 |
| Guanine nucleotide-binding protein G(I)/G(S)/G(T) subunit beta-2 | P82879 | 37 | 7 |
| Integrin alpha-3 | P26008 | 117 | 7 |
| Malate dehydrogenase | Q6FHZ0 | 36 | 7 |
| Plasminogen activator inhibitor 1 | P05121 | 45 | 7 |
| Proteasome subunit beta type-2 | P49721 | 23 | 7 |
| Putative pre-mRNA-splicing factor ATP-dependent RNA helicase DHX15 | O43143 | 91 | 7 |
| Ras-related protein Rap-2b | P61225 | 21 | 7 |
| 60S acidic ribosomal protein P2 | P05387 | 12 | 7 |
| Heterogeneous nuclear ribonucleoprotein K | P61978 | 51 | 7 |
| Hsp90 co-chaperone Cdc37 | Q16543 | 44 | 7 |
| Myosin light polypeptide 6 | P60660 | 17 | 7 |
| Pre-mRNA-processing factor 19 | Q9UMS4 | 55 | 7 |
| Proteasome subunit beta type-1 | P20618 | 26 | 7 |
| Putative deoxyribose-phosphate aldolase | Q9Y315 | 35 | 7 |
| Stress-70 protein, mitochondrial | P38646 | 74 | 7 |
| Histone cluster 1, H1e | Q4VB24 | 22 | 7 |
| Myosin-10 | P35580 | 229 | 7 |
| Phenylalanine-tRNA ligase beta subunit | Q9NSD9 | 66 | 7 |
| Ras-related protein Rap-1b | P61224 | 21 | 7 |
| Sister chromatid cohesion protein PDS5 homolog A | O29RF7 | 151 | 7 |
| 40S ribosomal protein S8 | P62241 | 24 | 7 |
| 40S ribosomal protein SA | P08885 | 33 | 7 |
| 40S ribosomal protein S17-like | P0CW22 | 16 | 6 |
| 40S ribosomal protein S19 | P39019 | 16 | 6 |
| 60S ribosomal protein L13a | P40429 | 24 | 6 |
| 60S ribosomal protein L18 | F8VWC5 | 18 | 6 |
| 60S ribosomal protein L8 | P62917 | 28 | 6 |
| 60S ribosomal protein L9 | P32969 | 22 | 8 |
| BAG family molecular chaperone regulator 2 | O95818 | 24 | 8 |
| Calnexin | P27824 | 68 | 6 |
| Carboxypeptidase D | O75976 | 153 | 6 |
| DnaJ homolog subfamily C member 13 | O75185 | 254 | 6 |
| Kinase D-interacting substrate of 220 | Q9ULH0 | 197 | 6 |
| Neurogenic locus notch homolog protein 2 | Q04721 | 265 | 6 |
| Ras-related protein Rab-5C | P51148 | 23 | 6 |
| Receptor-type tyrosine-protein phosphatase F | P10586 | 213 | 6 |
| Serine/arginine-rich splicing factor 3 | P84103 | 19 | 6 |
| Slit homolog 2 protein | O94813 | 170 | 6 |
| Unconvensional myosin-Ic | O00159 | 122 | 6 |

TABLE 3d

High Expression in HG-NV of MDA-MB-231 cells with proteomics analysis by HPLC-MS.

| Identified Proteins | Access # | MW (kDa) | Counts |
|---|---|---|---|
| Serum albumin | P02769 | 69 | 74 |
| Vimenlin | P08670 | 54 | 47 |
| Heat shock cognate 71 kDa protein | P11142 | 71 | 35 |
| Keratin, type II cytoskeletal 1 | P04264 | 66 | 30 |
| Keratin, type II cytoskeletal 6B | P04259 | 60 | 25 |
| Keratin, type I cytoskeletal 16 | P08779 | 51 | 23 |
| Importin-5 | O00410 | 124 | 22 |
| Actinin alpha 1 isoform b | Q1HE25 | 106 | 21 |
| Keratin, type I cytoskeletal 10 | P13645 | 59 | 18 |
| Fructose-bisphosphate aldolase A | P04075 | 39 | 16 |
| Keratin, type I cytoskeletal 9 | P35527 | 62 | 16 |
| Exportin-2 | P55060 | 110 | 16 |
| Lysyl oxidase homolog 2 | Q9Y4K0 | 87 | 15 |
| X-ray repair cross-complementing protein 5 | P13010 | 83 | 15 |
| Pentraxin-retaled protein PTX3 | P26022 | 42 | 15 |
| Adenylyl cyclase-associated protein 1 | Q01518 | 52 | 15 |
| Amyloid-like protein 2 | Q08481 | 87 | 14 |
| Alpha-actinin-4 | O43707 | 105 | 14 |
| Keratin, type II cytoskeletal 2 epidermal | P35908 | 65 | 14 |
| Interleukin enhancer-binding factor 3 | Q12906 | 95 | 13 |
| Serine/threonine-protein phosphatase 2A 65 kDa regulatory subunit A alpha isoform | P30153 | 65 | 13 |
| 60S acidic ribosomal protein P0 | P05388 | 34 | 13 |
| ATP-dependent RNA helicase A | Q08211 | 141 | 13 |

TABLE 3d-continued

High Expression in HG-NV of MDA-MB-231 cells with proteomics analysis by HPLC-MS.

| Identified Proteins | Access # | MW (kDa) | Counts |
|---|---|---|---|
| Interstitial collagenase | P03956 | 54 | 11 |
| Keratin, type I cytoskeletal 14 | P02533 | 52 | 11 |
| Proteasome activator complex subunit 1 | Q08323 | 29 | 11 |
| Synoptic vesicle membrane protein VAT-1 homolog | Q99536 | 42 | 11 |
| Splicing factor 3B subunit 3 | Q15393 | 136 | 11 |
| WD repeat-containing protein 1 | O75083 | 66 | 11 |
| Vitamin D-binding protein | P02774 | 53 | 10 |
| Keratin, type II cytoskeletal 5 | P13647 | 62 | 10 |
| Keratin, type II cytoskeletal 8 | P05787 | 54 | 10 |
| Transformation-related protein 14 | Q597H1 | 43 | 10 |
| Heat shock 70 kDa protein 4 | P34932 | 94 | 10 |
| Heat shock protein 105 kDa | Q92598 | 97 | 10 |
| Heat shock protein 75 kDa, mitochondrial | Q12931 | 80 | 9 |
| Proactivator polypeptide | P07602 | 58 | 9 |
| von Willebrand factor | P04275 | 309 | 9 |
| Alpha-fetoprotein | P02771 | 69 | 9 |
| C99 | B4DII8 | 85 | 9 |
| COP9 signalosome complex subunit 3 | Q9UNS2 | 48 | 9 |
| Glycogen phosphorylase, brain form | P11216 | 97 | 9 |
| Malate dehydrogenase, cytoplasmic | P40925 | 36 | 9 |
| Periostin | Q15063 | 93 | 9 |
| 26S proteasome non-ATPase regulatory subunit 14 | O00487 | 35 | 9 |
| Acetyl-CoA acetyltransferase, cytosolic | Q9BWD1 | 41 | 9 |
| Cathepsin D | P07339 | 45 | 9 |
| Cytoplasmic dynein 1 light intermediate chain 1 | Q9Y8G9 | 57 | 9 |
| Cytosolic non-spedfic dipeptidase | Q96KP4 | 53 | 9 |
| Fascin | Q16658 | 55 | 9 |
| Nuclease-sensitive element-binding protein 1 | P67809 | 36 | 9 |
| Peroxiredoxin-6 | P30041 | 25 | 9 |
| Purine nucleoside phosphorylase | P00491 | 32 | 9 |
| Replication protein A 70 kDa DNA-binding subunit | P27694 | 68 | 9 |
| Vacuolar protein sorting-associated protein 28 homolog | Q9UK41 | 25 | 9 |
| 4-trimethylaminobutyraldehyde dehydrogenase | P49189 | 54 | 8 |
| ADAM metallopeptidase domain 30 | Q8TBZ7 | 69 | 8 |
| Heat shock 70 kDa protein 13 | P48723 | 52 | 8 |
| Histidine--tRNA ligase, cytoplasmic | P12081 | 57 | 8 |
| Keratin, type II cytoskeletal 6A | P02538 | 60 | 8 |
| Lactotransferrin | P02788 | 78 | 8 |
| Phosphoglucomutase-1 | P38871 | 81 | 8 |
| Probable serine carboxypeptidase CPVL | Q9H3G5 | 54 | 8 |
| Renin receptor | O75787 | 39 | 8 |
| Zinc finger FYVE domain-containing protein 1 | Q9HBF4 | 87 | 8 |
| Zinc finger protein RFP | P14373 | 58 | 8 |
| 60S acidic ribosomal protein P1 | P05386 | 12 | 8 |
| A-Kinase anchor protein 13 | H7BYL5 | 308 | 8 |
| Fumarata hydralase, mitochondrial | P07954 | 55 | 8 |
| Importin-9 | Q96P70 | 116 | 8 |
| Protein SET | Q01105 | 33 | 8 |
| Serglycin | P10124 | 18 | 8 |
| Titin | Q8WZ42 | 3816 | 8 |
| Urokinase-type plasminogen activator | P00749 | 49 | 8 |
| Very long-chain specific acyl-CoA dehydrogenase, mitochondrial | P49748 | 70 | 8 |
| Voltage-dependent R-type calcium channel subunit alpha-1E | Q15878 | 262 | 8 |

Figure 3C:
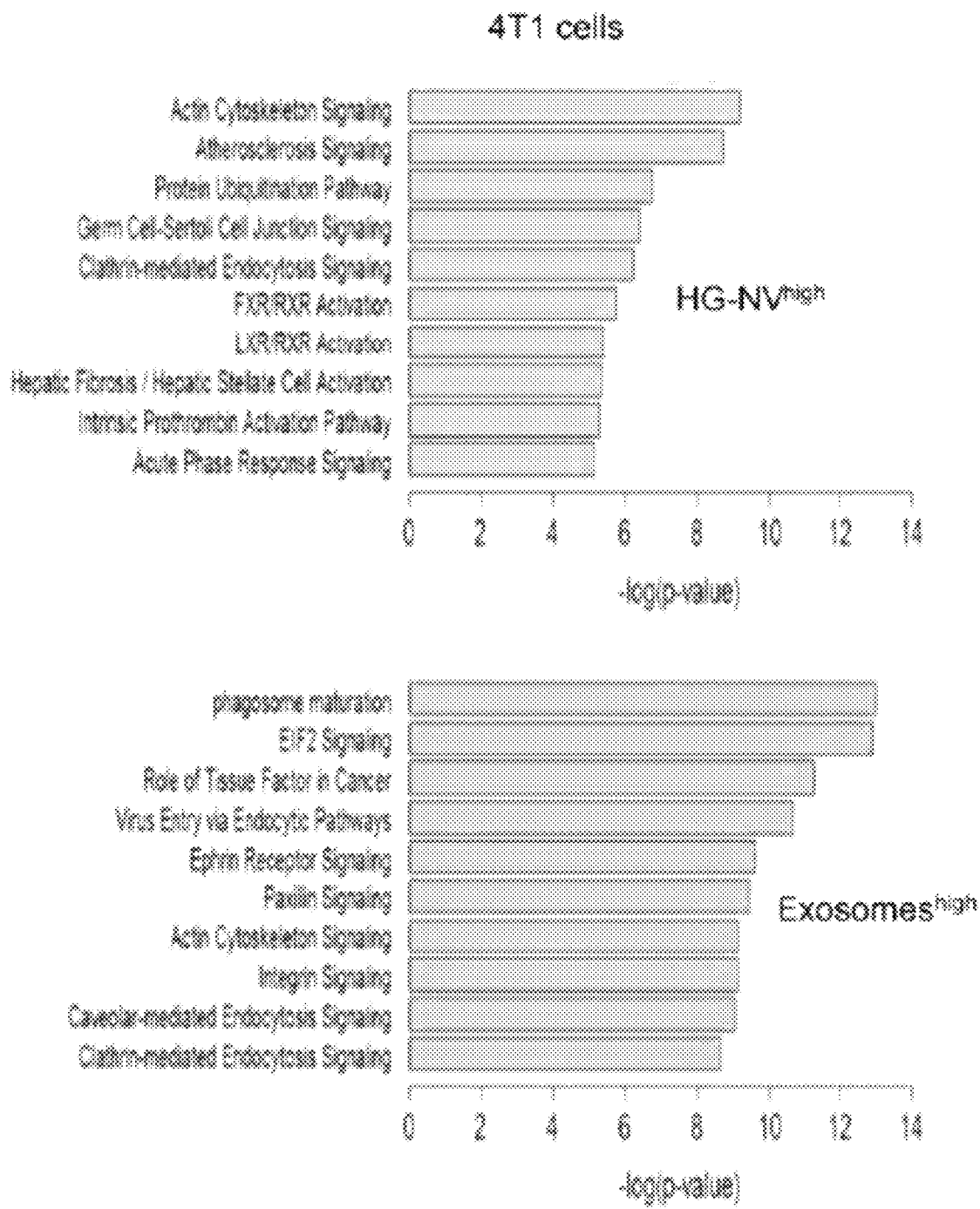

Using the IPA software, the proteins that are enriched in HG-NVs or exosomes were classified based on biological function. The top functions for HG-NV proteins (FIG. 3C, upper panel) are related to atherosclerosis signaling, ubiquitination and FXR/LXR/RXR mediated signaling pathways. The top functions for exosomal proteins are related to phagosome maturation and EIF2 signaling pathways (FIG. 3C, bottom panel). The clathrin-mediated endocytosis signaling pathway is common to both exosomes and HG-NVs.

Figure 3D:
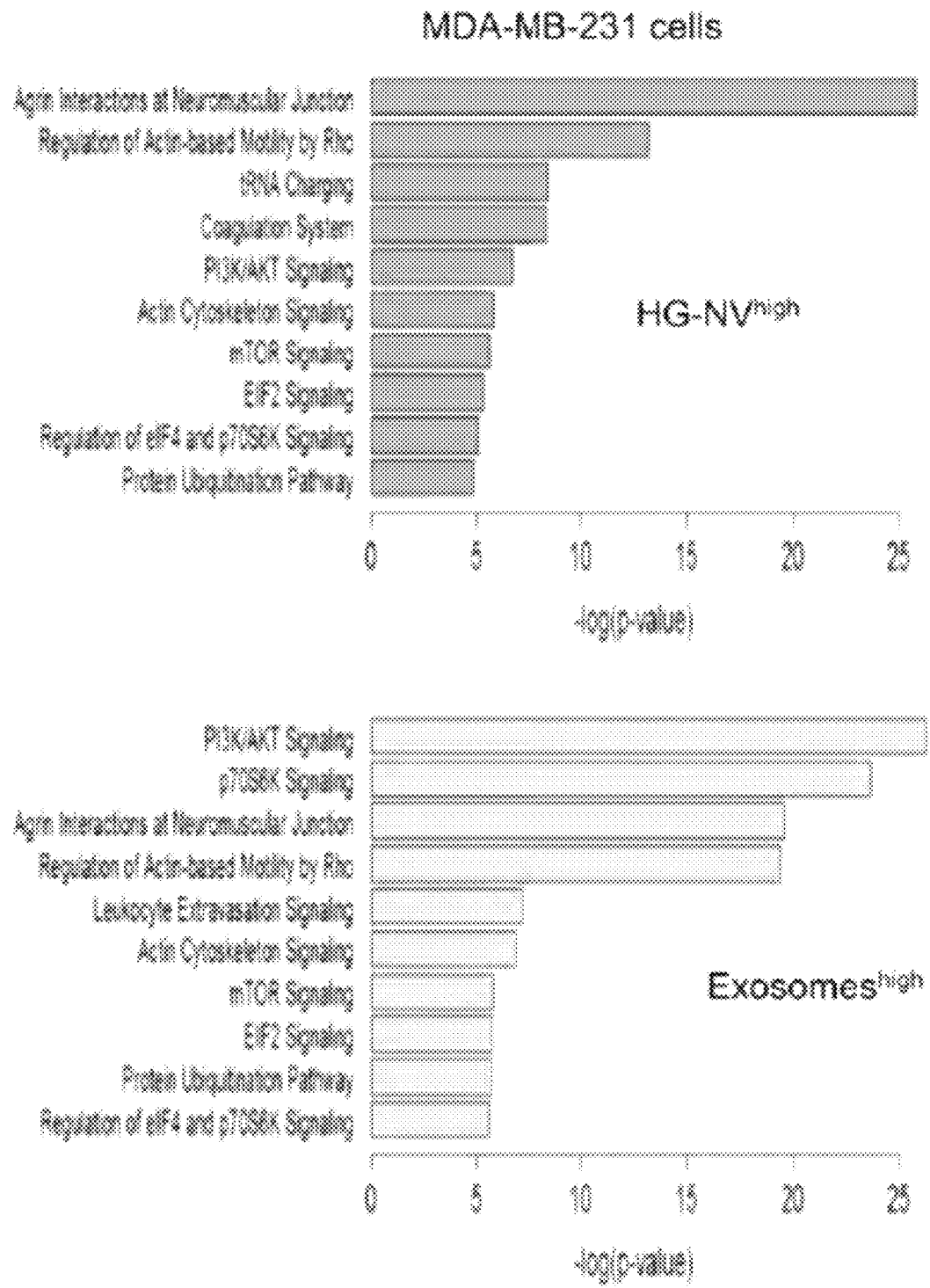

The proteins which were enriched in MDA-MB-231 HG-NVs or exosomes were also classified based on biological function. Tables 3c-3d contains detailed information on the proteins identified for MDA-MB-231 exosomes and HG-NVs, including the number of unique peptides identified per protein. The top functions for MDA-MB-231 HG-NV proteins (FIG. 3D, upper panel) were related to tRNA charging and the coagulation system; whereas the predominate function of MDA-MB-231 exosomes was linked to the PI3K and p70S6K mediated signaling pathways (FIG. 3D, bottom panel). Agrin interaction at neuromuscular junctions and actin-based mobility signaling pathways are common to both exosomes and HG-NVs.

Example 4—ESI-MS/MS Profiling and Quantitation of 4T1 EV Lipids

Figure 4A:
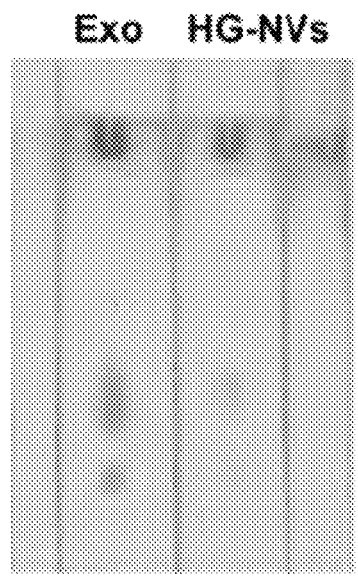
FIGS. 4A-4B include images and graphs showing the characterization of tumor cell derived HG-NV lipids, where lipids were detected by TLC analysis of the lipid extracts from 4T1 exosomes and HG-NV, and where the lipids extracted from 4T1 exosomes and HG-NV were separated on a thin-layer chromatography plate and developed by spraying the plate with a 10% copper sulfate and 8% phosphoric acid solution.
Figure 4B:
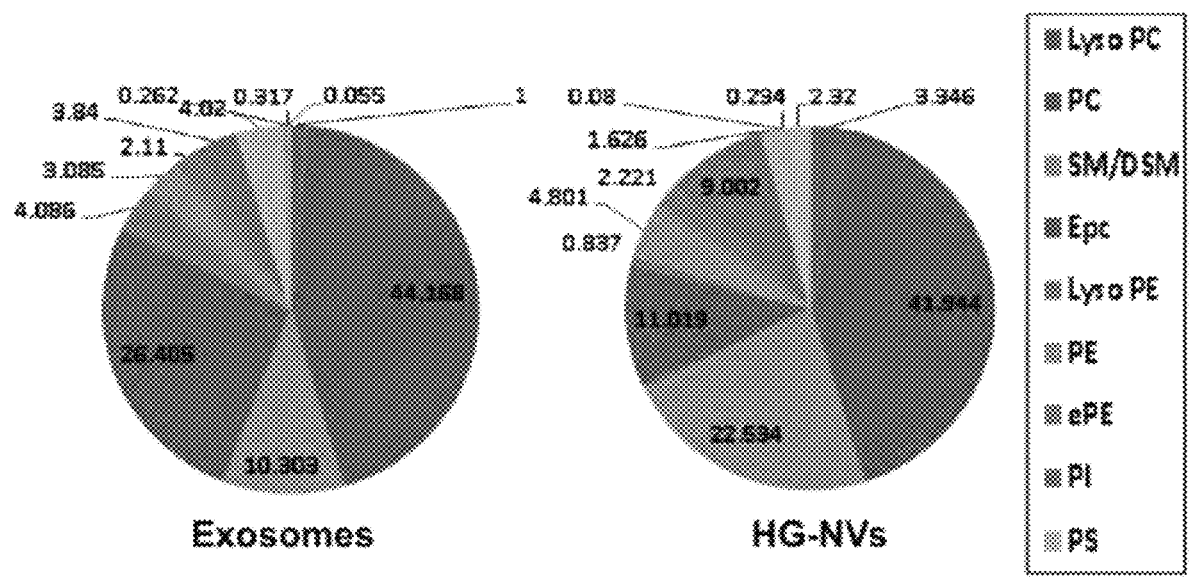

Electrospray ionization of crude lipid extracts (FIG. 4A) from 4T1 exosomes and HG-NVs resulted in the generation of single charged molecular ions with excellent concentration sensitivity. The molecular species of phospholipids present, i.e., PC, PE, PG, PI, PS, PA, lysoPC, and lysoPE, were identified (Table 4). The proportion of SM/DSM was twice as high in HG-NVs as in the exosomes; whereas, ePC was much lower in HG-NVs than in exosomes (FIG. 4B). An increase of PC and lysoPC and a decrease of lysoPE was observed in HG-NVs in comparison to exosomes (FIG. 4B).

TABLE 4

Identities of Lipids Detected in Exosome/HG-NV.

| Mass | Formula | Name | Exosomes | % by group HG-NV |
|---|---|---|---|---|
| 494.3 | C24H48O7PN | LPC(16:1) | 0.06 | 0.02 |
| 496.3 | C24H50O7PN | LPC(16:0) | 0.40 | 2.21 |
| 518.3 | C26H48O7PN | LPC(18:3) | 0.00 | 0.03 |
| 520.3 | C26H50O7PN | LPC(18:2) | 0.05 | 0.06 |
| 522.3 | C26H52O7PN | LPC(18:1) | 0.32 | 0.12 |
| 524.4 | C26H54O7PN | LPC(18:0) | 0.20 | 0.60 |
| 542.3 | C28H48O7PN | LPC(20:5) | 0.00 | 0.01 |
| 544.3 | C28H50O7PN | LPC(20:4) | 0.11 | 0.04 |
| 546.3 | C28H52O7PN | LPC(20:3) | 0.06 | 0.01 |
| 548.4 | C28H54O7PN | LPC(20:2) | 0.01 | 0.03 |
| 550.4 | C28H56O7PN | LPC(20:1) | 0.03 | 0.05 |
| 552.4 | C28H58O7PN | LPC(20:0) | 0.02 | 0.03 |
| 568.3 | C30H50O7PN | LPC(22:6) | 0.06 | 0.08 |
| 570.3 | C30H52O7PN | LPC(22:5) | 0.03 | 0.05 |
| Total LysoPC | | | 1.34 | 3.35 |
| 676.5 | C36H70O8PN | PC(28:1) | 0.05 | 0.19 |
| 704.5 | C38H74O8PN | PC(30:1) | 0.19 | 0.09 |
| 706.5 | C38H70O8PN | PC(30:0) | 1.93 | 0.87 |
| 730.5 | C40H76O8PN | PC(32:2) | 0.20 | 0.18 |
| 732.5 | C40H78O8PN | PC(32:1) | 3.24 | 0.98 |
| 734.6 | C40H80O8PN | PC(32:0) | 3.03 | 1.93 |
| 754.5 | C42H76O8PN | PC(34:4) | 0.03 | 0.25 |
| 756.5 | C42H78O8PN | PC(34:3) | 0.17 | 0.94 |
| 758.6 | C42H80O8PN | PC(34:2) | 1.57 | 2.05 |
| 760.6 | C42H82O8PN | PC(34:1) | 10.76 | 7.28 |
| 762.6 | C42H84O8PN | PC(34:0) | 1.11 | 0.60 |
| 778.5 | C44H76O8PN | PC(36:6) | 0.03 | 0.37 |
| 780.5 | C44H78O8PN | PC(36:5) | 0.13 | 1.60 |
| 782.6 | C44H80O8PN | PC(36:4) | 0.86 | 3.06 |
| 784.6 | C44H82O8PN | PC(36:3) | 0.93 | 1.58 |
| 786.6 | C44H84O8PN | PC(36:2) | 3.95 | 3.38 |
| 788.6 | C44H86O8PN | PC(36:1) | 5.74 | 3.90 |
| 790.6 | C44H88O8PN | PC(36:0) | 0.10 | 0.11 |
| 806.6 | C46H80O8PN | PC(38:6) | 0.31 | 0.45 |
| 808.6 | C46H82O8PN | PC(38:5) | 0.71 | 1.65 |
| 810.6 | C46H84O8PN | PC(38:4) | 2.06 | 3.39 |
| 812.6 | C46H86O8PN | PC(38:3) | 1.26 | 1.46 |
| 814.6 | C46H88O8PN | PC(38:2) | 0.62 | 0.55 |
| 816.6 | C46H90O8PN | PC(38:1) | 0.29 | 0.08 |

TABLE 4-continued

Identities of Lipids Detected in Exosome/HG-NV.

| Mass | Formula | Name | Exosomes | % by group HG-NV |
|---|---|---|---|---|
| 818.7 | C46H92O8PN | PC(38:0) | 0.31 | 0.07 |
| 830.6 | C48H80O8PN | PC(40:8) | 0.33 | 0.18 |
| 832.6 | C48H82O8PN | PC(40:7) | 0.07 | 0.23 |
| 834.6 | C48H84O8PN | PC(40:6) | 0.40 | 0.83 |
| 836.6 | C48H86O8PN | PC(40:5) | 0.40 | 1.04 |
| 838.6 | C48H88O8PN | PC(40:4) | 0.37 | 0.80 |
| 840.6 | C48H90O8PN | PC(40:3) | 0.14 | 0.00 |
| 842.7 | C48H92O8PN | PC(40:2) | 0.24 | 0.09 |
| 852.5 | C50H78O8PN | PC(42:11) | 0.08 | 0.19 |
| 854.6 | C50H80O8PN | PC(42:10) | 0.23 | 0.20 |
| 856.6 | C50H82O8PN | PC(42:9) | 1.03 | 0.39 |
| 858.6 | C50H84O8PN | PC(42:8) | 0.33 | 0.11 |
| 860.6 | C50H86O8PN | PC(42:7) | 0.03 | 0.09 |
| 862.6 | C50H88O8PN | PC(42:6) | 0.04 | 0.10 |
| 864.6 | C50H90O8PN | PC(42:5) | 0.06 | 0.05 |
| 866.7 | C50H92O8PN | PC(42:4) | 0.05 | 0.08 |
| 868.7 | C50H94O8PN | PC(42:3) | 0.18 | 0.11 |
| 870.7 | C50H96O8PN | PC(42:2) | 0.22 | 0.00 |
| 878.6 | C52H80O8PN | PC(44:12) | 0.05 | 0.07 |
| 880.6 | C52H82O8PN | PC(44:11) | 0.00 | 0.04 |
| 882.6 | C52H84O8PN | PC(44:10) | 0.06 | 0.08 |
| 884.6 | C52H86O8PN | PC(44:9) | 0.04 | 0.03 |
| 886.6 | C52H88O8PN | PC(44:8) | 0.00 | 0.04 |
| 888.6 | C52H90O8PN | PC(44:7) | 0.01 | 0.07 |
| 890.7 | C52H92O8PN | PC(44:6) | 0.02 | 0.00 |
| 892.7 | C52H94O8PN | PC(44:5) | 0.05 | 0.05 |
| 894.7 | C52H96O8PN | PC(44:4) | 0.05 | 0.01 |
| 896.7 | C52H98O8PN | PC(44:3) | 0.06 | 0.02 |
| 898.7 | C52H100O8PN | PC(44:2) | 0.06 | 0.02 |
| Total PC | | | 44.17 | 41.94 |
| 701.5 | C39H77N2O6P | SM(16:1) | 0.68 | 0.54 |
| 703.6 | C39H79N2O6P | SM(16:0) | 4.41 | 8.76 |
| 705.6 | C39H81N2O6P | DSM(16:0) | 0.04 | 0.79 |
| 729.6 | C41H81N2O6P | SM(18:1) | 0.21 | 0.50 |
| 731.6 | C41H83N2O6P | SM(18:0) | 0.00 | 1.88 |
| 733.6 | C41H85N2O6P | DSM(18:0) | 0.00 | 0.08 |
| 785.6 | C45H89N2O6P | SM(22:1) | 0.00 | 0.08 |
| 787.7 | C45H91N2O6P | SM(22:0) | 0.00 | 2.44 |
| 789.7 | C45H93N2O6P | DSM(22:0) | 0.00 | 0.00 |
| 813.7 | C47H93N2O6P | SM(24:1) | 3.56 | 4.50 |
| 815.7 | C47H95N2O6P | SM(24:0) | 1.41 | 2.66 |
| 817.7 | C47H97N2O6P | DSM(24:0) | 0.00 | 0.29 |
| Total SM and DSM | | | 10.30 | 22.53 |
| 714.5 | C40H76O7PN | ePC(32:3) | 0.17 | 0.07 |
| 716.6 | C40H78O7PN | ePC(32:2) | 0.08 | 0.01 |
| 718.6 | C40H80O7PN | ePC(32:1) | 1.76 | 0.37 |
| 720.6 | C40H82O7PN | ePC(32:0) | 1.51 | 0.54 |
| 740.6 | C42H78O7PN | ePC(34:4) | 0.02 | 0.10 |
| 742.6 | C42H80O7PN | ePC(34:3) | 0.09 | 0.07 |
| 744.6 | C42H82O7PN | ePC(34:2) | 0.72 | 0.24 |
| 746.6 | C42H84O7PN | ePC(34:1) | 6.41 | 1.71 |
| 748.6 | C42H86O7PN | ePC(34:0) | 1.32 | 0.39 |
| 766.6 | C44H80O7PN | ePC(36:5) | 0.59 | 0.22 |
| 768.6 | C44H82O7PN | ePC(36:4) | 0.36 | 0.25 |
| 770.6 | C44H84O7PN | ePC(36:3) | 0.64 | 0.30 |
| 772.6 | C44H86O7PN | ePC(36:2) | 1.48 | 0.52 |
| 774.6 | C44H88O7PN | ePC(36:1) | 1.66 | 1.10 |
| 776.6 | C44H90O7PN | ePC(36:0) | 0.18 | 0.30 |
| 792.6 | C46H82O7PN | ePC(38:6) | 0.79 | 0.25 |
| 794.6 | C46H84O7PN | ePC(38:5) | 2.04 | 0.75 |
| 796.6 | C46H86O7PN | ePC(38:4) | 1.71 | 0.61 |
| 798.6 | C46H88O7PN | ePC(38:3) | 0.54 | 0.28 |
| 800.6 | C46H90O7PN | ePC(38:2) | 0.41 | 0.63 |
| 802.7 | C46H92O7PN | ePC(38:1) | 0.34 | 0.46 |
| 804.7 | C46H94O7PN | ePC(38:0) | 0.10 | 0.19 |
| 820.6 | C48H86O7PN | ePC(40:6) | 1.86 | 0.55 |
| 822.6 | C48H88O7PN | ePC(40:5) | 1.05 | 0.49 |
| 824.6 | C48H90O7PN | ePC(40:4) | 0.19 | 0.20 |
| 826.7 | C48H92O7PN | ePC(40:3) | 0.13 | 0.23 |
| 828.7 | C48H94O7PN | ePC(40:2) | 0.24 | 0.21 |
| Total ePC | | | 26.40 | 11.02 |
| 452.3 | C21H42O7PN | LPE(16:1) | 0.11 | 0.04 |
| 454.3 | C21H44O7PN | LPE(16:0) | 0.12 | 0.47 |
| 476.3 | C23H42O7PN | LPE(18:3) | 0.00 | 0.03 |
| 478.3 | C23H44O7PN | LPE(18:2) | 0.06 | 0.00 |
| 480.3 | C23H46O7PN | LPE(18:1) | 1.92 | 0.16 |
| 500.3 | C25H42O7PN | LPE(20:5) | 0.00 | 0.02 |
| 502.3 | C25H44O7PN | LPE(20:4) | 0.49 | 0.00 |
| 504.3 | C25H46O7PN | LPE(20:3) | 0.21 | 0.00 |
| 506.3 | C25H48O7PN | LPE(20:2) | 0.12 | 0.00 |
| 508.3 | C25H50O7PN | LPE(20:1) | 0.33 | 0.05 |
| 510.3 | C25H52O7PN | LPE(20:0) | 0.01 | 0.02 |
| 526.3 | C27H44O7PN | LPE(22:6) | 0.34 | 0.01 |
| 528.3 | C27H46O7PN | LPE(22:5) | 0.38 | 0.03 |
| Total LysoPE | | | 4.09 | 0.84 |
| 634.4 | C33H64O8PN | PE(28:1) | 0.00 | 0.00 |
| 636.5 | C33H66O8PN | PE(28:0) | 0.00 | 0.05 |
| 662.5 | C35H68O8PN | PE(30:1) | 0.00 | 0.24 |
| 664.5 | C35H70O8PN | PE(30:0) | 0.00 | 0.63 |
| 688.5 | C37H70O8PN | PE(32:2) | 0.00 | 0.68 |
| 690.5 | C37H72O8PN | PE(32:1) | 0.05 | 1.05 |
| 692.5 | C37H74O8PN | PE(32:0) | 0.01 | 0.08 |
| 712.5 | C39H70O8PN | PE(34:4) | 0.01 | 0.03 |
| 714.5 | C39H72O8PN | PE(34:3) | 0.01 | 0.11 |
| 716.5 | C39H74O8PN | PE(34:2) | 0.11 | 1.02 |
| 718.5 | C39H76O8PN | PE(34:1) | 0.33 | 0.29 |
| 720.5 | C39H78O8PN | PE(34:0) | 0.00 | 0.00 |
| 736.5 | C41H70O8PN | PE(36:6) | 0.00 | 0.00 |
| 738.5 | C41H72O8PN | PE(36:5) | 0.01 | 0.01 |
| 740.5 | C41H74O8PN | PE(36:4) | 0.05 | 0.10 |
| 742.5 | C41H76O8PN | PE(36:3) | 0.10 | 0.06 |
| 744.5 | C41H78O8PN | PE(36:2) | 0.63 | 0.24 |
| 746.6 | C41H80O8PN | PE(36:1) | 0.50 | 0.05 |
| 748.6 | C41H82O8PN | PE(36:0) | 0.00 | 0.00 |
| 764.5 | C43H74O8PN | PE(38:6) | 0.03 | 0.00 |
| 766.5 | C43H76O8PN | PE(38:5) | 0.11 | 0.00 |
| 768.5 | C43H78O8PN | PE(38:4) | 0.31 | 0.04 |
| 770.6 | C43H80O8PN | PE(38:3) | 0.22 | 0.01 |
| 772.6 | C43H82O8PN | PE(38:2) | 0.11 | 0.01 |
| 774.6 | C43H84O8PN | PE(38:1) | 0.01 | 0.00 |
| 776.6 | C43H86O8PN | PE(38:0) | 0.04 | 0.00 |
| 788.5 | C45H74O8PN | PE(40:8) | 0.02 | 0.00 |
| 790.5 | C45H76O8PN | PE(40:7) | 0.03 | 0.00 |
| 792.5 | C45H78O8PN | PE(40:6) | 0.06 | 0.01 |
| 794.6 | C45H80O8PN | PE(40:5) | 0.09 | 0.01 |
| 796.6 | C45H82O8PN | PE(40:4) | 0.12 | 0.02 |
| 798.6 | C45H84O8PN | PE(40:3) | 0.04 | 0.00 |
| 800.6 | C45H86O8PN | PE(40:2) | 0.02 | 0.00 |
| 812.5 | C47H74O8PN | PE(42:10) | 0.00 | 0.00 |
| 814.5 | C47H76O8PN | PE(42:9) | 0.00 | 0.00 |
| 816.5 | C47H78O8PN | PE(42:8) | 0.00 | 0.00 |
| 818.6 | C47H80O8PN | PE(42:7) | 0.00 | 0.00 |
| 820.6 | C47H82O8PN | PE(42:6) | 0.01 | 0.01 |
| 822.6 | C47H84O8PN | PE(42:5) | 0.00 | 0.00 |
| 824.6 | C47H86O8PN | PE(42:4) | 0.00 | 0.00 |
| 826.6 | C47H88O8PN | PE(42:3) | 0.03 | 0.00 |
| 828.6 | C47H90O8PN | PE(42:2) | 0.02 | 0.00 |
| 836.5 | C49H74O8PN | PE(44:12) | 0.00 | 0.00 |
| 838.5 | C49H76O8PN | PE(44:11) | 0.00 | 0.00 |
| 840.5 | C49H78O8PN | PE(44:10) | 0.00 | 0.00 |
| 842.6 | C49H80O8PN | PE(44:9) | 0.00 | 0.00 |
| 844.6 | C49H82O8PN | PE(44:8) | 0.00 | 0.00 |
| 846.6 | C49H84O8PN | PE(44:7) | 0.00 | 0.00 |
| 848.6 | C49H86O8PN | PE(44:6) | 0.00 | 0.00 |

TABLE 4-continued

Identities of Lipids Detected in Exosome/HG-NV.

| Mass | Formula | Name | Exosomes | % by group HG-NV |
|---|---|---|---|---|
| 850.6 | C49H88O8PN | PE(44:5) | 0.00 | 0.00 |
| 852.6 | C49H90O8PN | PE(44:4) | 0.00 | 0.00 |
| 854.7 | C49H92O8PN | PE(44:3) | 0.00 | 0.00 |
| 856.7 | C49H94O8PN | PE(44:2) | 0.00 | 0.00 |
| Total PE | | | 3.09 | 4.80 |
| 659.5 | C36H71O6PN2 | PE-Cer(16:1) | 0.00 | 0.00 |
| 661.5 | C36H73O6PN2 | PE-Cer(16:0) | 0.00 | 0.00 |
| 687.5 | C38H75O6PN2 | PE-Cer(18:1) | 0.00 | 0.03 |
| 689.5 | C38H77O6PN2 | PE-Cer(18:0) | 0.00 | 0.00 |
| 773.6 | C44H89O6PN2 | PE-Cer(24:0) | 0.00 | 0.00 |
| Total PE-Cer | | | 0.00 | 0.04 |
| 672.5 | C37H70O7PN | ePE(32:3) | 0.00 | 0.00 |
| 674.5 | C37H72O7PN | ePE(32:2) | 0.00 | 0.10 |
| 676.5 | C37H74O7PN | ePE(32:1) | 0.03 | 1.15 |
| 678.5 | C37H76O7PN | ePE(32:0) | 0.00 | 0.22 |
| 698.5 | C39H72O7PN | ePE(34:4) | 0.00 | 0.00 |
| 700.5 | C39H74O7PN | ePE(34:3) | 0.00 | 0.00 |
| 702.5 | C39H76O7PN | ePE(34:2) | 0.04 | 0.25 |
| 704.6 | C39H78O7PN | ePE(34:1) | 0.26 | 0.28 |
| 706.6 | C39H80O7PN | ePE(34:0) | 0.00 | 0.00 |
| 724.5 | C41H74O7PN | ePE(36:5) | 0.01 | 0.00 |
| 726.5 | C41H76O7PN | ePE(36:4) | 0.04 | 0.00 |
| 728.6 | C41H78O7PN | ePE(36:3) | 0.03 | 0.04 |
| 730.6 | C41H80O7PN | ePE(36:2) | 0.32 | 0.07 |
| 732.6 | C41H82O7PN | ePE(36:1) | 0.26 | 0.04 |
| 734.6 | C41H84O7PN | ePE(36:0) | 0.01 | 0.01 |
| 750.5 | C43H76O7PN | ePE(38:6) | 0.05 | 0.00 |
| 752.6 | C43H78O7PN | ePE(38:5) | 0.17 | 0.01 |
| 754.6 | C43H80O7PN | ePE(38:4) | 0.20 | 0.01 |
| 756.6 | C43H82O7PN | ePE(38:3) | 0.10 | 0.01 |
| 758.6 | C43H84O7PN | ePE(38:2) | 0.07 | 0.01 |
| 760.6 | C43H86O7PN | ePE(38:1) | 0.08 | 0.00 |
| 762.6 | C43H88O7PN | ePE(38:0) | 0.01 | 0.00 |
| 778.6 | C45H80O7PN | ePE(40:6) | 0.12 | 0.00 |
| 780.6 | C45H82O7PN | ePE(40:5) | 0.12 | 0.01 |
| 782.6 | C45H84O7PN | ePE(40:4) | 0.10 | 0.00 |
| 784.6 | C45H86O7PN | ePE(40:3) | 0.06 | 0.00 |
| 786.6 | C45H88O7PN | ePE(40:2) | 0.03 | 0.00 |
| Total ePE | | | 2.11 | 2.22 |
| 848.5 | C43H75O13P | PI(34:4) | 0.00 | 0.03 |
| 850.5 | C43H77O13P | PI(34:3) | 0.03 | 0.56 |
| 852.5 | C43H79O13P | PI(34:2) | 0.15 | 3.01 |
| 854.5 | C43H81O13P | PI(34:1) | 0.15 | 1.03 |
| 872.5 | C45H75O13P | PI(36:6) | 0.00 | 0.03 |
| 874.5 | C45H77O13P | PI(36:5) | 0.00 | 0.25 |
| 876.5 | C45H79O13P | PI(36:4) | 0.07 | 0.82 |
| 878.5 | C45H81O13P | PI(36:3) | 0.07 | 0.52 |
| 880.6 | C45H83O13P | PI(36:2) | 0.39 | 0.84 |
| 882.6 | C45H85O13P | PI(36:1) | 0.13 | 0.29 |
| 900.5 | C47H79O13P | PI(38:6) | 0.00 | 0.00 |
| 902.6 | C47H81O13P | PI(38:5) | 0.11 | 0.06 |
| 904.6 | C47H83O13P | PI(38:4) | 1.37 | 0.43 |
| 906.6 | C47H85O13P | PI(38:3) | 0.92 | 0.25 |
| 908.6 | C47H87O13P | PI(38:2) | 0.22 | 0.06 |
| 910.6 | C47H89O13P | PI(38:1) | 0.00 | 0.01 |
| 912.6 | C47H91O13P | PI(38:0) | 0.00 | 0.00 |
| 924.5 | C49H79O13P | PI(40:8) | 0.00 | 0.00 |
| 926.5 | C49H81O13P | PI(40:7) | 0.00 | 0.00 |
| 928.6 | C49H83O13P | PI(40:6) | 0.00 | 0.00 |
| 930.6 | C49H85O13P | PI(40:5) | 0.03 | 0.03 |
| 932.6 | C49H87O13P | PI(40:4) | 0.06 | 0.02 |
| 934.6 | C49H89O13P | PI(40:3) | 0.02 | 0.00 |
| 936.6 | C49H91O13P | PI(40:2) | 0.00 | 0.00 |
| 938.6 | C49H93O13P | PI(40:1) | 0.00 | 0.00 |
| 940.7 | C49H95O13P | PI(40:0) | 0.05 | 0.45 |
| 948.5 | C51H79O13P | PI(42:10) | 0.00 | 0.00 |
| 950.5 | C51H81O13P | PI(42:9) | 0.00 | 0.00 |
| 952.6 | C51H83O13P | PI(42:8) | 0.00 | 0.00 |
| 954.6 | C51H85O13P | PI(42:7) | 0.00 | 0.01 |
| 956.6 | C51H87O13P | PI(42:6) | 0.00 | 0.00 |
| 958.6 | C51H89O13P | PI(42:5) | 0.01 | 0.22 |
| 960.6 | C51H91O13P | PI(42:4) | 0.00 | 0.00 |
| 962.6 | C51H93O13P | PI(42:3) | 0.06 | 0.07 |
| 964.7 | C51H95O13P | PI(42:2) | 0.00 | 0.01 |
| 972.5 | C53H79O13P | PI(44:12) | 0.00 | 0.00 |
| 974.5 | C53H81O13P | PI(44:11) | 0.00 | 0.00 |
| 976.6 | C53H83O13P | PI(44:10) | 0.00 | 0.00 |
| 978.6 | C53H85O13P | PI(44:9) | 0.00 | 0.00 |
| 980.6 | C53H87O13P | PI(44:8) | 0.00 | 0.00 |
| 982.6 | C53H89O13P | PI(44:7) | 0.00 | 0.01 |
| 984.6 | C53H91O13P | PI(44:6) | 0.00 | 0.00 |
| 986.6 | C53H93O13P | PI(44:5) | 0.00 | 0.00 |
| 988.7 | C53H95O13P | PI(44:4) | 0.00 | 0.00 |
| 990.7 | C53H97O13P | PI(44:3) | 0.00 | 0.00 |
| 992.7 | C53H99O13P | PI(44:2) | 0.00 | 0.00 |
| Total PI | | | 3.84 | 9.00 |
| 734.5 | C38H72O10PN | PS(32:1) | 0.03 | 0.21 |
| 736.5 | C38H74O10PN | PS(32:0) | 0.03 | 0.01 |
| 756.5 | C40H70O10PN | PS(34:4) | 0.00 | 0.00 |
| 758.5 | C40H72O10PN | PS(34:3) | 0.00 | 0.02 |
| 760.5 | C40H76O10PN | PS(34:2) | 0.04 | 0.23 |
| 762.5 | C40H76O10PN | PS(34:1) | 0.51 | 0.09 |
| 764.5 | C40H78O10PN | PS(34:0) | 0.00 | 0.02 |
| 780.5 | C42H70O10PN | PS(36:6) | 0.00 | 0.01 |
| 782.5 | C42H72O10PN | PS(36:5) | 0.00 | 0.03 |
| 784.5 | C42H74O10PN | PS(36:4) | 0.01 | 0.00 |
| 786.5 | C42H76O10PN | PS(36:3) | 0.01 | 0.03 |
| 788.5 | C42H78O10PN | PS(36:2) | 0.29 | 0.09 |
| 790.6 | C42H80O10PN | PS(36:1) | 1.96 | 0.68 |
| 792.6 | C42H82O10PN | PS(36:0) | 0.00 | 0.00 |
| 806.5 | C44H72O10PN | PS(38:7) | 0.00 | 0.00 |
| 808.5 | C44H74O10PN | PS(38:6) | 0.00 | 0.00 |
| 810.5 | C44H76O10PN | PS(38:5) | 0.01 | 0.00 |
| 812.5 | C44H78O10PN | PS(38:4) | 0.13 | 0.01 |
| 814.6 | C44H80O10PN | PS(38:3) | 0.26 | 0.04 |
| 816.6 | C44H82O10PN | PS(38:2) | 0.10 | 0.03 |
| 818.6 | C44H84O10PN | PS(38:1) | 0.07 | 0.03 |
| 820.6 | C44H86O10PN | PS(38:0) | 0.00 | 0.00 |
| 832.5 | C46H74O10PN | PS(40:8) | 0.00 | 0.01 |
| 834.5 | C46H76O10PN | PS(40:7) | 0.00 | 0.01 |
| 836.5 | C46H78O10PN | PS(40:6) | 0.08 | 0.00 |
| 838.6 | C46H80O10PN | PS(40:5) | 0.17 | 0.00 |
| 840.6 | C46H82O10PN | PS(40:4) | 0.22 | 0.01 |
| 842.6 | C46H84O10PN | PS(40:3) | 0.05 | 0.00 |
| 844.6 | C46H86O10PN | PS(40:2) | 0.03 | 0.01 |
| 846.6 | C46H88O10PN | PS(40:1) | 0.03 | 0.01 |
| 854.5 | C48H72O10PN | PS(42:11) | 0.00 | 0.00 |
| 856.5 | C48H74O10PN | PS(42:10) | 0.00 | 0.00 |
| 858.5 | C48H76O10PN | PS(42:9) | 0.00 | 0.00 |
| 860.5 | C48H78O10PN | PS(42:8) | 0.00 | 0.00 |
| 862.6 | C48H80O10PN | PS(42:7) | 0.00 | 0.01 |
| 864.6 | C48H82O10PN | PS(42:6) | 0.00 | 0.01 |
| 866.6 | C48H84O10PN | PS(42:5) | 0.00 | 0.00 |
| 880.5 | C50H74O10PN | PS(44:12) | 0.00 | 0.00 |
| 882.5 | C50H76O10PN | PS(44:11) | 0.00 | 0.00 |
| 884.5 | C50H78O10PN | PS(44:10) | 0.00 | 0.00 |
| 886.6 | C50H80O10PN | PS(44:9) | 0.00 | 0.00 |
| 888.6 | C50H82O10PN | PS(44:8) | 0.00 | 0.01 |
| 890.6 | C50H84O10PN | PS(44:7) | 0.00 | 0.00 |
| 892.6 | C50H86O10PN | PS(44:6) | 0.00 | 0.00 |
| 894.6 | C50H88O10PN | PS(44:5) | 0.00 | 0.00 |
| 896.6 | C50H90O10PN | PS(44:4) | 0.00 | 0.00 |
| 898.6 | C50H92O10PN | PS(44:3) | 0.00 | 0.00 |
| 900.7 | C50H94O10PN | PS(44:2) | 0.00 | 0.00 |
| Total PS | | | 4.02 | 1.63 |
| 746.5 | C40H76O9PN | ePS(34:2) | 0.00 | 0.01 |
| 748.5 | C40H78O9PN | ePS(34:1) | 0.02 | 0.00 |
| 772.5 | C42H78O9PN | ePS(36:3) | 0.00 | 0.00 |
| 774.6 | C42H80O9PN | ePS(36:2) | 0.03 | 0.01 |
| 776.6 | C42H82O9PN | ePS(36:1) | 0.10 | 0.01 |
| 778.6 | C42H84O9PN | ePS(36:0) | 0.01 | 0.01 |
| 794.5 | C44H76O9PN | ePS(38:6) | 0.01 | 0.01 |
| 796.5 | C44H78O9PN | ePS(38:5) | 0.01 | 0.00 |
| 798.6 | C44H80O9PN | ePS(38:4) | 0.01 | 0.00 |
| 800.6 | C44H82O9PN | ePS(38:3) | 0.00 | 0.01 |

TABLE 4-continued

Identities of Lipids Detected in Exosome/HG-NV.

| Mass | Formula | Name | Exosomes | % by group HG-NV |
|---|---|---|---|---|
| 802.6 | C44H84O9PN | ePS(38:2) | 0.02 | 0.00 |
| 804.6 | C44H86O9PN | ePS(38:1) | 0.02 | 0.02 |
| 824.6 | C46H82O9PN | ePS(40:5) | 0.01 | 0.00 |
| 826.6 | C46H84O9PN | ePS(40:4) | 0.00 | 0.00 |
| 828.6 | C46H86O9PN | ePS(40:3) | 0.02 | 0.00 |
| 830.6 | C46H88O9PN | ePS(40:2) | 0.01 | 0.00 |
| Total ePS | | | 0.26 | 0.08 |
| 658.4 | C35H61O8P | PA(32:4) | 0.00 | 0.00 |
| 660.4 | C35H63O8P | PA(32:3) | 0.00 | 0.00 |
| 662.4 | C35H65O8P | PA(32:2) | 0.00 | 0.02 |
| 664.5 | C35H67O8P | PA(32:1) | 0.01 | 0.00 |
| 666.5 | C35H69O8P | PA(32:0) | 0.02 | 0.07 |
| 686.4 | C37H65O8P | PA(34:4) | 0.00 | 0.01 |
| 688.5 | C37H67O8P | PA(34:3) | 0.00 | 0.01 |
| 690.5 | C37H69O8P | PA(34:2) | 0.00 | 0.00 |
| 692.5 | C37H71O8P | PA(34:1) | 0.07 | 0.00 |
| 710.4 | C39H65O8P | PA(36:6) | 0.00 | 0.01 |
| 712.5 | C39H67O8P | PA(36:5) | 0.00 | 0.02 |
| 714.5 | C39H69O8P | PA(36:4) | 0.00 | 0.00 |
| 716.5 | C39H71O8P | PA(36:3) | 0.00 | 0.00 |
| 718.5 | C39H73O8P | PA(36:2) | 0.09 | 0.00 |
| 738.5 | C41H69O8P | PA(38:6) | 0.00 | 0.00 |
| 740.5 | C41H71O8P | PA(38:5) | 0.00 | 0.00 |
| 742.5 | C41H73O8P | PA(38:4) | 0.05 | 0.00 |
| 744.5 | C41H75O8P | PA(38:3) | 0.06 | 0.03 |
| 746.5 | C41H77O8P | PA(38:2) | 0.01 | 0.00 |
| 764.5 | C43H71O8P | PA(40:7) | 0.00 | 0.04 |
| 766.5 | C43H73O8P | PA(40:6) | 0.00 | 0.00 |
| 768.5 | C43H75O8P | PA(40:5) | 0.01 | 0.03 |
| Total PA | | | 0.32 | 0.23 |
| 710.5 | C36H69O10P | PG(30:1) | 0.00 | 0.07 |
| 712.5 | C36H71O10P | PG(30:0) | 0.01 | 0.68 |
| 736.5 | C38H71O10P | PG(32:2) | 0.00 | 0.20 |
| 738.5 | C38H73O10P | PG(32:1) | 0.00 | 0.33 |
| 740.5 | C38H75O10P | PG(32:0) | 0.01 | 0.49 |
| 760.5 | C40H71O10P | PG(34:4) | 0.00 | 0.01 |
| 762.5 | C40H73O10P | PG(34:3) | 0.00 | 0.01 |
| 764.5 | C40H75O10P | PG(34:2) | 0.00 | 0.24 |
| 766.5 | C40H77O10P | PG(34:1) | 0.01 | 0.12 |
| 768.5 | C40H79O10P | PG(34:0) | 0.00 | 0.04 |
| 788.5 | C42H75O10P | PG(36:4) | 0.00 | 0.04 |
| 790.5 | C42H77O10P | PG(36:3) | 0.00 | 0.00 |
| 792.5 | C42H79O10P | PG(36:2) | 0.02 | 0.05 |
| 794.6 | C42H81O10P | PG(36:1) | 0.01 | 0.01 |
| 812.5 | C44H75O10P | PG(38:6) | 0.00 | 0.00 |
| 814.5 | C44H77O10P | PG(38:5) | 0.00 | 0.00 |
| Total PG | | | 0.06 | 2.32 |
| Total Polar Lipids | | | 100 | 100 |
| 30:1 | C33H66O5N | 14:0/16:1 | 0.11 | 0.89 |
| | | 16:0/14:1 | 0.36 | 1.85 |
| 30:0 | C33H68O5N | 14:0/16:0 | 0.44 | 1.04 |
| | | 16:0/16:1 | 1.30 | 4.53 |
| 32:1 | C35H70O5N | 16:0/16:0 | 2.36 | 3.47 |
| 32:0 | C35H72O5N | 18:3/16:1 | 0.08 | 0.81 |
| 34:4 | C37H68O5N | 14:0/20:4 | 0.00 | 0.47 |
| | | 14:1/20:3 | 0.07 | 0.08 |
| | | 18:3/16:0 | 0.36 | 2.98 |
| 34:3 | C37H70O5N | 18:2/16:1 | 0.10 | 2.11 |
| | | 14:0/20:3 | 0.04 | 0.00 |
| | | 18:2/16:0 | 3.54 | 16.86 |
| 34:2 | C37H72O5N | 18:1/16:1 | 2.82 | 4.70 |
| | | 18:1/16:0 | 8.13 | 8.54 |
| 34:1 | C37H74O5N | 18:0/16:1 | 1.78 | 1.87 |
| | | 18:3/18:3 | 0.00 | 0.71 |
| 36:6 | C39H68O5N | 16:1/20:5 | 0.07 | 0.23 |
| | | 18:3/18:2 | 0.16 | 5.83 |
| 36:5 | C39H70O5N | 16:0/20:5 | 0.08 | 0.11 |
| | | 16:1/20:4 | 0.00 | 0.17 |
| | | 18:3/18:1 | 1.21 | 5.28 |
| 36:4 | C39H72O5N | 18:2/18:2 | 0.44 | 7.29 |
| | | 16:0/20:4 | 0.47 | 0.25 |
| | | 16:1/20:3 | 0.17 | 0.04 |
| | | 18:3/18:0 | 0.05 | 0.16 |
| 36:3 | C39H74O5N | 18:2/18:1 | 1.92 | 6.97 |
| | | 16:0/20:3 | 0.27 | 0.31 |
| | | 16:1/20:2 | 0.09 | 0.06 |
| | | 18:2/18:0 | 3.24 | 3.25 |
| 36:2 | C39H76O5N | 18:1/18:1 | 11.06 | 5.32 |
| | | 16:0/20:2 | 0.18 | 0.12 |
| | | 18:1/18:0 | 20.15 | 4.82 |
| 36:1 | C39H78O5N | 18:2/20:5 | 0.04 | 0.00 |
| 38:7 | C41H70O5N | 18:3/20:4 | 0.05 | 0.08 |
| | | 18:1/20:5 | 0.00 | 0.20 |
| 38:6 | C41H72O5N | 18:2/20:4 | 0.00 | 0.06 |
| | | 16:0/22:6 | 0.22 | 0.44 |
| | | 16:1/22:5 | 0.00 | 0.15 |
| | | 18:0/20:5 | 0.00 | 0.17 |
| 38:5 | C41H74O5N | 18:1/20:4 | 1.41 | 0.37 |
| | | 18:2/20:3 | 0.00 | 0.22 |
| | | 18:3/20:2 | 0.00 | 0.81 |
| | | 16:0/22:5 | 0.29 | 1.25 |
| | | 16:1/22:4 | 0.13 | 0.06 |
| | | 18:0/20:4 | 16.81 | 1.31 |
| 38:4 | C41H76O5N | 18:1/20:3 | 1.85 | 0.05 |
| | | 16:0/22:4 | 0.06 | 0.27 |
| | | 18:0/20:3 | 17.84 | 3.16 |
| 38:3 | C41H78O5N | 18:1/20:2 | 0.23 | 0.26 |
| Total DAG | | | 100 | 100 |
| 818.7 | C51H96O6N | 48:3 | 1.39 | 2.66 |
| 820.7 | C51H98O6N | 48:2 | 8.94 | 8.51 |
| 822.8 | C51H100O6N | 48:1 | 18.00 | 13.53 |
| 824.8 | C51H102O6N | 48:0 | 0.00 | 0.00 |
| 830.8 | C53H100O5N | e50:4 | 0.30 | 0.19 |
| 832.8 | C53H102O5N | e50:3 | 0.89 | 1.43 |
| 834.8 | C53H104O5N | e50:2 | 3.67 | 4.69 |
| 836.8 | C53H106O5N | e50:1 | 1.00 | 1.53 |
| 838.8 | C53H108O5N | e50:0 | 0.29 | 0.10 |
| 844.7 | C53H98O6N | 50:4 | 1.70 | 2.81 |
| 846.8 | C53H100O6N | 50:3 | 8.60 | 10.47 |
| 848.8 | C53H102O6N | 50:2 | 22.11 | 16.95 |
| 850.8 | C53H104O6N | 50:1 | 4.01 | 1.96 |
| 852.8 | C53H106O6N | 50:0 | 0.02 | 0.05 |
| 856.8 | C55H102O5N | e52:5 | 0.24 | 0.11 |
| 858.8 | C55H104O5N | e52:4 | 0.28 | 0.51 |
| 860.8 | C55H106O5N | e52:3 | 1.59 | 1.10 |
| 862.8 | C55H108O5N | e52:2 | 3.54 | 2.41 |
| 864.8 | C55H110O5N | e52:1 | 0.53 | 0.32 |
| 866.9 | C55H112O5N | e52:0 | 0.04 | 0.59 |
| 868.7 | C55H98O6N | 52:6 | 0.00 | 2.72 |
| 870.8 | C55H100O6N | 52:5 | 1.39 | 6.99 |
| 872.8 | C55H102O6N | 52:4 | 2.93 | 5.90 |
| 874.8 | C55H104O6N | 52:3 | 10.40 | 10.43 |
| 876.8 | C55H106O6N | 52:2 | 8.13 | 4.03 |
| Total NL271 16:1 acyl containing | | | 100 | 100 |
| 820.7 | C51H98O6N | 48:2 | 1.87 | 2.80 |
| 822.8 | C51H100O6N | 48:1 | 10.48 | 8.93 |
| 824.8 | C51H102O6N | 48:0 | 14.75 | 7.33 |
| 830.8 | C53H100O5N | e50:4 | 0.02 | 0.09 |
| 832.8 | C53H102O5N | e50:3 | 0.01 | 0.17 |
| 834.8 | C53H104O5N | e50:2 | 0.82 | 0.75 |
| 836.8 | C53H106O5N | e50:1 | 4.17 | 2.24 |
| 838.8 | C53H108O5N | e50:0 | 1.68 | 0.92 |
| 844.7 | C53H98O6N | 50:4 | 0.15 | 0.41 |
| 846.8 | C53H100O6N | 50:3 | 1.33 | 2.01 |
| 848.8 | C53H102O6N | 50:2 | 8.78 | 9.83 |
| 850.8 | C53H104O6N | 50:1 | 23.47 | 15.47 |
| 852.8 | C53H106O6N | 50:0 | 3.66 | 2.97 |
| 856.8 | C55H102O5N | e52:5 | 0.00 | 0.05 |
| 858.8 | C55H104O5N | e52:4 | 0.07 | 0.04 |
| 860.8 | C55H106O5N | e52:3 | 0.38 | 0.56 |
| 862.8 | C55H108O5N | e52:2 | 3.13 | 1.20 |
| 864.8 | C55H110O5N | e52:1 | 3.15 | 1.56 |

TABLE 4-continued

Identities of Lipids Detected in Exosome/HG-NV.

| Mass | Formula | Name | Exosomes | % by group HG-NV |
|---|---|---|---|---|
| 866.9 | C55H112O5N | e52:0 | 0.64 | 0.85 |
| 868.7 | C55H98O6N | 52:6 | 0.00 | 0.75 |
| 870.8 | C55H100O6N | 52:5 | 0.38 | 2.66 |
| 872.8 | C55H102O6N | 52:4 | 1.61 | 8.84 |
| 874.8 | C55H104O6N | 52:3 | 4.03 | 9.64 |
| 876.8 | C55H106O6N | 52:2 | 9.47 | 15.21 |
| 878.8 | C55H108O6N | 52:1 | 5.94 | 4.72 |
| Total NL273 16:0 acyl containing | | | 100 | 100 |
| 846.8 | C53H100O6N | 50:3 | 7.99 | 2.99 |
| 848.8 | C53H102O6N | 50:2 | 15.47 | 3.19 |
| 850.8 | C53H104O6N | 50:1 | 0.00 | 0.14 |
| 852.8 | C53H106O6N | 50:0 | 0.00 | 0.01 |
| 856.8 | C55H102O5N | e52:5 | 0.21 | 0.16 |
| 858.8 | C55H104O5N | e52:4 | 0.41 | 0.47 |
| 860.8 | C55H106O5N | e52:3 | 2.48 | 1.06 |
| 862.8 | C55H108O5N | e52:2 | 1.59 | 0.37 |
| 864.8 | C55H110O5N | e52:1 | 0.00 | 0.02 |
| 866.9 | C55H112O5N | e52:0 | 0.00 | 0.27 |
| 868.7 | C55H98O6N | 52:6 | 0.11 | 1.41 |
| 870.8 | C55H100O6N | 52:5 | 1.33 | 4.99 |
| 872.8 | C55H102O6N | 52:4 | 0.00 | 3.04 |
| 874.8 | C55H104O6N | 52:3 | 18.11 | 10.97 |
| 876.8 | C55H106O6N | 52:2 | 3.96 | 1.78 |
| 878.8 | C55H108O6N | 52:1 | 0.00 | 0.11 |
| 880.8 | C55H110O6N | 52:0/e54:7 | 0.00 | 0.11 |
| 882.8 | C57H104O5N | e54:6 | 0.26 | 0.17 |
| 884.8 | C57H106O5N | e54:5 | 0.44 | 0.43 |
| 886.8 | C57H108O5N | e54:4 | 1.00 | 0.30 |
| 888.8 | C57H110O5N | e54:3 | 2.35 | 0.68 |
| 890.9 | C57H112O5N | e54:2 | 0.00 | 0.20 |
| 892.9 | C57H114O5N | e54:1 | 0.45 | 2.84 |
| 894.8 | C57H100O6N | 54:7/e54:0 | 2.68 | 12.61 |
| 896.8 | C57H102O6N | 54:6 | 9.63 | 23.96 |
| 898.8 | C57H104O6N | 54:5 | 8.58 | 14.89 |
| 900.8 | C57H106O6N | 54:4 | 11.94 | 10.42 |
| 902.8 | C57H108O6N | 54:3 | 10.97 | 2.07 |
| 904.8 | C57H110O6N | 54:2 | 0.05 | 0.34 |
| Total NL297 18:2 acyl containing | | | 100 | 100 |
| 848.8 | C53H102O6N | 50:2 | 10.72 | 6.29 |
| 850.8 | C53H104O6N | 50:1 | 16.28 | 7.29 |
| 852.8 | C53H106o6N | 50:0 | 0.00 | 0.00 |
| 856.8 | C55H102O5N | e52:5 | 0.01 | 0.01 |
| 858.8 | C55H104O5N | e52:4 | 0.11 | 0.14 |
| 860.8 | C55H106O5N | e52:3 | 0.82 | 0.58 |
| 862.8 | C55H108O5N | e52:2 | 4.82 | 2.06 |
| 864.8 | C55H110O5N | e52:1 | 2.09 | 0.89 |
| 866.9 | C55H112O5N | e52:0 | 0.00 | 0.00 |
| 868.7 | C55H98O6N | 52:6 | 0.05 | 0.07 |
| 870.8 | C55H100O6N | 52:5 | 0.12 | 0.60 |
| 872.8 | C55H102O6N | 52:4 | 0.81 | 2.39 |
| 874.8 | C55H104O6N | 52:3 | 7.84 | 10.52 |
| 876.8 | C55H106O6N | 52:2 | 21.81 | 19.91 |
| 878.8 | C55H108O6N | 52:1 | 3.27 | 2.76 |
| 880.8 | C55H110O6N | 52:0/e54:7 | 0.18 | 0.09 |
| 882.8 | C57H104O5N | e54:6 | 0.05 | 0.02 |
| 884.8 | C57H106O5N | e54:5 | 0.01 | 0.05 |
| 886.8 | C57H108O5N | e54:4 | 0.38 | 0.28 |
| 888.8 | C57H110O5N | e54:3 | 3.13 | 0.87 |
| 890.9 | C57H112O5N | e54:2 | 2.82 | 1.48 |
| 892.9 | C57H114O5N | e54:1 | 0.46 | 0.32 |
| 894.8 | C57H100O6N | 54:7/e54:0 | 0.04 | 0.83 |
| 896.8 | C57H102O6N | 54:6 | 0.26 | 3.23 |
| 898.8 | C57H104O6N | 54:5 | 1.99 | 9.85 |
| 900.8 | C57H106O6N | 54:4 | 3.51 | 10.74 |
| 902.8 | C57H108O6N | 54:3 | 11.00 | 12.88 |
| 904.8 | C57H110O6N | 54:2 | 6.46 | 4.99 |
| 906.8 | C57H112O6N | 54:1 | 0.95 | 0.86 |
| Total NL299 18:1 acyl containing | | | 100 | 100 |
| 850.8 | C53H104O6N | 50:1 | 9.47 | 5.61 |
| 852.8 | C53H106O6N | 50:0 | 13.30 | 8.88 |
| 856.8 | C55H102O5N | e52:5 | 0.00 | 0.12 |
| 858.8 | C55H104O5N | e52:4 | 0.00 | 0.00 |
| 860.8 | C55H106O5N | e52:3 | 0.16 | 0.17 |
| 862.8 | C55H108O5N | e52:2 | 1.05 | 0.56 |
| 864.8 | C55H110O5N | e52:1 | 4.48 | 1.89 |
| 866.9 | C55H112O5N | e52:0 | 1.75 | 0.93 |
| 868.7 | C55H98O6N | 52:6 | 0.24 | 0.28 |
| 870.8 | C55H100O6N | 52:5 | 0.02 | 0.20 |
| 872.8 | C55H102O6N | 52:4 | 0.22 | 0.54 |
| 874.8 | C55H104O6N | 52:3 | 1.43 | 1.55 |
| 876.8 | C55H106O6N | 52:2 | 11.00 | 11.53 |
| 878.8 | C55H108O6N | 52:1 | 18.33 | 15.44 |
| 880.8 | C55H110O6N | 52:0/e54:7 | 3.90 | 6.78 |
| 882.8 | C57H104O5N | e54:6 | 0.00 | 0.13 |
| 884.8 | C57H106O5N | e54:5 | 0.07 | 0.39 |
| 886.8 | C57H108O5N | e54:4 | 0.15 | 0.04 |
| 888.8 | C57H110O5N | e54:3 | 0.45 | 0.37 |
| 890.9 | C57H112O5N | e54:2 | 1.69 | 1.26 |
| 892.9 | C57H114O5N | e54:1 | 2.11 | 1.21 |
| 894.8 | C57H100O6N | 54:7/e54:0 | 0.96 | 1.48 |
| 896.8 | C57H102O6N | 54:6 | 0.06 | 0.34 |
| 898.8 | C57H104O6N | 54:5 | 0.13 | 1.81 |
| 900.8 | C57H106O6N | 54:4 | 2.23 | 8.55 |
| 902.8 | C57H108O6N | 54:3 | 4.24 | 7.50 |
| 904.8 | C57H110O6N | 54:2 | 14.40 | 13.68 |
| 906.8 | C57H112O6N | 54:1 | 7.76 | 4.89 |
| 908.9 | C57H114O6N | 54:0/e56:7 | 0.40 | 3.87 |
| Total NL301 18:0 acyl containing | | | 100 | 100 |
| 880.8 | C55H110O6N | 52:0/e54:7 | 0.19 | 3.42 |
| 882.8 | C57H104O5N | e54:6 | 0.60 | 4.47 |
| 884.8 | C57H106O5N | e54:5 | 5.31 | 5.66 |
| 886.8 | C57H108O5N | e54:4 | 2.85 | 2.97 |
| 888.8 | C57H110O5N | e54:3 | 0.28 | 1.30 |
| 890.9 | C57H112O5N | e54:2 | 0.46 | 3.67 |
| 892.9 | C57H114O5N | e54:1 | 1.46 | 4.18 |
| 894.8 | C57H100O6N | 54:7/e54:0 | 1.69 | 0.00 |
| 896.8 | C57H102O6N | 54:6 | 8.65 | 13.06 |
| 898.8 | C57H104O6N | 54:5 | 21.78 | 19.36 |
| 900.8 | C57H106O6N | 54:4 | 10.58 | 6.29 |
| 902.8 | C57H108O6N | 54:3 | 0.00 | 0.60 |
| 904.8 | C57H110O6N | 54:2 | 0.90 | 0.55 |
| 906.8 | C57H112O6N | 54:1 | 1.79 | 0.99 |
| 908.9 | C57H114O6N | 54:0/e56:7 | 1.78 | 2.16 |
| 910.8 | C59H108O5N | e56:6 | 4.33 | 2.27 |
| 912.8 | C59H110O5N | e56:5 | 7.16 | 3.84 |
| 914.9 | C59H112O5N | e56:4 | 2.11 | 0.61 |
| 916.9 | C59H114O5N | e56:3 | 0.00 | 0.62 |
| 918.9 | C59H116O5N | e56:2 | 0.08 | 1.28 |
| 920.9 | C59H118O5N | e56:1 | 1.17 | 3.35 |
| 922.8 | C59H104O6N | 56:7/e56:0 | 3.16 | 3.22 |
| 924.8 | C59H106O6N | 56:6 | 10.01 | 7.26 |
| 926.8 | C59H108O6N | 56:5 | 11.43 | 5.39 |
| 928.8 | C59H110O6N | 56:4 | 2.21 | 3.47 |
| Total NL321 20:4 acyl containing | | | 100 | 100 |

Example 5—Biological Effect of HG-NVs on Tumor Progression

Figure 5A:
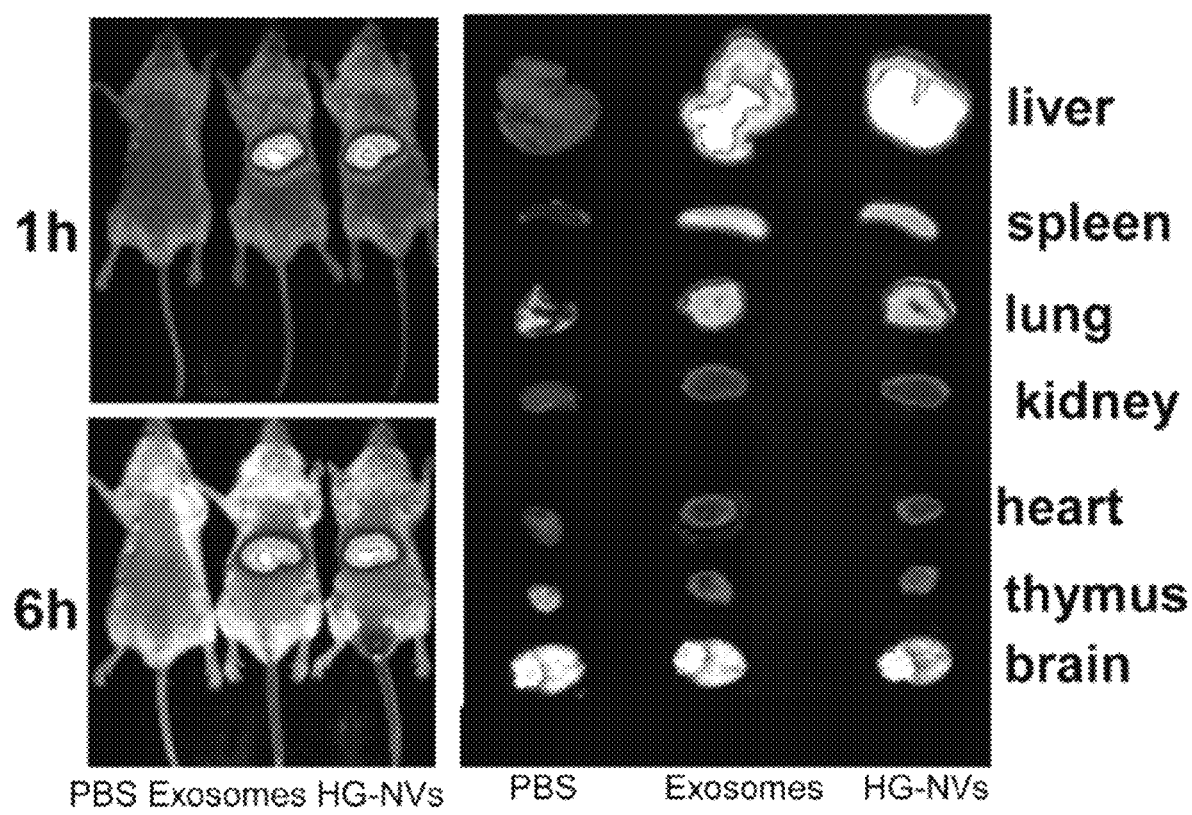
FIGS. 5A-5C include images and graphs showing in vivo biodistribution of the HG-NVs, including.
Figure 5B:
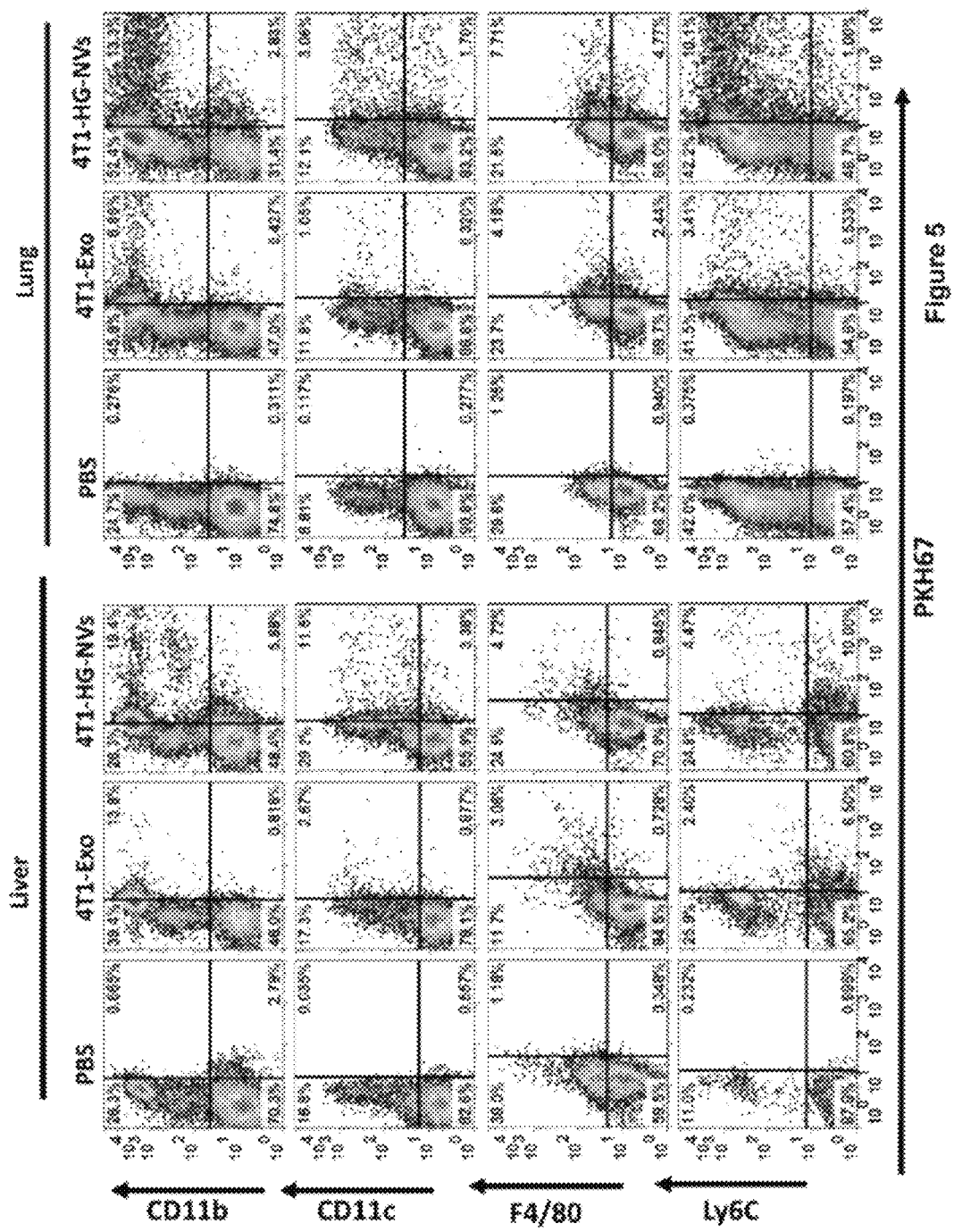

The in vivo biological effects of HG-NVs was next investigated. To determine the tissue tropism of HG-NVs in comparison with exosomes, in vivo biodistribution of DiR-labeled HG-NVs or DiR-labeled exosomes was evaluated in mice using a Kodak Image Station 4000 MM Pro system. Six h after a tail-vein injection, DiR fluorescent signals were predominantly detected in the liver, lung, and splenic tissues (FIG. 5A). FACS analysis of cells of mice 16 h after receiving an i.v. injection of PKH67-labeled HG-NVs, revealed that higher percentages of CD11c$^+$ DCs, F4/80$^+$ macrophages and Ly6C$^+$ monocytes took up HG-NVs than exosomes (FIG. 2B, Table 6).

TABLE 6

Percent of cell up taking 4T1 exosomes and HG-NVs

| Cell Type | Liver (n = 5) | | | Lung (n = 5) | | |
|---|---|---|---|---|---|---|
| | PBS | Exosomes | HG-NVs | PBS | Exosomes | HG-NVs |
| CD11c$^+$PKH26$^+$ (DC cells) | 0.5 ± 0.1 | 2.4 ± 0.2 | 11.2 ± 0.3 | 0.1 ± 0.1 | 1.1 ± 0.2 | 3.1 ± 0.2 |
| F4/80$^+$PKH26$^+$ (macrophages) | 1.1 ± 0.1 | 3.1 ± 0.3 | 4.6 ± 0.5 | 1.3 ± 0.1 | 4.1 ± 0.4 | 7.6 ± 0.1 |
| Ly6C$^+$PKH26$^+$ (monocytes) | 0.2 ± 0.1 | 2.4 ± 0.2 | 4.5 ± 0.3 | 0.4 ± 0.1 | 3.3 ± 0.6 | 10.3 ± 0.1 |
| CD11b$^+$PKH26$^+$ (Myeloid cells) | 0.7 ± 0.1 | 13.8 ± 0.4 | 19.3 ± 0.7 | 0.3 ± 0.1 | 6.9 ± 0.3 | 13.2 ± 0.8 |

Figure 5C:
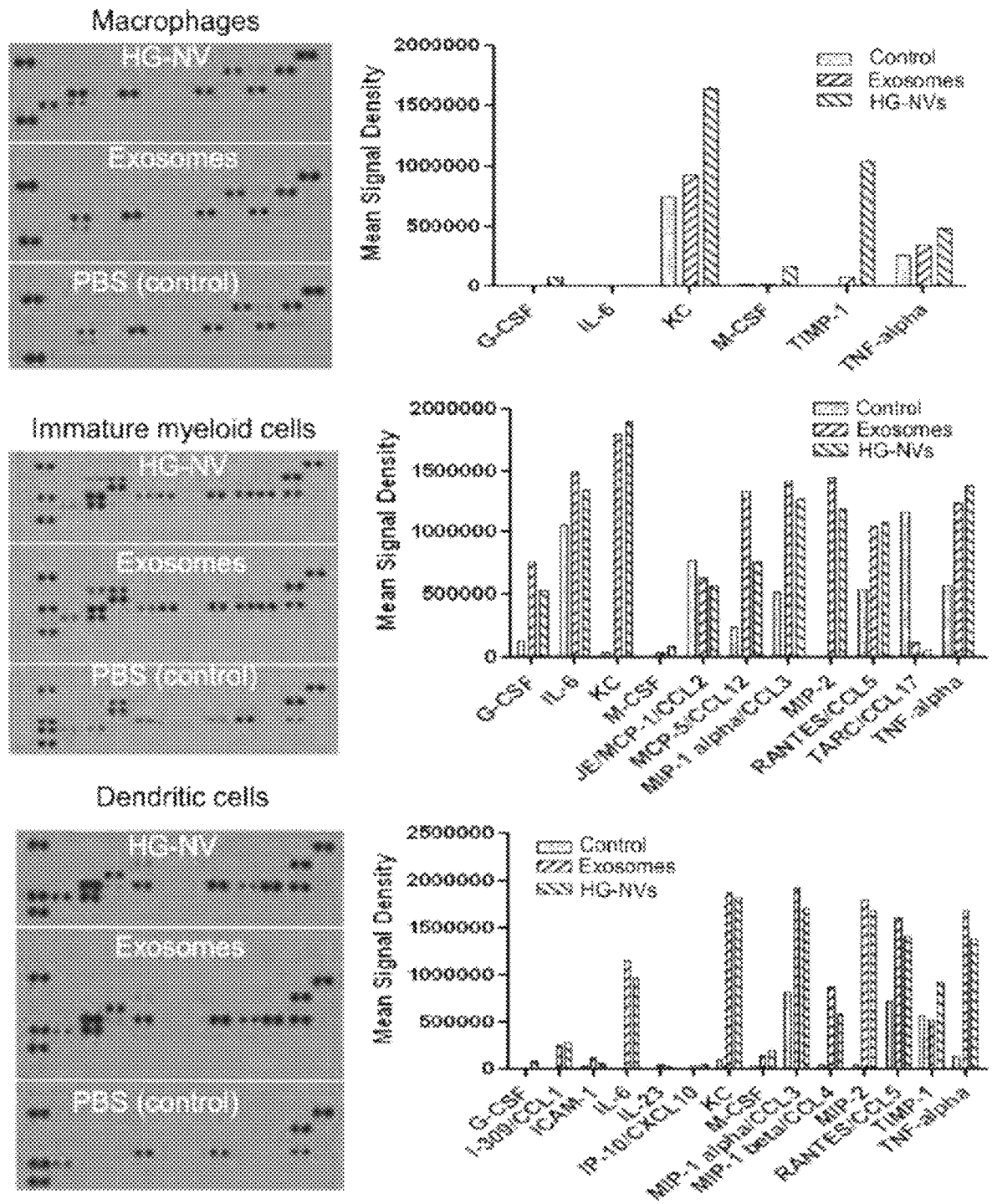

Since the cells targeted by HG-NVs were known to be involved in immune modulation by releasing an array of cytokines, an analysis of cytokines (FIG. 8) released from bone marrow derived DCs, macrophages, and immature monocytes was conducted after they were stimulated with HG-NVs or exosomes or PBS as a control. Inflammatory cytokine array data (FIG. 5C) indicated that the cytokines identified were in much higher concentrations in the cell culture supernatants of macrophages stimulated with HG-NVs for 7 h than with exosomes. MCSF, TIMP1 and KC were increased substantially in HG-NV treated macrophages in comparison to exosome treated macrophages. It was also noticed, in general, that stronger inflammatory cytokine signals were detected in the cell culture supernatants of cells treated with either HG-NVs or exosomes than from the PBS control.

Among these three cell types mentioned previously, macrophages are the most abundant in the many different types of tumors and metastatic tissues. The upregulated cytokines detected in culture supernatants of macrophages were known to promote tumor progression. Therefore, it was further hypothesized that HG-NVs might enhance or increase tumor progression. Like human breast tumor, 4T1 cells provide an established model of stage IV breast cancer because these cells form tumors when transplanted into mammary glands of mice and spontaneously metastasize to lungs and liver. Therefore, the 4T1 murine breast tumor model was used to test this hypothesis.

Figure 6A:
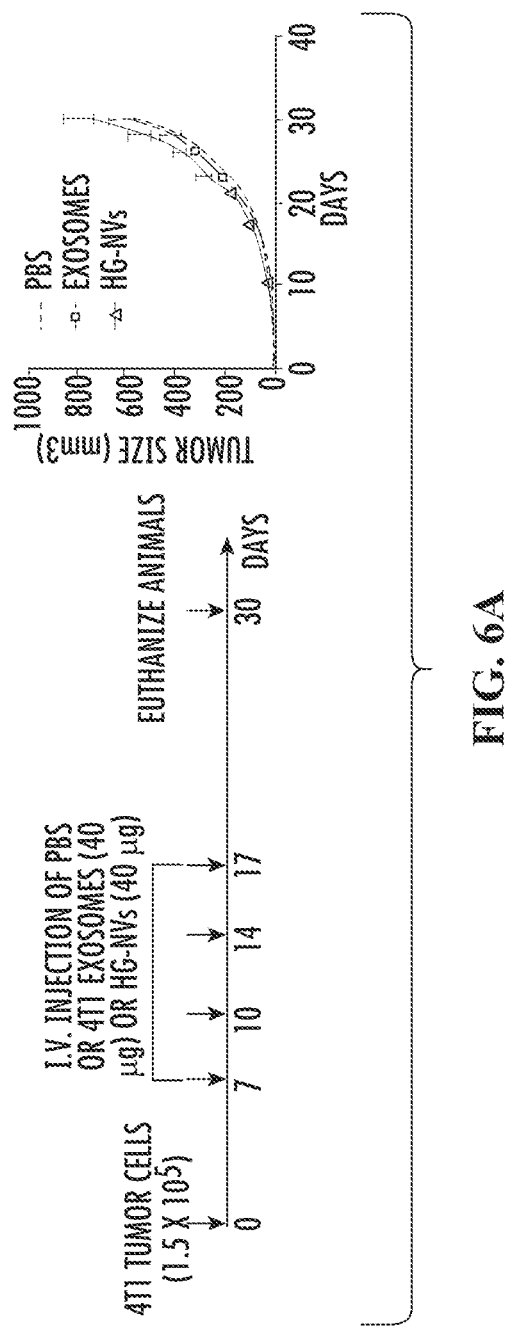

To investigate whether HG-NVs affected progression of primary and metastatic breast cancer, 1×10$^4$ 4T1 cells were injected into inguinal mammary fat pads of BALB/c mice. Seven-day tumor bearing mice with similar size tumors were selected and i.v. injected with 4T1 HG-NVs or 4T1 exosomes (40 μg in 50 μl PBS) every three days for 10 days. The host mice displayed visible mammary tumors within two weeks after injection and tumors became necrotic by day 30 which resulted in the experiment being terminated due to Institutional Animal Care and Use Committee guidelines. At day 30 after tumor cells were injected, the tumors in mice receiving HG-NVs increased more rapidly than did tumors in mice receiving exosomes or PBS as a control (FIG. 6A). It was then sought to determine whether an i.v. injection of 4T1 HG-NVs would promote or increase metastatic occurrence of the tumor. Hematoxylin and eosin staining revealed a significant increase in the number of micro-metastases in the lung (FIG. 6B, upper panel) and liver (FIG. 6B, bottom panel) compared to exosomes or PBS under the same conditions. ELISA analysis of peripheral blood of mice treated with HG-NVs further revealed a significant increase in TNFα and IL6 detected in the lung and liver tissue lysates and the immunosuppressive cytokine IL-10 (FIG. 6C). Collectively, these data indicated that HG-NVs promoted early dissemination of the 4T1 cells from primary tumors to lung and liver.

Figure 6B:
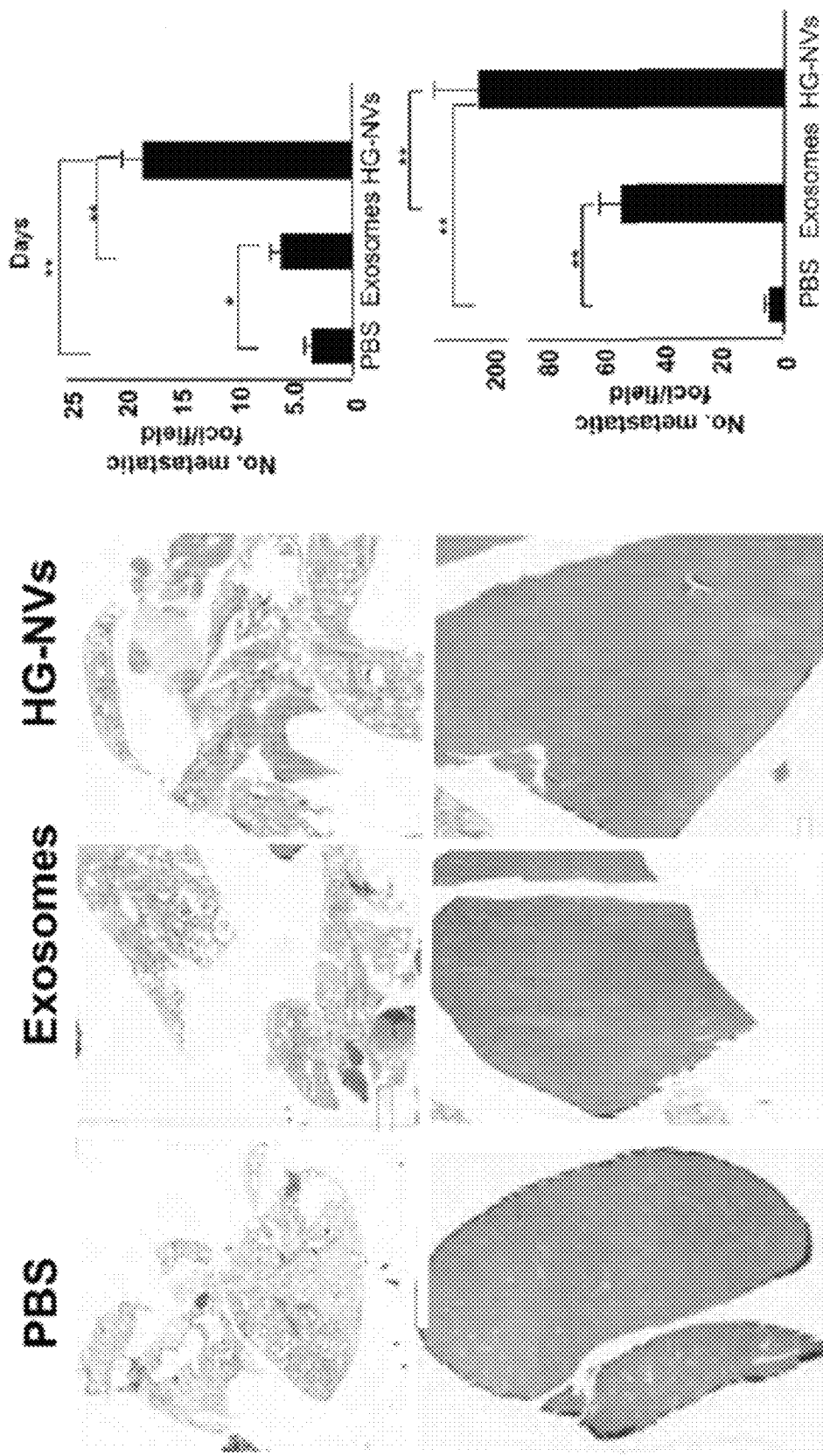
Figure 6D:
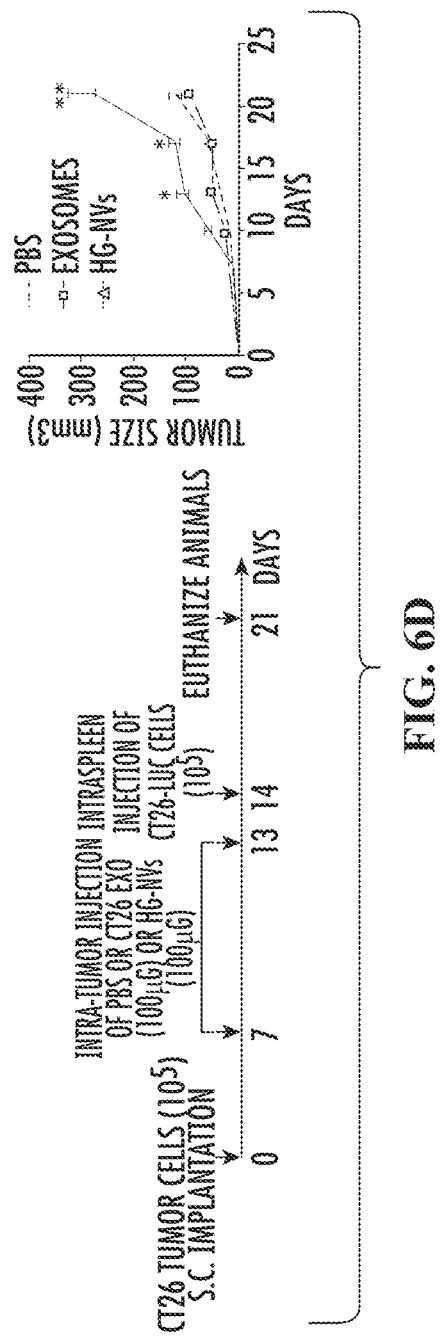
Figure 6E:
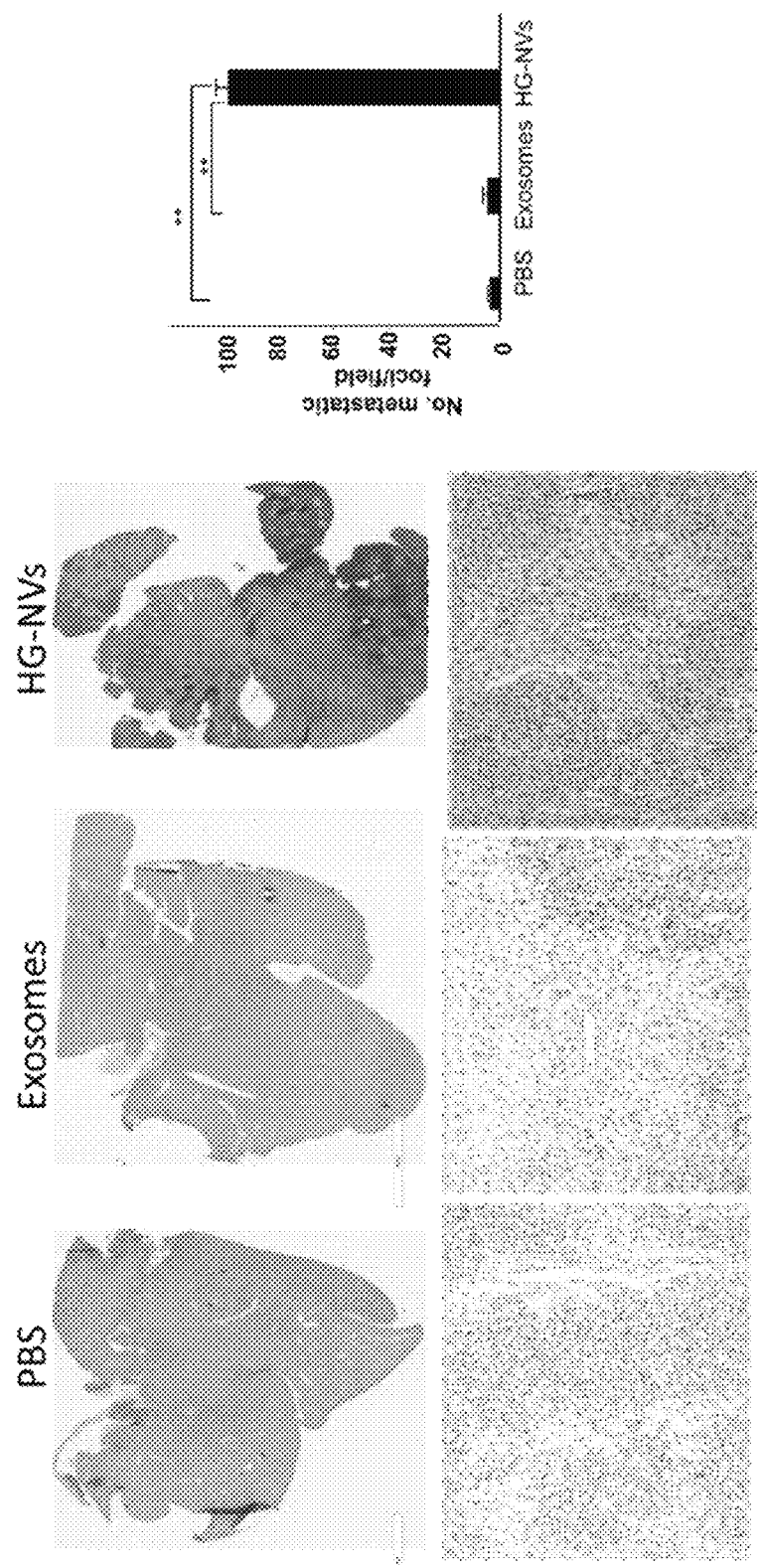
Figure 9:
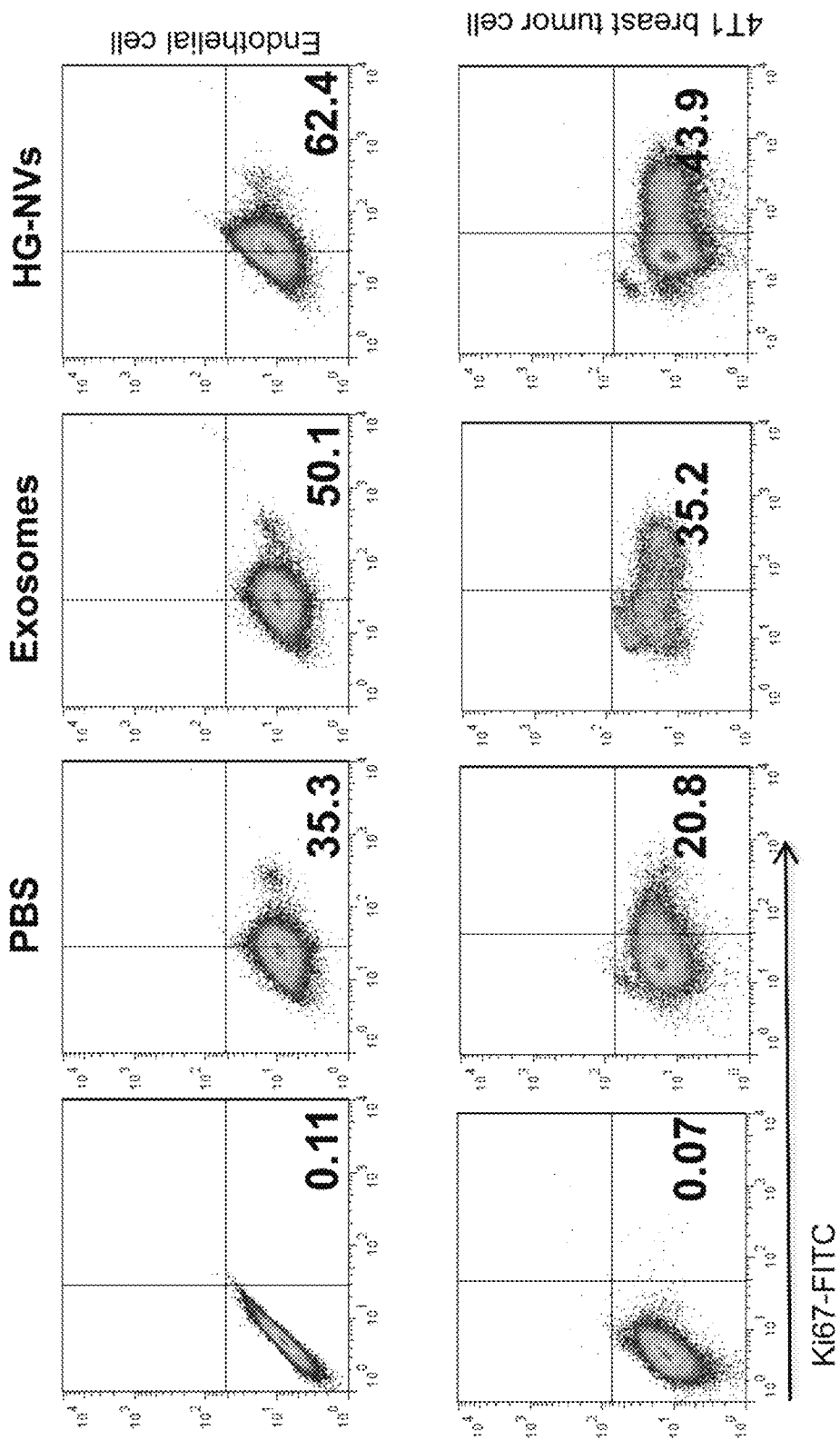
FIG. 9 includes graphs showing that 4T1 HG-NVs are more potent in promoting the proliferation of tumor cells and endothelial cells, where 24 h after mouse endothelial cells (upper panel) or 4T1 tumor cells (lower panel) were co-cultured with 4T1 HG-NVs and exosomes, the percentages of Ki67+ cells were quantitatively analyzed by FACS.
Figure 10:
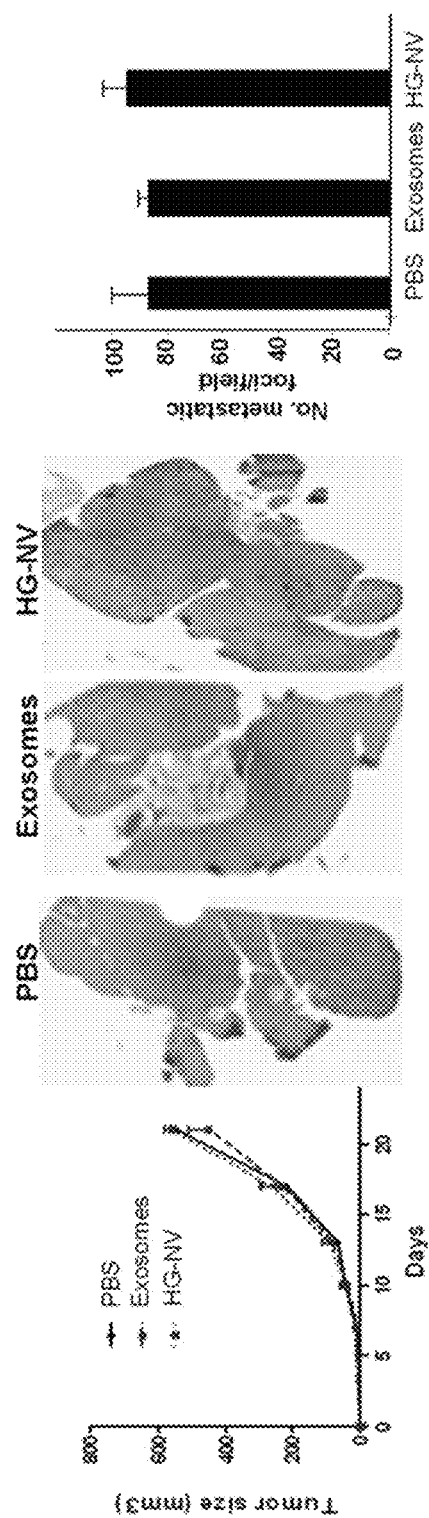
FIG. 10 includes growth curves of CT26 tumors (left panel) generated by subcutaneous injection of CT26 cells in NK and T cell deficient NOG mice (5 mice per group) which have been intratumorally injected with CT26 exosomes or HG-NVs (100 μg/mouse), and a representative photograph and graph showing the H&E stained tissue of CT26 micro-tumors per field of sectioned liver (right panel) of 21 day tumor bearing mice.

Exosomes released from tumor cells also had a local effect. Published data suggest that exosomes are released into the extracellular tissue space and play a role in tissue remodeling processes. Matrix degradation by tumor exosomes has severe consequences on tumor and host cell adhesion, motility, and invasiveness. Ki67 FACS analysis results indicated that HG-NVs were more potent in promoting endothelial cell and tumor cell proliferation (FIG. 9). To address the local effect of HG-NVs on tumor growth, the CT26 colon cancer model was used. The CT26 colon cancer model required a much longer time for tumor metastasis to occur than the 4T1 model. Therefore, the CT26 colon cancer model was suitable for studying the local effect of HG-NVs in terms of tumor growth before metastasis takes place. Seven-day tumor bearing mice with similar size tumors were treated with CT26 tumor HG-NVs or exosomes or PBS as a control. HG-NVs were injected into the tumor every week for a total of two injections. Their effect on primary colon carcinoma growth was then determined. HG-NVs significantly accelerated tumor growth in comparison with exosomes or PBS (FIG. 6D), an effect that was evident by day 13 (FIG. 6D, right panel *p<0.05, *p<0.001) after the subcutaneous injection of CT-26 tumor cells. On day 14, the tumor volume in the HG-NV treated group was 264.3±38.6 mm$^3$, which was significantly larger than tumors in the exosome or PBS treated groups (FIG. 6d, *p<0.001). It was further hypothesized that HG-NV treatment of mice creates a pre-metastatic niche not only by i.v. injection of HG-NVs as shown in FIG. 6B but via an intra-tumoral injection as well. To test this hypothesis, one day after the last intra-tumoral injection of HG-NVs, tumor bearing mice were intrasplenic injected with CT26 tumor cells, which was a standard procedure for studying murine colon cancer metastasis to the liver. As shown in FIG. 6E, intra-tumor injection of HG-NVs led to a significant increase in the number and size of micro-metastases in the liver compared with exosomes or PBS under the same conditions. However, when NK and T cell deficient NOG mice instead of immunocompetent BALB/c mice were used, no significant differences in terms of tumor growth and liver metastasis was detected (FIG. 10), indicating that HG-NV-mediated suppression of NK and T cells may be involved in enhancing tumor growth and liver metastasis.

Discussion of Examples 1-5

In the foregoing study, it was shown that with minimal in vitro manipulation only HG-NVs from blood and cell culture supernatants can be detected with a Zetasizer. Five lines of evidence support that HG-NVs are a previously unrecognized nanovesicle. First, unlike exosomes, HG-NVs are much smaller in size (8-12 nm in diameter versus 50-150 nm in diameter of exosomes), much less heterogeneous in size and less negatively charged (−10±5 mV) than exosomes (−40±10 mV) released from the same cell types. Second, after depletion of exosomes using a standard protocol, HG-NVs were still present in the samples. Third, based on composition analysis, a number of unique proteins and RNAs were identified as being present/absent in the HG-NVs compared with exosomes released from both human and murine breast tumor cells. Fourth, in order to characterize exosomes, they must be concentrated using different technologies that could cause an alteration in their properties. Determining whether the properties of exosomes have actually been altered after in vitro concentration is a challenging problem. In contrast, without concentration or other forms of laboratory manipulation, HG-NVs (8-12 nm in diameter) from blood or cell supernatants can be detected with a Nanosizer. Finally, from a biological effects perspective, the above-described data indicated that HG-NVs were different from exosomes (1) in their RNA profile from tumor bearing mice and LPS challenged mice; (2) in their cytokine profile from macrophages, dendritic cells and immature myeloid cells; and (3) in their promoting tumor growth based on two different mouse tumor models used in this study.

Figure 11:
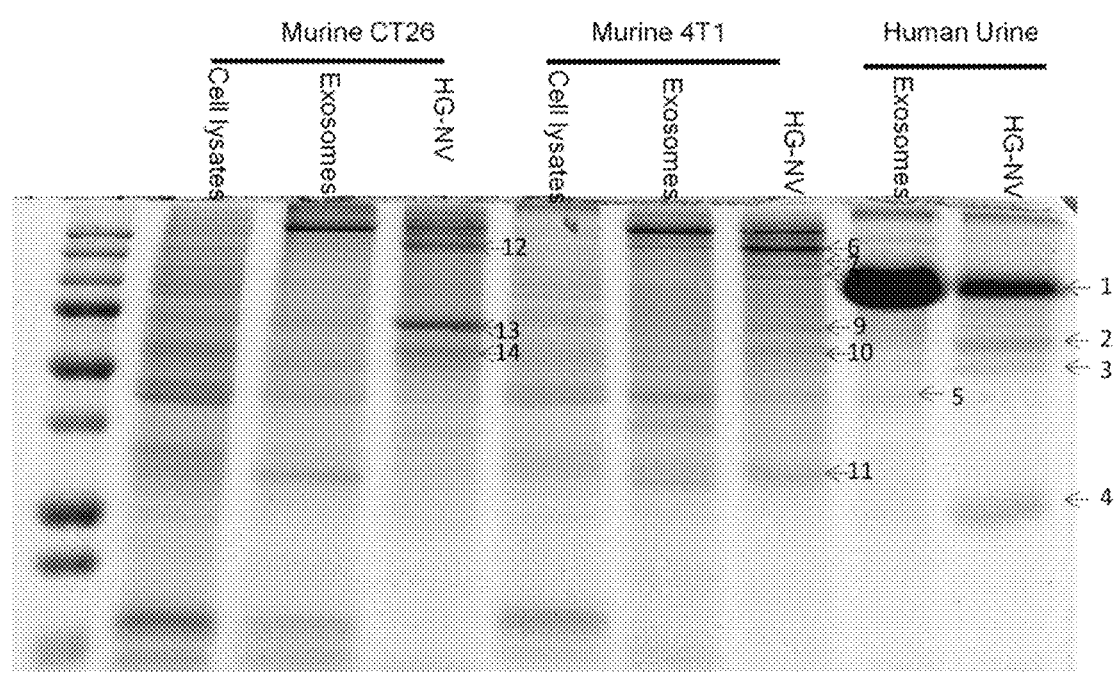
FIG. 11 includes graphs showing, after electrophoresis on an 8% SDS polyacrylamide gel, protein lysates (50 μg/lane) extracted from cells, exosomes, HG-NVs were stained with Coomassie Blue and scanned using an Odyssey Imaging System.

Recently, EV-derived molecules have been extensively studied for potential use as biomarkers. In the above study, the composition of 4T1 breast tumor cell-derived and MDA-MB-231 human breast tumor cell-derived HG-NVs was further characterized. Besides the proteins and RNAs that are shared among exosomes, the fact that HG-NVs contained much higher copies of specific proteins and RNAs than exosomes released from the same type of tumor cells supported the idea that HG-NV derived RNA and proteins may be used as potential biomarkers for prodiagnosis and diagnosis. This notion was also supported by the specific migration pattern of HG-NV proteins stained with Coomassie dye (FIG. 11). Furthermore, the data showed that one of the biological attributes of the tumor cell-derived HG-NVs was to promote tumor growth and metastasis through immunomodulation. This effect greatly increased the complexity by which tumor cells communicate with immune cells, including macrophages, dendritic cells, and immature myeloid cells that take up HG-NVs as we demonstrated in this study. Cytokines released from macrophages, dendritic cells, and immature myeloid cells participate in immunomodulation in terms of promoting or inhibiting tumor progression and cytokines are major mediators that regulate other immune cell mediated anti-tumor activity including NK, NKT and T cells. The results presented in the above study indicated that in addition to the identical cytokines induced by exosomes and HG-NVs, some cytokines were only induced by HG-NVs or the exosomes. These cytokines were proinflammatory in nature. A hallmark of tumor progression is the involvement of proinflammatory cytokines. Tumor-associated macrophages and immature myeloid cells are the hallmark of immunosuppression in tumors. Therefore, the above-described findings can provide a rationale for developing better cancer immunotherapy strategies by blocking the production of tumor HG-NVs or inhibiting uptake by tumor associated macrophages and immature myeloid cells. Furthermore, given the fact that tumor HG-NV-mediated promotion of lung and liver metastasis did not occur in NOG immune deficient mice, the HG-NVs can have a general role in regulating immune activities of liver, lung and spleen.

In the above study, it was also demonstrated that one of the characteristics of HG-NVs was that they are much smaller in size than reported for other EVs. In general, the size of a chemically-synthesized nanoparticle typically prevents rapid renal clearance (typically must be less than 20 nm) and also prevents uptake by the liver and spleen (typically particles must be greater than 100 nm). However, unlike chemically synthesized nanoparticles, i.v. injected tumor cell-derived HG-NVs do not accumulate in the kidney but do accumulate in lung and liver.

The finding that HG-NVs were a predominant population among EVs raises a number of important questions to be addressed in the EV field. To date there are almost no data in this field that address the question of whether there is a predominant EV among EVs. The findings reported in this study provide the basis for further exploring whether HG-NVs are originally released from the same or different compartment of the mother cells as exosomes or whether HG-NVs are originally released from exosomes.

Both exosomes and other EVs could be taken up by the same recipient cells. Currently available isolation and purification methods do not allow one to fully distinguish the biological effect between subpopulations of EVs, and lacking such technology hampers the identification of the in vivo physiological relevance and function for each subpopulation. This study demonstrated that tumor cell HG-NVs can be separated from other EVs by differential centrifugation and purified by a simple column based filtration platform. This strategy not only provides a means for investigating the biological effects of HG-NVs released from non-tumor cells under physiological and pathophysiological conditions in general, but it could also provide a possible means to investigate a specific cell type where HG-NVs are detected.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lo Cicero A, Stahl P D and Raposo G. Extracellular vesicles shuffling intercellular messages: for good or for bad. Current opinion in cell biology. 2015; 35:69-77.
2. Raposo G and Stoorvogel W. Extracellular vesicles: exosomes, microvesicles, and friends. The Journal of cell biology. 2013; 200(4):373-383.
3. Thery C, Ostrowski M and Segura E. Membrane vesicles as conveyors of immune responses. Nature reviews Immunology. 2009; 9(8):581-593.
4. Aalberts M, van Dissel-Emiliani F M, van Adrichem N P, van Wijnen M, Wauben M H, Stout T A and Stoorvogel W. Identification of distinct populations of prostasomes that differentially express prostate stem cell antigen, annexin A1, and GLIPR2 in humans. Biology of reproduction. 2012; 86(3):82.
5. Caby M P, Lankar D, Vincendeau-Scherrer C, Raposo G and Bonnerot C. Exosomal-like vesicles are present in human blood plasma. International immunology. 2005; 17(7):879-887.
6. Huebner A R, Somparn P, Benjachat T, Leelahavanichkul A, Avihingsanon Y, Fenton R A and Pisitkun T. Exosomes in urine biomarker discovery. Advances in experimental medicine and biology. 2015; 845:43-58.
7. Ogawa Y, Miura Y, Harazono A, Kanai-Azuma M, Akimoto Y, Kawakami H, Yamaguchi T, Toda T, Endo T, Tsubuki M and Yanoshita R. Proteomic analysis of two types of exosomes in human whole saliva. Biological & pharmaceutical bulletin. 2011; 34(1):13-23.

8. Admyre C, Johansson S M, Qazi K R, Filen J J, Lahesmaa R, Norman M, Neve E P, Scheynius A and Gabrielsson S. Exosomes with immune modulatory features are present in human breast milk. Journal of immunology. 2007; 179(3):1969-1978.

9. Asea A, Jean-Pierre C, Kaur P, Rao P, Linhares I M, Skupski D and Witkin S S. Heat shock protein-containing exosomes in mid-trimester amniotic fluids. Journal of reproductive immunology. 2008; 79(1):12-17.

10. Navabi H, Croston D, Hobot J, Clayton A, Zitvogel L, Jasani B, Bailey-Wood R, Wilson K, Tabi Z, Mason M D and Adams M. Preparation of human ovarian cancer ascites-derived exosomes for a clinical trial. Blood cells, molecules & diseases. 2005; 35(2):149-152.

11. Gutwein P, Stoeck A, Riedle S, Gast D, Runz S, Condon T P, Marme A, Phong M C, Linderkamp O, Skorokhod A and Altevogt P. Cleavage of L1 in exosomes and apoptotic membrane vesicles released from ovarian carcinoma cells. Clinical cancer research: an official journal of the American Association for Cancer Research. 2005; 11(7):2492-2501.

12. Redzic J S, Ung T H and Graner M W. Glioblastoma extracellular vesicles: reservoirs of potential biomarkers. Pharmacogenomics and personalized medicine. 2014; 7:65-77.

13. Street J M, Barran P E, Mackay C L, Weidt S, Balmforth C, Walsh T S, Chalmers R T, Webb D J and Dear J W. Identification and proteomic profiling of exosomes in human cerebrospinal fluid. Journal of translational medicine. 2012; 10:5.

14. Marzesco A M, Janich P, Wilsch-Brauninger M, Dubreuil V, Langenfeld K, Corbeil D and Huttner W B. Release of extracellular membrane particles carrying the stem cell marker prominin-1 (CD133) from neural progenitors and other epithelial cells. Journal of cell science. 2005; 118(Pt 13):2849-2858.

15. Akers J C, Ramakrishnan V, Kim R, Skog J, Nakano I, Pingle S, Kalinina J, Hua W, Kesari S, Mao Y, Breakefield X O, Hochberg F H, Van Meir E G, Carter B S and Chen C C. MiR-21 in the extracellular vesicles (EVs) of cerebrospinal fluid (CSF): a platform for glioblastoma biomarker development. PloS one. 2013; 8(10):e78115.

16. Chen W W, Balaj L, Liau L M, Samuels M L, Kotsopoulos S K, Maguire C A, Loguidice L, Soto H, Garrett M, Zhu L D, Sivaraman S, Chen C, Wong E T, Carter B S, Hochberg F H, Breakefield X O, et al. BEAMing and Droplet Digital PCR Analysis of Mutant IDH1 mRNA in Glioma Patient Serum and Cerebrospinal Fluid Extracellular Vesicles. Molecular therapy Nucleic acids. 2013; 2:e109.

17. Masyuk A I, Huang B Q, Radtke B N, Gajdos G B, Splinter P L, Masyuk T V, Gradilone S A and LaRusso N F. Ciliary subcellular localization of TGR5 determines the cholangiocyte functional response to bile acid signaling. American journal of physiology Gastrointestinal and liver physiology. 2013; 304(11):G1013-1024.

18. Masyuk A I, Huang B Q, Ward C J, Gradilone S A, Banales J M, Masyuk T V, Radtke B, Splinter P L and LaRusso N F. Biliary exosomes influence cholangiocyte regulatory mechanisms and proliferation through interaction with primary cilia. American journal of physiology Gastrointestinal and liver physiology. 2010; 299(4):G990-999.

19. Nakano I, Garnier D, Minata M and Rak J. Extracellular vesicles in the biology of brain tumour stem cells—Implications for inter-cellular communication, therapy and biomarker development. Seminars in cell & developmental biology. 2015; 40:17-26.

20. Yang J, Wei F, Schafer C and Wong D T. Detection of tumor cell-specific mRNA and protein in exosome-like microvesicles from blood and saliva. PloS one. 2014; 9(11):e110641.

21. Zhang H G and Grizzle W E. Exosomes: a novel pathway of local and distant intercellular communication that facilitates the growth and metastasis of neoplastic lesions. The American journal of pathology. 2014; 184(1):28-41.

22. D'Souza-Schorey C and Clancy J W. Tumor-derived microvesicles: shedding light on novel microenvironment modulators and prospective cancer biomarkers. Genes & development. 2012; 26(12):1287-1299.

23. Thery C. Cancer: Diagnosis by extracellular vesicles. Nature. 2015; 523(7559):161-162.

24. Colombo M, Raposo G and Thery C. Biogenesis, secretion, and intercellular interactions of exosomes and other extracellular vesicles. Annual review of cell and developmental biology. 2014; 30:255-289.

25. Valadi H, Ekstrom K, Bossios A, Sjostrand M, Lee J J and Lotvall J O. Exosome-mediated transfer of mRNAs and microRNAs is a novel mechanism of genetic exchange between cells. Nature cell biology. 2007; 9(6):654-659.

26. Hoshino A, Costa-Silva B, Shen T L, Rodrigues G, Hashimoto A, Tesic Mark M, Molina H, Kohsaka S, Di Giannatale A, Ceder S, Singh S, Williams C, Soplop N, Uryu K, Pharmer L, King T, et al. Tumour exosome integrins determine organotropic metastasis. Nature. 2015; 527(7578):329-335.

27. Colegio O R, Chu N Q, Szabo A L, Chu T, Rhebergen A M, Jairam V, Cyrus N, Brokowski C E, Eisenbarth S C, Phillips G M, Cline G W, Phillips A J and Medzhitov R. Functional polarization of tumour-associated macrophages by tumour-derived lactic acid. Nature. 2014; 513(7519):559-563.

28. Qian B Z, Li J, Zhang H, Kitamura T, Zhang J, Campion L R, Kaiser E A, Snyder L A and Pollard J W. CCL2 recruits inflammatory monocytes to facilitate breast-tumour metastasis. Nature. 2011; 475(7355):222-225.

29. Chockalingam S and Ghosh S S. Macrophage colony-stimulating factor and cancer: a review. Tumour biology: the journal of the International Society for Oncodevelopmental Biology and Medicine. 2014; 35(11):10635-10644.

30. Osawa Y, Suetsugu A, Matsushima-Nishiwaki R, Yasuda I, Saibara T, Moriwaki H, Seishima M and Kozawa O. Liver acid sphingomyelinase inhibits growth of metastatic colon cancer. The Journal of clinical investigation. 2013; 123(2):834-843.

31. Denzer K, Kleijmeer M J, Heijnen H F, Stoorvogel W and Geuze H J. Exosome: from internal vesicle of the multivesicular body to intercellular signaling device. Journal of cell science. 2000; 113 Pt 19:3365-3374.

32. Lakkaraju A and Rodriguez-Boulan E. Itinerant exosomes: emerging roles in cell and tissue polarity. Trends in cell biology. 2008; 18(5):199-209.

33. Mathivanan S, Ji H and Simpson R J. Exosomes: extracellular organelles important in intercellular communication. Journal of proteomics. 2010; 73(10):1907-1920.

34. Yue S, Mu W, Erb U and Zoller M. The tetraspanins CD151 and Tspan8 are essential exosome components for the crosstalk between cancer initiating cells and their surrounding. Oncotarget. 2015; 6(4):2366-2384.
35. Pospichalova V, Svoboda J, Dave Z, Kotrbova A, Kaiser K, Klemova D, Ilkovics L, Hampl A, Crha I, Jandakova E, Minar L, Weinberger V and Bryja V. Simplified protocol for flow cytometry analysis of fluorescently labeled exosomes and microvesicles using dedicated flow cytometer. Journal of extracellular vesicles. 2015; 4:25530.
36. Coumans F A, van der Pol E, Boing A N, Hajji N, Sturk G, van Leeuwen T G and Nieuwland R. Reproducible extracellular vesicle size and concentration determination with tunable resistive pulse sensing. Journal of extracellular vesicles. 2014; 3:25922.
37. Linares R, Tan S, Gounou C, Arraud N and Brisson A R. High-speed centrifugation induces aggregation of extracellular vesicles. Journal of extracellular vesicles. 2015; 4:29509.
38. Ghesquiere B, Wong B W, Kuchnio A and Carmeliet P. Metabolism of stromal and immune cells in health and disease. Nature. 2014; 511(7508):167-176.
39. Biswas S K and Mantovani A. Macrophage plasticity and interaction with lymphocyte subsets: cancer as a paradigm. Nature immunology. 2010; 11(10):889-896.
40. Vivier E, Tomasello E, Baratin M, Walzer T and Ugolini S. Functions of natural killer cells. Nature immunology. 2008; 9(5):503-510.
41. Gagliani N, Hu B, Huber S, Elinav E and Flavell R A. The fire within: microbes inflame tumors. Cell. 2014; 157(4):776-783.
42. Kessenbrock K, Plaks V and Werb Z. Matrix metalloproteinases: regulators of the tumor microenvironment. Cell. 2010; 141(1):52-67.
43. Zhang L, Zhang S, Yao J, Lowery F J, Zhang Q, Huang W C, Li P, Li M, Wang X, Zhang C, Wang H, Ellis K, Cheerathodi M, McCarty J H, Palmieri D, Saunus J, et al. Microenvironment-induced PTEN loss by exosomal microRNA primes brain metastasis outgrowth. Nature. 2015; 527(7576):100-104.
44. Gomez Perdiguero E, Klapproth K, Schulz C, Busch K, Azzoni E, Crozet L, Garner H, Trouillet C, de Bruijn M F, Geissmann F and Rodewald H R. Tissue-resident macrophages originate from yolk-sac-derived erythromyeloid progenitors. Nature. 2015; 518(7540):547-551.
45. Gabrilovich D I and Nagaraj S. Myeloid-derived suppressor cells as regulators of the immune system. Nature reviews Immunology. 2009; 9(3):162-174.
46. Yu M and Zheng J. Clearance Pathways and Tumor Targeting of Imaging Nanoparticles. ACS nano. 2015.
47. Perez-Herrero E and Fernandez-Medarde A. Advanced targeted therapies in cancer: Drug nanocarriers, the future of chemotherapy. European journal of pharmaceutics and biopharmaceutics: official journal of Arbeitsgemeinschaft fur Pharmazeutische Verfahrenstechnik eV. 2015; 93:52-79.
48. Liu J, Yu M, Zhou C, Yang S, Ning X and Zheng J. Passive tumor targeting of renal-clearable luminescent gold nanoparticles: long tumor retention and fast normal tissue clearance. Journal of the American Chemical Society. 2013; 135(13):4978-4981.
49. Deshmukh M, Kutscher H L, Gao D, Sunil V R, Malaviya R, Vayas K, Stein S, Laskin J D, Laskin D L and Sinko P J. Biodistribution and renal clearance of biocompatible lung targeted poly(ethylene glycol) (PEG) nanogel aggregates. Journal of controlled release: official journal of the Controlled Release Society. 2012; 164(1):65-73.
50. Sa L T, Albernaz Mde S, Patricio B F, Falcao M V, Jr., Coelho B F, Bordim A, Almeida J C and Santos-Oliveira R. Biodistribution of nanoparticles: initial considerations. Journal of pharmaceutical and biomedical analysis. 2012; 70:602-604.
51. Jain S, Thakare V S, Das M, Godugu C, Jain A K, Mathur R, Chuttani K and Mishra A K. Toxicity of multiwalled carbon nanotubes with end defects critically depends on their functionalization density. Chemical research in toxicology. 2011; 24(11):2028-2039.
52. Vickers K C, Palmisano B T, Shoucri B M, Shamburek R D and Remaley A T. MicroRNAs are transported in plasma and delivered to recipient cells by high-density lipoproteins. Nature cell biology. 2011; 13(4):423-433.
53. Navab M, Reddy S T, Van Lenten B J and Fogelman A M. HDL and cardiovascular disease: atherogenic and atheroprotective mechanisms. Nature reviews Cardiology. 2011; 8(4):222-232.
54. Clancy J W, Sedgwick A, Rosse C, Muralidharan-Chari V, Raposo G, Method M, Chavrier P and D'Souza-Schorey C. Regulated delivery of molecular cargo to invasive tumour-derived microvesicles. Nature communications. 2015; 6:6919.
55. Minciacchi V R, Freeman M R and Di Vizio D. Extracellular vesicles in cancer: exosomes, microvesicles and the emerging role of large oncosomes. Seminars in cell & developmental biology. 2015; 40:41-51.
56. Webber J, Yeung V and Clayton A. Extracellular vesicles as modulators of the cancer microenvironment. Seminars in cell & developmental biology. 2015; 40:27-34.
57. Antonyak M A and Cerione R A. Microvesicles as mediators of intercellular communication in cancer. Methods in molecular biology. 2014; 1165:147-173.
58. Vader P, Breakefield X O and Wood M J. Extracellular vesicles: emerging targets for cancer therapy. Trends in molecular medicine. 2014; 20(7):385-393.
59. Lemoinne S, Thabut D, Housset C, Moreau R, Valla D, Boulanger C M and Rautou P E. The emerging roles of microvesicles in liver diseases. Nature reviews Gastroenterology & hepatology. 2014; 11(6):350-361.
60. Choudhuri K, Llodra J, Roth E W, Tsai J, Gordo S, Wucherpfennig K W, Kam L C, Stokes D L and Dustin M L. Polarized release of T-cell-receptor-enriched microvesicles at the immunological synapse. Nature. 2014; 507 (7490):118-123.
61. Mu J, Zhuang X, Wang Q, Jiang H, Deng Z B, Wang B, Zhang L, Kakar S, Jun Y, Miller D and Zhang H G. Interspecies communication between plant and mouse gut host cells through edible plant derived exosome-like nanoparticles. Molecular nutrition & food research. 2014; 58(7):1561-1573.
62. Zhuang X, Xiang X, Grizzle W, Sun D, Zhang S, Axtell R C, Ju S, Mu J, Zhang L, Steinman L, Miller D and Zhang H G. Treatment of brain inflammatory diseases by delivering exosome encapsulated anti-inflammatory drugs from the nasal region to the brain. Molecular therapy: the journal of the American Society of Gene Therapy. 2011; 19(10): 1769-1779.
63. Liu Y, Xiang X, Zhuang X, Zhang S, Liu C, Cheng Z, Michalek S, Grizzle W and Zhang H G. Contribution of MyD88 to the tumor exosome-mediated induction of myeloid derived suppressor cells. The American journal of pathology. 2010; 176(5):2490-2499.
64. Liu Y, Xiang X, Zhuang X, Zhang S, Liu C, Cheng Z, Michalek S, Grizzle W and Zhang H G. Contribution of MyD88 to the tumor exosome-mediated induction of myeloid derived suppressor cells. The American journal of pathology. 2010; 176(5):2490-2499.

65. Xiang X, Zhuang X, Ju S, Zhang S, Jiang H, Mu J, Zhang L, Miller D, Grizzle W and Zhang H G. miR-155 promotes macroscopic tumor formation yet inhibits tumor dissemination from mammary fat pads to the lung by preventing EMT. Oncogene. 2011; 30(31):3440-3453.

66. Xiang X, Poliakov A, Liu C, Liu Y, Deng Z B, Wang J, Cheng Z, Shah S V, Wang G J, Zhang L, Grizzle W E, Mobley J and Zhang H G. Induction of myeloid-derived suppressor cells by tumor exosomes. Int J Cancer. 2009; 124(11):2621-2633.

67. Wang Q, Zhuang X, Mu J, Deng Z B, Jiang H, Zhang L, Xiang X, Wang B, Yan J, Miller D and Zhang H G. Delivery of therapeutic agents by nanoparticles made of grapefruit-derived lipids. Nature communications. 2013; 4:1867.

68. Mu J, Zhuang X, Wang Q, Jiang H, Deng Z B, Wang B, Zhang L, Kakar S, Jun Y, Miller D and Zhang H G. Interspecies communication between plant and mouse host cells through edible plant derived exosome-like nanoparticles. Molecular nutrition & food research. 2014; 58(7):1561-1573.

69. Ju S, Mu J, Dokland T, Zhuang X, Wang Q, Jiang H, Xiang X, Deng Z B, Wang B, Zhang L, Roth M, Welti R, Mobley J, Jun Y, Miller D and Zhang H G. Grape exosome-like nanoparticles induce intestinal stem cells and protect mice from DSS-induced colitis. Molecular therapy: the journal of the American Society of Gene Therapy. 2013; 21(7):1345-1357.

70. Masukawa Y, Narita H, Sato H, Naoe A, Kondo N, Sugai Y, Oba T, Homma R, Ishikawa J, Takagi Y and Kitahara T. Comprehensive quantification of ceramide species in human stratum corneum. J Lipid Res. 2009; 50(8):1708-1719.

71. Yu S, Liu C, Su K, Wang J, Liu Y, Zhang L, Li C, Cong Y, Kimberly R, Grizzle W E, Falkson C and Zhang H G. Tumor exosomes inhibit differentiation of bone marrow dendritic cells. Journal of immunology. 2007; 178(11):6867-6875.

72. Wang B, Zhuang X, Deng Z B, Jiang H, Mu J, Wang Q, Xiang X, Guo H, Zhang L, Dryden G, Yan J, Miller D and Zhang H G. Targeted drug delivery to intestinal macrophages by bioactive nanovesicles released from grapefruit. Molecular therapy: the journal of the American Society of Gene Therapy. 2014; 22(3):522-534.

73. Liu C, Yu S, Zinn K, Wang J, Zhang L, Jia Y, Kappes J C, Barnes S, Kimberly R P, Grizzle W E and Zhang H G. Murine mammary carcinoma exosomes promote tumor growth by suppression of NK cell function. Journal of immunology. 2006; 176(3):1375-1385.

74. Wang Q, Ren Y, Mu J, Egilmez N K, Zhuang X, Deng Z, Zhang L, Yan J, Miller D and Zhang H G. Grapefruit-Derived Nanovectors Use an Activated Leukocyte Trafficking Pathway to Deliver Therapeutic Agents to Inflammatory Tumor Sites. Cancer research. 2015; 75(12):2520-2529.

75. Zhang, et al., entitled "Isolation, identification, and characterization of novel nanovesicles." Oncotarget. Vol. 7(27), p. 41346-41362.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A method for diagnosis or prognosis of a cancer in a subject, comprising:
providing a biological sample from a subject;
isolating one or more nanovesicles from the biological sample, the one or more nanovesicles having a diameter of about 8-12 nm, a charge of about −10±5 mV, one or more RNA molecules selected from Table 2b, one or more peptides selected from Tables 3b or 3d, one or more lipids selected from Table 4, or combinations thereof;
determining the amount in the biological sample of the one or more nanovesicles; and
comparing the amount of the one or more nanovesicles in the sample, if present, to a control level of the one or more nanovesicles, wherein the subject is diagnosed as having a cancer or a risk thereof if there is a measurable difference in the amount of the one or more nanovesicles in the sample as compared to the control level.

2. The method of claim 1, wherein the cancer is selected from the group consisting of breast cancer, colon cancer, lung cancer, and liver cancer.

3. The method of claim 2, wherein the cancer is a metastatic cancer.

4. The method of claim 1, wherein the biological sample comprises blood, plasma, or serum.

5. The method of claim 1, wherein the biological sample includes one or more tumor cells.

6. The method of claim 1, wherein the biological sample comprises a tumor biopsy.

7. The method of claim 1, wherein isolating the one or more nanovesicles comprises depleting exosomes from the biological sample prior to isolating the one or more nanovesicles.

8. The method of claim 1, further comprising determining an amount of the one or more peptides selected from Table 3b or 3d in the one or more nanovesicles using mass spectrometry (MS) analysis, immunoassay analysis, or both.

9. The method of claim 1, further comprising determining an amount in the sample of the one or more RNA molecules selected from Table 2b in the nanovesicles using a probe or primer specific for the one or more RNA molecules.

10. The method of claim 1, further comprising determining an amount in the sample of the one or more lipids selected from Table 4 in the nanovesicles using mass spectrometry (MS) analysis.

11. The method of claim 1, further comprising selecting a treatment or modifying a treatment for the cancer based on the determined amount of the one or more nanovesicles.

12. A method for identifying tumor metastasis in a subject, comprising:
providing a biological sample including one or more tumor cells from the subject;
fractionating the biological sample to obtain a fraction including one or more exosomes and one or more nanovesicles, the nanovesicles having a diameter of about 8-12 nm;
isolating the one or more nanovesicles from the fraction including the one or more nanovesicles;
determining the amount in the biological sample of the one or more nanovesicles; and
comparing the amount of the one or more nanovesicles in the biological sample, if present, to a control level of the one or more nanovesicles, wherein the subject is diagnosed as having a tumor metastasis, or a risk thereof, if there is a measurable difference in the amount of the one or more nanovesicles in the sample as compared to the control level.

13. The method of claim 12, wherein the cancer is selected from the group consisting of breast cancer, colon cancer, lung cancer, and liver cancer.

14. The method of claim 12, wherein the one or more nanovesicles includes a charge of about −10±5 mV, one or more RNA molecules selected from Table 2b, one or more peptides selected from Table 3b or 3d, one or more lipids selected from Table 4, or combinations thereof.

15. The method of claim 14, further comprising determining an amount of the one or more peptides selected from Table 3b or 3d in the one or more nanovesicles using mass spectrometry (MS) analysis, immunoassay analysis, or both.

16. The method of claim 14, further comprising determining an amount in the sample of the one or more RNA molecules selected from Table 2b in the nanovesicles using a probe or primer specific for the one or more RNA molecules.

17. The method of claim 14, further comprising determining an amount in the sample of the one or more lipids selected from Table 4 in the nanovesicles using mass spectrometry (MS) analysis.

* * * * *